(12) United States Patent
Bolduc

(10) Patent No.: US 8,690,897 B2
(45) Date of Patent: Apr. 8, 2014

(54) DEVICES, SYSTEMS, AND METHODS FOR PROSTHESIS DELIVERY AND IMPLANTATION, INCLUDING THE USE OF A FASTENER TOOL

(75) Inventor: Lee Bolduc, Sunnyvale, CA (US)

(73) Assignee: Aptus Endosystems, Inc., Sunnyvale, CA (US)

( * ) Notice: Subject to any disclaimer, the term of this patent is extended or adjusted under 35 U.S.C. 154(b) by 194 days.

(21) Appl. No.: 12/917,842

(22) Filed: Nov. 2, 2010

(65) Prior Publication Data
US 2011/0276062 A1    Nov. 10, 2011

Related U.S. Application Data

(60) Division of application No. 11/254,950, filed on Oct. 20, 2005, now Pat. No. 7,823,267, which is a continuation-in-part of application No. 11/254,619, filed on Oct. 20, 2005, and a continuation-in-part of application No. 10/692,283, filed on Oct. 23, 2003, now Pat. No. 7,147,657, said application No. 11/254,950 is a continuation-in-part of application No.

(Continued)

(51) Int. Cl.
*A61B 17/10* (2006.01)
*B23P 11/00* (2006.01)

(52) U.S. Cl.
USPC ........................................ 606/139; 29/525.01

(58) Field of Classification Search
USPC ............ 29/525.01, 428; 623/1.36, 1.11, 1.23, 623/1.55, 1.04, 1.51; 606/157, 191–198, 606/108
See application file for complete search history.

(56) References Cited

U.S. PATENT DOCUMENTS 2,033,039 A    3/1936   Limpert
3,499,222 A    3/1970   Linkow et al.
(Continued)

FOREIGN PATENT DOCUMENTS

AU    2002353807 B2    6/2003
AU    2004277897 B2    4/2005
(Continued)

OTHER PUBLICATIONS

Gadacz, T. et al. (Nov. 1995). "The Spiral Tacker: A New Technique for Stabilizing Prosthetic Mesh in Laparoscopic Hernia Repair," *Surgical Rounds* pp. 461-467.

(Continued)

*Primary Examiner* — John C Hong
(74) *Attorney, Agent, or Firm* — Schwegman, Lundberg & Woessner, P.A.

(57) ABSTRACT

Devices, systems, and methods for implanting radially expandable prostheses in the body lumens rely on tacking or anchoring the prostheses with separately introduced fasteners. The prostheses may be self-expanding or balloon expandable, and may include a single lumen or more than one lumen. After initial placement, a fastener applier system is introduced within the expanded prostheses to deploy a plurality of fasteners to at least one prosthesis end. The fasteners are usually helical fasteners which are releasably restrained on the fastener driver, and are delivered by rotation of the fastener driver. The fasteners may be applied singly, typically in circumferentially spaced-apart patterns about the interior of at least one end of the prosthesis. A lumen extension or lumens may be coupled to the prosthesis to extend the reach of the prosthesis within the implantation site. Fasteners may also be applied to the lumen extensions.

8 Claims, 44 Drawing Sheets

Related U.S. Application Data

10/786,465, filed on Feb. 25, 2004, now Pat. No. 8,231,639, which is a continuation-in-part of application No. 10/693,255, filed on Oct. 24, 2003, now Pat. No. 6,929,661, said application No. 11/254,950 is a continuation-in-part of application No. 10/307,226, filed on Nov. 29, 2002, now Pat. No. 8,075,570, and a continuation-in-part of application No. 10/669,881, filed on Sep. 24, 2003, now Pat. No. 7,491,232, and a continuation-in-part of application No. 11/166,411, filed on Jun. 24, 2005, now Pat. No. 8,092,519, which is a division of application No. 10/271,334, filed on Oct. 15, 2002, now Pat. No. 6,960,217.

(60) Provisional application No. 60/488,753, filed on Jul. 21, 2003, provisional application No. 60/489,011, filed on Jul. 21, 2003, provisional application No. 60/333,937, filed on Nov. 28, 2001.

(56) References Cited

U.S. PATENT DOCUMENTS

| | | |
|---|---|---|
| 3,686,740 A | 8/1972 | Shiley |
| 3,799,172 A | 3/1974 | Szpur |
| 4,140,126 A | 2/1979 | Choudhury |
| 4,255,820 A | 3/1981 | Rothermel et al. |
| 4,307,722 A | 12/1981 | Evans |
| 4,580,568 A | 4/1986 | Gianturco |
| 4,625,597 A | 12/1986 | Cast |
| 4,694,827 A | 9/1987 | Weiner et al. |
| 4,781,682 A | 11/1988 | Patel |
| 4,898,577 A | 2/1990 | Badger et al. |
| 4,899,747 A | 2/1990 | Garren et al. |
| 4,921,484 A | 5/1990 | Hillstead |
| 4,990,151 A | 2/1991 | Wallsten |
| 4,994,071 A | 2/1991 | MacGregor |
| 5,030,204 A | 7/1991 | Badger et al. |
| 5,042,707 A | 8/1991 | Taheri |
| 5,044,519 A | 9/1991 | Aoyama |
| 5,071,407 A | 12/1991 | Termin et al. |
| 5,104,399 A | 4/1992 | Lazarus |
| 5,185,004 A | 2/1993 | Lashinski et al. |
| 5,192,314 A | 3/1993 | Daskalakis |
| 5,207,695 A | 5/1993 | Trout, III |
| 5,282,824 A | 2/1994 | Gianturco |
| 5,290,295 A | 3/1994 | Querals et al. |
| 5,318,525 A | 6/1994 | West et al. |
| 5,320,630 A | 6/1994 | Ahmed |
| 5,330,490 A | 7/1994 | Wilk et al. |
| 5,330,503 A | 7/1994 | Yoon |
| 5,334,196 A | 8/1994 | Scott et al. |
| 5,364,351 A | 11/1994 | Heinzelman et al. |
| 5,383,880 A | 1/1995 | Hooven |
| 5,387,235 A | 2/1995 | Chuter |
| 5,409,498 A | 4/1995 | Braddock et al. |
| 5,456,713 A | 10/1995 | Chutter |
| 5,456,714 A | 10/1995 | Owen |
| 5,470,337 A | 11/1995 | Moss |
| 5,474,568 A | 12/1995 | Scott |
| 5,480,382 A | 1/1996 | Hammerslag et al. |
| 5,480,423 A | 1/1996 | Ravenscroft et al. |
| 5,489,295 A | 2/1996 | Piplani et al. |
| 5,522,881 A | 6/1996 | Lentz |
| 5,531,686 A | 7/1996 | Lundquist et al. |
| 5,534,007 A | 7/1996 | St. Germain et al. |
| 5,562,728 A | 10/1996 | Lazarus et al. |
| 5,571,171 A | 11/1996 | Barone et al. |
| 5,571,173 A | 11/1996 | Parodi |
| 5,582,616 A | 12/1996 | Bolduc et al. |
| 5,591,195 A | 1/1997 | Taheri et al. |
| 5,609,627 A | 3/1997 | Goicoechea et al. |
| 5,626,613 A | 5/1997 | Schmieding |
| 5,628,788 A | 5/1997 | Pinchuk |
| 5,632,772 A | 5/1997 | Alcime et al. |
| 5,634,936 A | 6/1997 | Linden et al. |
| 5,639,278 A | 6/1997 | Dereume et al. |
| 5,662,675 A | 9/1997 | Polanskyj Stockert et al. |
| 5,662,683 A | 9/1997 | Kay |
| 5,662,700 A | 9/1997 | Lazarus |
| 5,676,696 A | 10/1997 | Marcade |
| 5,676,697 A | 10/1997 | McDonald |
| 5,683,450 A | 11/1997 | Goicoechea et al. |
| 5,693,084 A | 12/1997 | Chuter |
| 5,693,086 A | 12/1997 | Goicoechea et al. |
| 5,700,269 A | 12/1997 | Pinchuk et al. |
| 5,702,343 A | 12/1997 | Alferness |
| 5,702,365 A | 12/1997 | King |
| 5,702,408 A | 12/1997 | Wales et al. |
| 5,707,376 A | 1/1998 | Kavteledze et al. |
| 5,713,907 A | 2/1998 | Bogendijk et al. |
| 5,733,325 A | 3/1998 | Robinson et al. |
| 5,749,921 A | 5/1998 | Lenker et al. |
| 5,755,777 A | 5/1998 | Chuter |
| 5,762,458 A | 6/1998 | Wang et al. |
| 5,769,884 A | 6/1998 | Solovay |
| 5,776,142 A | 7/1998 | Gunderson |
| 5,800,528 A | 9/1998 | Lederman et al. |
| 5,810,882 A | 9/1998 | Bolduc et al. |
| 5,814,016 A | 9/1998 | Valley et al. |
| 5,824,008 A | 10/1998 | Bolduc et al. |
| 5,824,037 A | 10/1998 | Fogarty et al. |
| 5,824,041 A | 10/1998 | Lenker et al. |
| 5,830,221 A | 11/1998 | Stein et al. |
| 5,830,229 A | 11/1998 | Konya et al. |
| 5,843,160 A | 12/1998 | Rhodes |
| 5,855,565 A | 1/1999 | Bar-Cohen et al. |
| 5,855,598 A | 1/1999 | Pinchuk |
| 5,861,003 A | 1/1999 | Latson et al. |
| 5,865,791 A | 2/1999 | Whayne |
| 5,876,432 A | 3/1999 | Lau et al. |
| 5,904,713 A | 5/1999 | Leschinsky |
| 5,906,619 A | 5/1999 | Olson et al. |
| 5,906,641 A | 5/1999 | Thomson et al. |
| 5,916,263 A | 6/1999 | Goicoechea et al. |
| 5,944,750 A | 8/1999 | Tanner et al. |
| 5,957,940 A | 9/1999 | Tanner et al. |
| 5,964,772 A | 10/1999 | Bolduc et al. |
| 5,968,053 A | 10/1999 | Revelas |
| 5,972,023 A | 10/1999 | Tanner et al. |
| 5,980,548 A | 11/1999 | Evans et al. |
| 5,993,401 A | 11/1999 | Inbe et al. |
| 5,993,466 A | 11/1999 | Yoon |
| 5,997,556 A | 12/1999 | Tanner |
| 6,016,810 A | 1/2000 | Ravenscroft |
| 6,024,703 A | 2/2000 | Zanelli et al. |
| 6,024,763 A | 2/2000 | Lenker et al. |
| 6,027,462 A | 2/2000 | Greene et al. |
| 6,070,589 A | 6/2000 | Keith et al. |
| 6,074,418 A | 6/2000 | Buchanan et al. |
| 6,077,214 A | 6/2000 | Mortier et al. |
| 6,077,297 A | 6/2000 | Robinson et al. |
| 6,086,582 A | 7/2000 | Altman et al. |
| 6,090,137 A | 7/2000 | Schmitt |
| 6,123,722 A | 9/2000 | Fogarty et al. |
| 6,126,685 A | 10/2000 | Lenker et al. |
| 6,129,685 A | 10/2000 | Howard, III |
| 6,145,509 A | 11/2000 | Tanner |
| 6,146,339 A | 11/2000 | Biagtan et al. |
| 6,152,144 A | 11/2000 | Lesh et al. |
| 6,168,610 B1 | 1/2001 | Marin et al. |
| 6,179,809 B1 | 1/2001 | Khairkhahan et al. |
| 6,197,049 B1 | 3/2001 | Shaolian et al. |
| 6,203,550 B1 | 3/2001 | Olson |
| 6,203,568 B1 | 3/2001 | Lombardi et al. |
| 6,217,597 B1 | 4/2001 | Tanner |
| 6,224,540 B1 | 5/2001 | Lederman et al. |
| 6,248,118 B1 | 6/2001 | Tanner et al. |
| 6,258,119 B1 | 7/2001 | Hussein et al. |
| 6,270,516 B1 | 8/2001 | Tanner et al. |
| 6,273,858 B1 | 8/2001 | Fox et al. |
| 6,286,514 B1 | 9/2001 | Lemelson |
| 6,287,315 B1 | 9/2001 | Wijeratne et al. |

(56) References Cited

U.S. PATENT DOCUMENTS

| | | |
|---|---|---|
| 6,293,906 B1 | 9/2001 | Vanden Hoek et al. |
| 6,296,656 B1 | 10/2001 | Bolduc et al. |
| 6,302,906 B1 | 10/2001 | Goicoechea et al. |
| 6,309,403 B1 | 10/2001 | Minor et al. |
| 6,319,278 B1 | 11/2001 | Quinn |
| 6,336,933 B1 | 1/2002 | Parodi |
| 6,346,118 B1 | 2/2002 | Baker et al. |
| 6,352,561 B1 | 3/2002 | Leopold et al. |
| 6,361,556 B1 | 3/2002 | Chuter |
| 6,368,345 B1 | 4/2002 | Dehdashtian et al. |
| 6,371,919 B1 | 4/2002 | Tanner et al. |
| 6,398,803 B1 | 6/2002 | Layne et al. |
| 6,402,680 B2 | 6/2002 | Mortier et al. |
| 6,402,780 B2 | 6/2002 | Williamson, IV et al. |
| 6,409,757 B1 | 6/2002 | Trout, III et al. |
| 6,423,059 B1 | 7/2002 | Hanson et al. |
| 6,425,856 B1 | 7/2002 | Shapland et al. |
| 6,428,565 B1 | 8/2002 | Wisselink |
| 6,454,796 B1 | 9/2002 | Barkman et al. |
| 6,458,152 B1 | 10/2002 | Khosravi et al. |
| 6,468,260 B1 | 10/2002 | Bumbalough et al. |
| 6,482,224 B1 | 11/2002 | Michler et al. |
| 6,520,974 B2 | 2/2003 | Tanner et al. |
| 6,544,253 B1 | 4/2003 | Tanner |
| 6,558,425 B2 | 5/2003 | Rockwood, Jr. |
| 6,562,051 B1 | 5/2003 | Bolduc et al. |
| 6,565,597 B1 | 5/2003 | Fearnot et al. |
| 6,576,009 B2 | 6/2003 | Ryan et al. |
| 6,580,417 B2 | 6/2003 | Rosenberg et al. |
| 6,592,593 B1 | 7/2003 | Parodi et al. |
| 6,592,615 B1 | 7/2003 | Marcade et al. |
| 6,595,912 B2 | 7/2003 | Lau et al. |
| 6,607,555 B2 | 8/2003 | Patterson et al. |
| 6,616,684 B1 | 9/2003 | Vidlund et al. |
| 6,652,555 B1 | 11/2003 | Vantassel et al. |
| 6,652,572 B2 | 11/2003 | Kugler et al. |
| 6,663,558 B2 | 12/2003 | Lau et al. |
| 6,675,809 B2 | 1/2004 | Stack et al. |
| 6,685,620 B2 | 2/2004 | Gifford, III et al. |
| 6,702,763 B2 | 3/2004 | Murphy et al. |
| 6,702,844 B2 | 3/2004 | Lazarus |
| 6,719,174 B1 | 4/2004 | Swift |
| 6,730,119 B1 | 5/2004 | Smalling |
| 6,746,460 B2 | 6/2004 | Gannoe et al. |
| 6,800,081 B2 | 10/2004 | Parodi |
| 6,878,164 B2 | 4/2005 | Kujawski et al. |
| 6,929,661 B2 | 8/2005 | Bolduc et al. |
| 6,960,217 B2 | 11/2005 | Bolduc |
| 6,984,241 B2 | 1/2006 | Lubbers et al. |
| 6,986,784 B1 | 1/2006 | Weiser et al. |
| 7,033,384 B2 | 4/2006 | Gannoe et al. |
| 7,037,343 B2 | 5/2006 | Imran |
| 7,060,023 B2 | 6/2006 | French et al. |
| 7,081,086 B2 | 7/2006 | Lau et al. |
| 7,081,129 B2 | 7/2006 | Chobotov |
| 7,128,754 B2 | 10/2006 | Bolduc |
| 7,155,295 B2 | 12/2006 | Lau et al. |
| 7,179,225 B2 | 2/2007 | Shluzas et al. |
| 7,306,623 B2 | 12/2007 | Watson |
| 7,361,137 B2 | 4/2008 | Taylor et al. |
| 7,422,558 B2 | 9/2008 | Lau et al. |
| 7,491,232 B2 | 2/2009 | Bolduc et al. |
| 7,544,198 B2 | 6/2009 | Parodi |
| 7,591,842 B2 | 9/2009 | Parodi |
| 7,637,932 B2 | 12/2009 | Bolduc et al. |
| 7,727,189 B2 | 6/2010 | Vantassel et al. |
| 7,823,267 B2 | 11/2010 | Bolduc |
| 7,828,838 B2 | 11/2010 | Bolduc et al. |
| 7,959,663 B2 | 6/2011 | Bolduc |
| 8,075,570 B2 | 12/2011 | Bolduc et al. |
| 8,083,752 B2 | 12/2011 | Bolduc |
| 8,092,519 B2 | 1/2012 | Bolduc |
| 2002/0026144 A1 | 2/2002 | Patterson |
| 2002/0029077 A1 | 3/2002 | Leopold et al. |
| 2002/0058855 A1 | 5/2002 | Cyril, Jr. et al. |
| 2002/0065485 A1 | 5/2002 | DuBois et al. |
| 2002/0099432 A1 | 7/2002 | Yee |
| 2002/0133054 A1 | 9/2002 | Murphy et al. |
| 2002/0156365 A1 | 10/2002 | Tsekos |
| 2003/0018358 A1 | 1/2003 | Saadat |
| 2003/0100943 A1 | 5/2003 | Bolduc |
| 2003/0149463 A1 | 8/2003 | Solymar et al. |
| 2003/0158570 A1 | 8/2003 | Ferrazzi |
| 2003/0163085 A1 | 8/2003 | Tanner et al. |
| 2003/0204249 A1 | 10/2003 | Letort |
| 2003/0233140 A1 | 12/2003 | Hartley et al. |
| 2004/0002731 A1 | 1/2004 | Aganon et al. |
| 2004/0039405 A1 | 2/2004 | Petrovic et al. |
| 2004/0054352 A1 | 3/2004 | Adams et al. |
| 2004/0093057 A1 | 5/2004 | Bolduc et al. |
| 2004/0127916 A1 | 7/2004 | Bolduc et al. |
| 2004/0138734 A1 | 7/2004 | Chobotov et al. |
| 2004/0206363 A1 | 10/2004 | Mccarthy et al. |
| 2004/0210304 A1 | 10/2004 | Seguin et al. |
| 2004/0243170 A1 | 12/2004 | Suresh et al. |
| 2004/0260322 A1 | 12/2004 | Rudko et al. |
| 2004/0260383 A1 | 12/2004 | Stelter et al. |
| 2005/0038506 A1 | 2/2005 | Webler et al. |
| 2005/0043790 A1 | 2/2005 | Seguin |
| 2005/0070992 A1 | 3/2005 | Bolduc et al. |
| 2005/0113906 A9 | 5/2005 | Bolduc et al. |
| 2005/0187613 A1 | 8/2005 | Bolduc |
| 2005/0197716 A1 | 9/2005 | Sharkey et al. |
| 2005/0240258 A1 | 10/2005 | Bolduc et al. |
| 2005/0240260 A1 | 10/2005 | Bolduc |
| 2006/0100640 A1 | 5/2006 | Bolduc et al. |
| 2006/0259125 A1 | 11/2006 | Peacock, III |
| 2007/0021753 A1 | 1/2007 | Bolduc et al. |
| 2007/0021829 A1 | 1/2007 | Bolduc et al. |
| 2007/0032860 A1 | 2/2007 | Brooks et al. |
| 2007/0073389 A1 | 3/2007 | Bolduc et al. |
| 2008/0065117 A1 | 3/2008 | Bolduc et al. |
| 2008/0065189 A1 | 3/2008 | Bolduc |
| 2008/0065191 A1 | 3/2008 | Bolduc et al. |
| 2008/0097489 A1 | 4/2008 | Goldfarb et al. |
| 2008/0132996 A1 | 6/2008 | Drasler et al. |
| 2009/0082852 A1 | 3/2009 | Bolduc et al. |
| 2009/0099650 A1 | 4/2009 | Bolduc et al. |
| 2009/0112303 A1 | 4/2009 | Bolduc |
| 2010/0094400 A1 | 4/2010 | Bolduc et al. |
| 2012/0065661 A1 | 3/2012 | Bolduc |

FOREIGN PATENT DOCUMENTS

| | | |
|---|---|---|
| AU | 2008243229 A1 | 12/2008 |
| AU | 2004287355 B2 | 6/2011 |
| AU | 2006305688 B2 | 12/2012 |
| CA | 2265131 A1 | 9/1999 |
| CA | 2344252 A1 | 3/2000 |
| CA | 2729464 A1 | 6/2003 |
| CA | 2626505 A1 | 4/2007 |
| CA | 2626106 A1 | 5/2007 |
| CA | 2625082 A1 | 7/2008 |
| CA | 2740831 A1 | 4/2010 |
| CA | 2464048 A1 | 6/2010 |
| CA | 2464900 A1 | 4/2011 |
| CA | 2546721 C | 9/2013 |
| CN | 1019461 B | 12/1992 |
| CN | 1422139 A | 6/2003 |
| CN | 1596087 A | 3/2005 |
| CN | 1596088 A | 3/2005 |
| CN | 1856280 A | 11/2006 |
| CN | 1870949 A | 11/2006 |
| CN | 1870951 A | 11/2006 |
| CN | 1997318 A | 7/2007 |
| CN | 101151002 A | 3/2008 |
| CN | 101267788 A | 9/2008 |
| CN | 101330882 A | 12/2008 |
| CN | 101352375 A | 1/2009 |
| CN | 101360466 A | 2/2009 |
| CN | 101460104 A | 6/2009 |
| CN | 101466316 A | 6/2009 |
| CN | 100525719 C | 8/2009 |
| CN | 101330882 B | 4/2011 |

(56) References Cited

FOREIGN PATENT DOCUMENTS

| | | |
|---|---|---|
| CN | 101466316 B | 6/2012 |
| DE | 33 33 427 C2 | 5/1991 |
| DE | 69228184 T2 | 9/1999 |
| DE | 10034105 C1 | 4/2002 |
| DE | 10297483 T5 | 12/2004 |
| EP | 0 321 912 A1 | 6/1989 |
| EP | 0 663 184 A1 | 7/1995 |
| EP | 0 835 642 B1 | 8/2002 |
| EP | 1 369 098 A1 | 12/2003 |
| EP | 1 440 673 A1 | 7/2004 |
| EP | 1675528 A2 | 7/2006 |
| EP | 1725172 A2 | 11/2006 |
| EP | 1734872 A1 | 12/2006 |
| EP | 1948080 A2 | 7/2008 |
| EP | 2119416 A1 | 11/2009 |
| EP | 2349086 A1 | 8/2011 |
| EP | 2349087 A1 | 8/2011 |
| FR | 2299548 A1 | 8/1976 |
| GB | 2396824 A | 7/2004 |
| GB | 2417208 A | 2/2006 |
| HK | 1073240 A1 | 8/2009 |
| JP | 2001509398 A | 7/2001 |
| JP | 2001522292 A | 11/2001 |
| JP | 2002526193 A | 8/2002 |
| JP | 2005046648 A | 2/2005 |
| JP | 2005510293 A | 4/2005 |
| JP | 2005510303 A | 4/2005 |
| JP | 2007508894 A | 4/2007 |
| JP | 2007508895 A | 4/2007 |
| JP | 2007523694 A | 8/2007 |
| JP | 2007535339 A | 12/2007 |
| JP | 2009512497 A | 3/2009 |
| JP | 2009512498 A | 3/2009 |
| JP | 2009512499 A | 3/2009 |
| JP | 2009078172 A | 4/2009 |
| JP | 2009095684 A | 5/2009 |
| JP | 2009106763 A | 5/2009 |
| JP | 2009106768 A | 5/2009 |
| JP | 2009106775 A | 5/2009 |
| JP | 2009112827 A | 5/2009 |
| JP | 2009519046 A | 5/2009 |
| JP | 4405262 B2 | 1/2010 |
| JP | 10506026 A | 2/2010 |
| JP | 2010051786 A | 3/2010 |
| JP | 4465359 B2 | 5/2010 |
| JP | 2011062570 A | 3/2011 |
| JP | 4699445 B2 | 6/2011 |
| WO | WO-93/00868 A1 | 1/1993 |
| WO | WO-95/21592 A1 | 8/1995 |
| WO | WO-96/03925 A1 | 2/1996 |
| WO | WO-97/03616 A1 | 2/1997 |
| WO | WO-9703616 A1 | 2/1997 |
| WO | WO-9712562 A1 | 4/1997 |
| WO | WO-9717039 A1 | 5/1997 |
| WO | WO-9717913 A1 | 5/1997 |
| WO | WO-98/53761 A1 | 12/1998 |
| WO | WO-9930637 A1 | 6/1999 |
| WO | WO-9933402 A1 | 7/1999 |
| WO | WO-9933402 A9 | 9/1999 |
| WO | WO-99/53845 A1 | 10/1999 |
| WO | WO-9953845 A1 | 10/1999 |
| WO | WO-00/16701 A1 | 3/2000 |
| WO | WO-00/35350 A1 | 6/2000 |
| WO | WO-00/64357 A1 | 11/2000 |
| WO | WO-0160432 A1 | 8/2001 |
| WO | WO-03032870 A1 | 4/2003 |
| WO | WO-03/045283 A1 | 6/2003 |
| WO | WO-03/045467 A2 | 6/2003 |
| WO | WO-03/045467 A3 | 6/2003 |
| WO | WO-03/079935 A1 | 10/2003 |
| WO | WO-2005/032333 A2 | 4/2005 |
| WO | WO-2005/032333 A3 | 4/2005 |
| WO | WO-2005037076 A2 | 4/2005 |
| WO | WO-2005/044073 A2 | 5/2005 |
| WO | WO-2005/044073 A3 | 5/2005 |
| WO | WO-2005044148 A1 | 5/2005 |
| WO | WO-2005067660 A2 | 7/2005 |
| WO | WO-2005/081936 A2 | 9/2005 |
| WO | WO-2005/081936 A3 | 9/2005 |
| WO | WO-2005102181 A1 | 11/2005 |
| WO | WO-2007/046953 A2 | 4/2007 |
| WO | WO-2007/046953 A3 | 4/2007 |
| WO | WO-2007/046954 A2 | 4/2007 |
| WO | WO-2007/046954 A3 | 4/2007 |
| WO | WO-2007/046955 A2 | 4/2007 |
| WO | WO-2007/046955 A3 | 4/2007 |
| WO | WO-2007/047023 A2 | 4/2007 |
| WO | WO-2007/047023 A3 | 4/2007 |
| WO | WO-2005067660 A3 | 4/2007 |
| WO | WO-2007053233 A2 | 5/2007 |
| WO | WO-2007053233 A3 | 1/2008 |
| WO | WO-2010/044851 A1 | 4/2010 |
| WO | WO-2010/044856 A1 | 4/2010 |
| WO | WO-2010044854 A1 | 4/2010 |
| WO | WO-2010044855 A1 | 4/2010 |

OTHER PUBLICATIONS

Hatchett, R.L. et al. (1995). "Extraperitoneal Endoscopic Burch Repair Using a Tacker Mesh Technique," *Circa* pp. 1-4.
Medical Technologies. (Oct. 1995). "Laparoscopic Surgery," *Medical Data International, Inc. MedPro*, p. 190.
Newman, L. et al. (1995). "Tacker-Assisted TAPP Procedure," *Circa*, 2 pages.
Non Final Office Action mailed on May 18, 2004, for U.S. Appl. No. 10/271,334, filed Oct. 15, 2002, 8 pages.
Examiner's Interview Summary mailed Feb. 11, 2005, for U.S. Appl. No. 10/271,334, filed Oct. 15, 2002, 1 page.
Notice of Allowability mailed on Feb. 11, 2005, for U.S. Appl. No. 10/271,334, filed Oct. 15, 2002, 4 pages.
Notice of Allowance mailed on Mar. 17, 2005, for U.S. Appl. No. 10/271,334, filed Oct. 15, 2002, 3 pages.
Notice of Allowance mailed on Aug. 26, 2005, for U.S. Appl. No. 10/271,334, filed Oct. 15, 2002, 3 pages.
Non Final Office Action mailed on May 30, 2012, for U.S. Appl. No. 12/653,219, filed Dec. 10, 2009, 16 pages.
Non Final Office Action mailed on May 5, 2009, for U.S. Appl. No. 11/166,411, filed Jun. 24, 2005, 7 pages.
Final Office Action mailed on Dec. 3, 2009, for U.S. Appl. No. 11/166,411, filed Jun. 24, 2005, 5 pages.
Notice of Allowance mailed on Jan. 6, 2011, for U.S. Appl. No. 11/166,411, filed Jun. 24, 2005, 4 pages.
Notice of Allowance mailed on Aug. 23, 2011, for U.S. Appl. No. 11/166,411, filed Jun. 24, 2005, 5 pages.
Non-Final Office Action mailed on Oct. 6, 2008, for U.S. Appl. No. 11/540,427, filed Sep. 29, 2006, 9 pages.
Final Office Action mailed on Jul. 21, 2009, for U.S. Appl. No. 11/540,427, filed Sep. 29, 2006, 8 pages.
Notice of Allowance mailed on Apr. 29, 2011, for U.S. Appl. No. 11/540,427, filed Sep. 29, 2006, 8 pages.
Non-Final Office Action mailed on Nov. 12, 2010, for U.S. Appl. No. 11/540,428, filed Sep. 29, 2006, 7 pages.
Final Office Action mailed on Aug. 4, 2011, for U.S. Appl. No. 11/540,428, filed Sep. 29, 2006, 9 pages.
Non-Final Office Action mailed on May 20, 2010, for U.S. Appl. 11/978,752, filed Oct. 30, 2007, 5 pages.
Final Office Action mailed Dec. 22, 2010, for U.S. Appl. 11/978,752, filed Oct. 30, 2007, 6 pages.
Notice of Allowance mailed on Aug. 31, 2011, for U.S. Appl. No. 11/978,752, filed Oct. 30, 2007, 5 pages.
Non-Final Office Action mailed on Sep. 3, 2010, for U.S. Appl. No. 11/978,753, filed Oct. 30, 2007, 7 pages.
Final Office Action mailed on May 2, 2011, for U.S. Appl. No. 11/978,753, filed Oct. 30, 2007, 8 pages.
Non-Final Office Action mailed on Oct. 6, 2011, for U.S. Appl. No. 12/315,015, filed Nov. 26, 2008, 10 pages.
Non-Final Office Action mailed on Mar. 13, 2006, for U.S. Appl. No. 10/307,226, filed Nov. 29, 2002, 6 pages.
Final Office Action mailed on Dec. 12, 2006, for U.S. Appl. No. 10/307,226, filed Nov. 29, 2002, 5 pages.

(56) References Cited

OTHER PUBLICATIONS

Non-Final Office Action mailed on Jun. 12, 2007, for U.S. Appl. No. 10/307,226, filed Nov. 29, 2002, 5 pages.
Final Office Action mailed on Jun. 27, 2008, for U.S. Appl. No. 10/307,226, filed Nov. 29, 2002, 5 pages.
Non-Final Office Action mailed on Sep. 9, 2009, for U.S. Appl. No. 10/307,226, filed Nov. 29, 2002, 6 pages.
Non-Final Office Action mailed on Jan. 27, 2006, for U.S. Appl. No. 10/669,881, filed Sep. 24, 2003, 5 pages.
Final Office Action mailed Jan. 25, 2008, for U.S. Appl. No. 10/669,881, filed Sep. 24, 2003, 7 pages.
Notice of Allowance mailed Oct. 8, 2008, for U.S. Appl. No. 10/669,881, filed Sep. 24, 2003, 6 pages.
Notice of Allowance mailed on Mar. 9, 2010, for U.S. Appl. No. 11/254,444, filed Oct. 20, 2005, 6 pages.
Notice of Allowance mailed on Jun. 29, 2010, for U.S. Appl. No. 11/254,444, filed Oct. 20, 2005, 6 pages.
Non-Final Office Action mailed on Oct. 1, 2009, for U.S. Appl. No. 11/254,619, filed Oct. 20, 2005, 5 pages.
Final Office Action mailed on Jun. 30, 2010, for U.S. Appl. No. 11/254,619, filed Oct. 20, 2005, 10 pages.
Non-Final Office Action mailed on Feb. 3, 2011, for U.S. Appl. No. 11/254,619, filed Oct. 20, 2005, 8 pages.
Final Office Action mailed on Oct. 20, 2011, for U.S. Appl. No. 11/254,619, filed Oct. 20, 2005, 11pages.
Non-Final Office Action mailed on Mar. 30, 2009, for U.S. Appl. No. 11/254,950, filed Oct. 20, 2005, 5 pages.
Notice of Allowance mailed on Feb. 26, 2010, for U.S. Appl. No. 11/254,950, filed Oct. 20, 2005, 4 pages.
Notice of Allowance mailed on Jun. 22, 2010, for U.S. Appl. No. 11/254,950, filed Oct. 20, 2005, 4 pages.
Non-Final Office Action mailed on May 14, 2008, for U.S. Appl. No. 11/255,116, filed Oct. 20, 2005, 14 pages.
Notice of Allowance mailed on Aug. 10, 2009, for U.S. Appl. No. 11/255,116, filed Oct. 20, 2005, 4 pages.
Non-Final Office Action mailed on Jul. 23, 2007, for U.S. Appl. No. 10/786,465, filed Feb. 25, 2004, 6 pages.
Final Office Action mailed on Jan. 21, 2009, for U.S. Appl. No. 10/786,465, filed Feb. 25, 2004, 7 pages.
Non-Final Office Action mailed on Mar. 26, 2010, for U.S. Appl. No. 10/786,465, filed Feb. 25, 2004, 7 pages.
Notice of Allowance mailed on Mar. 14, 2012, for U.S. Appl. No. 10/786,465, filed Feb. 25, 2004, 6 pages.
Non-Final Office Action mailed Sep. 1, 2010, for U.S. Appl. No. 11/488,305, filed Jul. 18, 2006, 7 pages.
Final Office Action mailed on Apr. 13, 2011, for U.S. Appl. No. 11/488,305, filed Jul. 18, 2006, 8 pages.
Non-Final Office Action mailed on Oct. 31, 2011, for U.S. Appl. No. 11/488,305, filed Jul. 18, 2006, 6 pages.
International Search Report mailed on Mar. 6, 2003, for PCT Patent Application No. PCT/US02/32753, filed on Oct. 15, 2002, one page.
Written Opinion mailed on Aug. 26, 2003, for PCT Patent Application No. PCT/US02/32753, filed on Oct. 15, 2002, 4 pages.
International Preliminary Report on Patentability mailed on Sep. 1, 2004, for PCT Patent Application No. PCT/US02/32753, filed on Oct. 15, 2002, 3 pages.
International Search Report mailed on May 8, 2003, for PCT Patent Application No. PCT/US02/38365, filed on Nov. 29, 2002, 4 pages.
Written Opinion mailed on Oct. 27, 2003, for PCT Patent Application No. PCT/US02/38365, filed on Nov. 29, 2002, 4 pages.
International Preliminary Report on Patentability mailed on Mar. 1, 2004, for PCT Patent Application No. PCT/US02/38365, filed on Nov. 29, 2002, 3 pages.
International Search Report mailed on Feb. 24, 2006, for PCT Patent Application No. PCT/US2004/029402, filed on Sep. 10, 2004, 3 pages.
Written Opinion mailed on Feb. 24, 2006, for PCT Patent Application No. PCT/US2004/029402, filed on Sep. 10, 2004, 3 pages.
International Preliminary Report on Patentability mailed on Jul. 10, 2006, for PCT Patent Application No. PCT/US2004/029402, filed on Sep. 10, 2004, 3 pages.
International Search Report mailed on Mar. 30, 2007, for PCT Patent Application No. PCT/US2006/033741, filed on Aug. 29, 2006, 2 pages.
Written Opinion mailed on Mar. 30, 2007, for PCT Patent Application No. PCT/US2006/033741, filed on Aug. 29, 2006, 4 pages.
International Preliminary Examination Report mailed on Jul. 28, 2007, for PCT Patent Application No. PCT/US2006/033741, filed on Aug. 29, 2006, 5 pages.
International Search Report mailed on Aug. 15, 2007, for PCT Patent Application No. PCT/US06/033749, filed on Aug. 29, 2006, 3 pages.
Written Opinion mailed on Aug. 15, 2007, for PCT Patent Application No. PCT/US06/033749, filed on Aug. 29, 2006, 5 pages.
International Preliminary Report on Patentability mailed on Jun. 18, 2008, for PCT Patent Application No. PCT/US06/033749, filed on Aug. 29, 2006, 6 pages.
International Search Report mailed on Jul. 8, 2008, for PCT Patent Application No. PCT/US2006/033747, filed on Aug. 29, 2006, 2 pages.
Written Opinion mailed on Jul. 8, 2008, for PCT Patent Application No. PCT/US2006/033747, filed on Aug. 29, 2006, 3 pages.
International Search Report mailed on Sep. 25, 2007, PCT Patent Application No. PCT/US05/005627, filed Feb. 22, 2005, 3 pages.
Written Opinion mailed on Sep. 25, 2007, PCT Patent Application No. PCT/US05/005627, filed Feb. 22, 2005, 3 pages.
International Preliminary Examination Report mailed on Apr. 7, 2009, PCT Patent Application No. PCT/US05/005627, filed Feb. 22, 2005, 5 pages.
International Search Report mailed on Aug. 30, 2007, for PCT/US2006/037085, filed on Sep. 22, 2006, one page.
Written Opinion mailed on Aug. 30, 2007, for PCT/US2006/037085, filed on Sep. 22, 2006, 7 pages.
International Preliminary Report on Patentability mailed on Jul. 24, 2008, for PCT/US2006/037085, filed on Sep. 22, 2006, 9 pages.
International Search Report mailed on Dec. 11, 2009, for PCT/US2009/005604, filed on Oct. 14, 2009, 3 pages.
Written Opinion mailed on Dec. 11, 2009, for PCT/US2009/005604, filed on Oct. 14, 2009, 7 pages.
International Search Report mailed on Dec. 18, 2009, for PCT/US2009/005609, filed Oct. 14, 2009, 3 pages.
Written Opinion mailed on Dec. 18, 2009, for PCT/US2009/005609, filed Oct. 14, 2009, 6 pages.
Anonymous. (1995). "5mm Origin Tacker™ It Runs in Circles Around Staples," *Guidant Origin Advertising Literature*, 2 pages.
"U.S. Appl. No. 10/271,334, Examiner Interview Summary mailed Feb. 11, 2005", 2 pgs.
"U.S. Appl. No. 10/271,334, Response filed Nov. 22, 2004 to Non Final Office Action mailed May 18, 2004", 6 pgs.
"U.S. Appl. No. 10/692,282, Non Final Office Action mailed Aug. 30, 2005", 6 pgs.
"U.S. Appl. No. 10/692,282, Notice of Allowance mailed Jun. 13, 2006", 6 pgs.
"U.S. Appl. No. 10/692,282, Response filed Feb. 28, 2006 to Non Final Office Action mailed Aug. 30, 2005", 5 pgs.
"U.S. Appl. No. 10/693,255, Examiner Interview Summary mailed Feb. 17, 2005", 3 pgs.
"U.S. Appl. No. 10/693,255, Non Final Office Action mailed Dec. 9, 2004", 6 pgs.
"U.S. Appl. No. 10/693,255, Notice of Allowance mailed Mar. 9, 2005", 9 pgs.
"U.S. Appl. No. 10/693,255, Response filed Feb. 17, 2005 to Non Final Office Action mailed Dec. 9, 2004", 6 pgs.
"U.S. Appl. No. 10/752,435, Final Office Action mailed May 14, 2010", 8 pgs.
"U.S. Appl. No. 10/752,435, Final Office Action mailed Jul. 12, 2007", 8 pgs.
"U.S. Appl. No. 10/752,435, Final Office Action mailed Dec. 8, 2008", 8 pgs.
"U.S. Appl. No. 10/752,435, Non Final Office Action mailed Mar. 18, 2008", 7 pgs.

(56) References Cited

OTHER PUBLICATIONS

"U.S. Appl. No. 10/752,435, Non Final Office Action mailed Jul. 21, 2009", 7 pgs.
"U.S. Appl. No. 10/752,435, Non Final Office Action mailed Oct. 19, 2006", 17 pgs.
"U.S. Appl. No. 11/166,411, Final Office Action mailed Dec. 3, 2009", 5 pgs.
"U.S. Appl. No. 11/166,428, Final Office Action mailed Jan. 12, 2009", 10 pgs.
"U.S. Appl. No. 11/166,428, Final Office Action mailed Mar. 16, 2010", 8 pgs.
"U.S. Appl. No. 11/166,428, Non Final Office Action mailed May 14, 2008", 6 pgs.
"U.S. Appl. No. 11/166,428, Non Final Office Action mailed Jun. 16, 2009", 10 pgs.
"U.S. Appl. No. 11/254,619, Response filed Apr. 1, 2010 to Non Final Office Action mailed Oct. 1, 2009", 5 pgs.
"U.S. Appl. No. 11/254,619, Response filed Apr. 20, 2012 to Final Office Action mailed Oct. 20, 2011", 11 pgs.
"U.S. Appl. No. 11/254,619, Response filed Aug. 3, 2011 to Non Final Office Action mailed Feb. 3, 2011", 13 pgs.
"U.S. Appl. No. 11/254,619, Response filed Dec. 29, 2010 to Final Office Action mailed Jun. 30, 2010", 12 pgs.
"U.S. Appl. No. 11/580,584, Appeal Brief filed Nov. 15, 2010", 11 pgs.
"U.S. Appl. No. 11/580,584, Final Office Action mailed Jan. 22, 2009", 9 pgs.
"U.S. Appl. No. 11/580,584, Final Office Action mailed Oct. 16, 2009", 8 pgs.
"U.S. Appl. No. 11/580,584, Non Final Office Action mailed Apr. 18, 2008", 6 pgs.
"U.S. Appl. No. 11/580,584, Notice of Allowance mailed Feb. 4, 2011", 7 pgs.
"U.S. Appl. No. 11/580,584, Response filed Jul. 22, 2009 to Final Office Action mailed Jan. 22, 2009", 6 pgs.
"U.S. Appl. No. 11/580,584, Response filed Oct. 20, 2008 to Non Final Office Action mailed Apr. 18, 2008", 5 pgs.
"U.S. Appl. No. 11/981,112, Final Office Action mailed Apr. 29, 2010", 9 pgs.
"U.S. Appl. No. 11/981,112, Non Final Office Action mailed Jul. 8, 2009", 11 pgs.
"U.S. Appl. No. 12/288,031, Non Final Office Action mailed May 10, 2012", 8 pgs.
"U.S. Appl. No. 12/288,031, Response filed Mar. 25, 2013 to Final Office Action mailed Jan. 3, 2013", 11 pgs.
"U.S. Appl. No. 12/288,031, Response filed Apr. 4, 2012 to Restriction Requirement mailed Nov. 4, 2011", 3 pgs.
"U.S. Appl. No. 12/288,031, Response filed Oct. 10, 2012 to Non Final Office Action mailed May 10, 2012", 11 pgs.
"U.S. Appl. No. 12/288,031, Restriction Requirement mailed Nov. 4, 2011", 9 pgs.
"U.S. Appl. No. 12/288,034, Non Final Office Action mailed Jun. 22, 2012", 7 pgs.
"U.S. Appl. No. 12/288,034, Response filed May 1, 2012 to Restriction Requirement mailed Nov. 3, 2011", 4 pgs.
"U.S. Appl. No. 12/288,034, Response filed Dec. 21, 2012 to Non Final Office Action mailed Jun. 22, 2012", 12 pgs.
"U.S. Appl. No. 12/288,034, Restriction Requirement mailed Nov. 3, 2011", 9 pgs.
"U.S. Appl. No. 12/315,015, Advisory Action mailed Sep. 12, 2012", 3 pgs.
"U.S. Appl. No. 12/315,015, Final Office Action mailed Apr. 26, 2012", 7 pgs.
"U.S. Appl. No. 12/315,015, Preliminary Amendment filed Mar 10, 2009", 3 pgs.
"U.S. Appl. No. 12/315,015, Response filed Apr. 6, 2012 to Non Final Office Action mailed Oct. 6, 2011", 12 pgs.
"U.S. Appl. No. 12/315,015, Response filed Aug. 27, 2012 to Final Office Action mailed Apr. 26, 2012", 6 pgs.
"U.S. Appl. No. 13/162,384, Preliminary Amendment filed Jun. 16, 2011", 7 pgs.
"U.S. Appl. No. 13/291,942, Preliminary Amendment filed Nov. 8, 2011", 3 pgs.
"U.S. Appl. No. 13/495,836, Non Final Office Action mailed Aug. 5, 2013", 7 pgs.
"U.S. Appl. No. 13/495,836, Preliminary Amendment filed Jun. 13, 2012", 8 pgs.
"U.S. Appl. No. 13/495,836, Response filed Mar. 25, 2013 to Non Final Office Action mailed Dec. 26, 2012", 9 pgs.
"Australian Application Serial No. 2002353807, First Examiner Report mailed Nov. 16, 2006", 2 pgs.
"Australian Application Serial No. 2004277897, First Examiner Report mailed Oct. 14, 2009", 2 pgs.
"Australian Application Serial No. 2004277897, Response filed Jul. 14, 2011 to First Examiner Report mailed Oct. 14, 2009", 9 pgs.
"Australian Application Serial No. 2005235108, Office Action mailed Feb. 26, 2010", 3 pgs.
"Australian Application Serial No. 2006305688, First Examiner Report mailed 03-10-11", 3 pgs.
"Australian Application Serial No. 2006305688, Response filed Oct. 22, 2012 to First Examiner Report mailed Mar. 10, 2011", 16 pgs.
"Australian Application Serial No. 2008243229, First Examiner Report mailed Apr. 13, 2010", 2 pgs.
"Australian Application Serial No. 2008243229, Response filed May 13, 2011 to Office Action mailed Apr. 13, 2010", 15 pgs.
"Australian Application Serial No. 2011253682, Response filed Jul. 17, 2013 to Office Action mailed Sep. 27, 2012", 19 pgs.
"Canadian Application Serial No. 2,539,585, Office Action mailed Sep. 19, 2012", 2 pgs.
"Canadian Application Serial No. 2,554,022, Office Action mailed Jun. 22, 2011", 3 pgs.
"Canadian Application Serial No. 2,554,022, Office Action mailed Aug. 31, 2010", 2 pgs.
"Canadian Application Serial No. 2,558,317, Office Action mailed Aug. 31, 2010", 2 pgs.
"Canadian Application Serial No. 2,558,317, Office Action mailed Sep. 28, 2011", 3 pgs.
"Chinese Application Serial No. 200480027649.7, Office Action mailed Jun. 23, 2008", w/English translation, 5 pgs.
"Chinese Application Serial No. 200480027649.7, Office Action mailed Sep. 4, 2009", w/English translation, 18 pgs.
"Chinese Application Serial No. 200480027649.7, Office Action mailed Dec. 24, 2010", w/English translation, 6 pgs.
"Chinese Application Serial No. 200480027649.7, Response filed Mar. 8, 2011 to Office Action mailed Dec. 24, 2010", w/English translation, 7 pgs.
"Chinese Application Serial No. 200580006169.7, Office Action mailed Mar. 1, 2010", w/English translation, 12 pgs.
"Chinese Application Serial No. 200580006169.7, Response filed Jul. 14, 2010 to Office Action mailed Mar. 1, 2010", w/English translation, 32 pgs.
"Chinese Application Serial No. 200680034052.4, Office Action mailed May 11, 2010", w/English translation, 7 pgs.
"Chinese Application Serial No. 200680034052.4, Office Action mailed Aug. 14, 2009", w/English translation, 13 pgs.
"Chinese Application Serial No. 200910139527.1, Office Action mailed Jul. 12, 2010", w/English translation, 9 pgs.
"European Application Serial No. 04788653.6, Office Action mailed May 19, 2006", 2 pgs.
"European Application Serial No. 05713941.2, Office Action mailed Dec. 13, 2007", 2 pgs.
"European Application Serial No. 06802573.3, Extended European Search Report mailed Feb. 15, 2012", 6 pgs.
"European Application Serial No. 06802573.3, Office Action mailed Mar. 5, 2012", 1 pg.
"European Application Serial No. 06802573.3, Office Action mailed May 28, 2008", 2 pgs.
"European Application Serial No. 06802573.3, Response filed Sep. 3, 2012 to Office Action mailed Mar. 5, 2012", 15 pgs.
"European Application Serial No. 06802580.8, Office Action mailed Feb. 25, 2013", 3 pgs.

(56) References Cited

OTHER PUBLICATIONS

"European Application Serial No. 09075319.5, Extended European Search Report mailed Oct. 14, 2009", 6 pgs.
"European Application Serial No. 09075319.5, Office Action mailed Jan. 14, 2010", 1 pgs.
"European Application Serial No. 09075319.5, Office Action mailed Oct. 14, 2010", 4 pgs.
"European Application Serial No. 09820886.1, Office Action mailed Jun. 7, 2011", 2 pgs.
"European Application Serial No. 09820886.1, Response filed Dec. 8, 2011 to Office Action mailed Jun. 7, 2011", 3 pgs.
"European Application Serial No. 09820891.1, Office Action mailed Jun. 7, 2011", 2 pgs.
"European Application Serial No. 09820891.1, Response filed Dec. 8, 2011 to Office Action mailed Jun. 7, 2011", 2 pgs.
"European Application Serial No. 09075319.5, Response filed Feb. 21, 2011 to Office Action mailed Oct. 14, 2010", 5 pgs.
"European Application Serial No. 09075319.5, Response filed Jul. 20, 2010 to Office Action mailed Jan. 14, 2010", 13 pgs.
"International Application Serial No. PCT/US2002/038365, International Preliminary Examination Report mailed May 8, 2003", 3 pgs.
"International Application Serial No. PCT/US2004/027589, International Preliminary Report on Patentability mailed Apr. 6, 2005", 4 pgs.
"International Application Serial No. PCT/US2004/027589, International Search Report mailed Apr. 6, 2005", 1 pg.
"International Application Serial No. PCT/US2004/027589, Written Opinion mailed Apr. 6, 2005", 3 pgs.
"International Application Serial No. PCT/US2004/027590, International Preliminary Examination Report mailed Feb. 16, 2006", 3 pgs.
"International Application Serial No. PCT/US2004/027590, International Search Report mailed Jan. 12, 2005", 1 pg.
"International Application Serial No. PCT/US2004/027590, Written Opinion mailed Jan. 12, 2005", 3 pgs.
"International Application Serial No. PCT/US2005/000059, International Preliminary Report on Patentability mailed May 18, 2007", 8 pgs.
"International Application Serial No. PCT/US2005/000059, International Search Report mailed Jan. 5, 2007", 3 pgs.
"International Application Serial No. PCT/US2005/000059, Written Opinion mailed Jan. 5, 2007", 8 pgs.
"International Application Serial No. PCT/US2006/033747, International Preliminary Report on Patentability mailed Mar. 1, 2011", 4 pgs.
"International Application Serial No. PCT/US2006/033748, International Preliminary Report on Patentability mailed Jun. 18, 2008", 7 pgs.
"International Application Serial No. PCT/US2006/033748, International Search Report mailed Aug. 15, 2007", 1 pg.
"International Application Serial No. PCT/US2006/033748, Written Opinion mailed Aug. 15, 2007", 5 pgs.
"International Application Serial No. PCT/US2006/037085, International Preliminary Report on Patentability mailed Aug. 20, 2007", 10 pgs.
"International Application Serial No. PCT/US2009/005604, International Preliminary Report on Patentability mailed Jan. 13, 2011", 10 pgs.
"International Application Serial No. PCT/US2009/005607, International Preliminary Report on Patentability mailed Jan. 9, 2011", 9 pgs.
"International Application Serial No. PCT/US2009/005607, International Search Report mailed Dec. 11, 2009", 2 pgs.
"International Application Serial No. PCT/US2009/005607, Written Opinion mailed Dec. 11, 2009", 6 pgs.
"International Application Serial No. PCT/US2009/005608, International Preliminary Report on Patentability mailed Jan. 14, 2011", 7 pgs.
"International Application Serial No. PCT/US2009/005608, International Search Report mailed Dec. 10, 2009", 2 pgs.
"International Application Serial No. PCT/US2009/005608, Written Opinion mailed Dec. 10, 2009", 4 pgs.
"International Application Serial No. PCT/US2009/005609, International Preliminary Report on Patentability mailed Jan. 9, 2011", 9 pgs.
"Japanese Application Serial No. 2003-546789, Office Action mailed Feb. 26, 2009", w/English translation, 7 pgs.
"Japanese Application Serial No. 2003-546789, Office Action mailed Jun. 17, 2008", w/English translation, 6 pgs.
"Japanese Application Serial No. 2003-546789, Response filed Dec. 11, 2008 to Office Action mailed Jun. 17, 2008", w/English translation, 9 pgs.
"Japanese Application Serial No. 2006-528036, Office Action mailed Feb. 26, 2009", w/English translation, 5 pgs.
"Japanese Application Serial No. 2006-528036, Office Action mailed Jun. 23, 2008", w/English translation, 5 pgs.
"Japanese Application Serial No. 2006-528036, Response filed Dec. 25, 2008 to Office Action mailed Jun. 23, 2008", w/English translation, 9 pgs.
"Japanese Application Serial No. 2007500928, Office Action mailed Jul. 1, 2010", w/English translation, 10 pgs.
"Japanese Application Serial No. 2007504965, Office Action mailed Mar. 7, 2012", w/English translation, 4 pgs.
"Japanese Application Serial No. 2007504965, Office Action mailed Jun. 14, 2011", w/English translation, 4 pgs.
"Japanese Application Serial No. 2007504965, Office Action mailed Sep. 14, 2010", English translation, 1 pg.
"Japanese Application Serial No. 2008-536577, Office Action mailed Jul. 8, 2011", w/English translation, 4 pgs.
"U.S. Appl. No. 10/307,226, 312 Amendment filed Oct. 24, 2011", 3 pgs.
"U.S. Appl. No. 10/307,226, Appeal Brief filed Oct. 14, 2010", 15 pgs.
"U.S. Appl. No. 10/307,226, Final Office Action mailed Jun. 27, 2008", 6 pgs.
"U.S. Appl. No. 10/307,226, Final Office Action mailed Dec. 12, 2006", 5 pgs.
"U.S. Appl. No. 10/307,226, Non Final Office Action mailed Mar. 13, 2006", 6 pgs.
"U.S. Appl. No. 10/307,226, Non Final Office Action mailed Jun. 12, 2007", 5 pgs.
"U.S. Appl. No. 10/307,226, Non Final Office Action mailed Sep. 9, 2009", 16 pgs.
"U.S. Appl. No. 10/307,226, Notice of Allowance mailed Jul. 22, 2011", 8 pgs.
"U.S. Appl. No. 10/307,226, Preliminary Amendment filed Jul. 22, 2005", 3 pgs.
"U.S. Appl. No. 10/307,226, PTO Response to 312 Amendment mailed Nov. 10, 2011", 3 pgs.
"U.S. Appl. No. 10/307,226, Response filed Apr. 9, 2007 to Final Office Action mailed Dec. 12, 2006", 7 pgs.
"U.S. Appl. No. 10/307,226, Response filed Jun. 23, 2009 to Final Office Action mailed Jun. 27, 2008", 10 pgs.
"U.S. Appl. No. 10/307,226, Response filed Sep. 15, 2006 to Non Final Office Action mailed Mar. 13, 2006", 6 pgs.
"U.S. Appl. No. 10/307,226, Response filed Dec. 14, 2007 to Non Final Office Action mailed Jun. 12, 2007", 7 pgs.
"U.S. Appl. No. 10/669,881, Preliminary Amendment May 6, 2005", 3 pgs.
"U.S. Appl. No. 10/669,881, Response filed Mar. 11, 2008 to Final Office Action mailed Jan. 25, 2008", 8 pgs.
"U.S. Appl. No. 10/669,881, Response filed May 15, 2006 to Non Final Office Action mailed Jan. 27, 2006", 9 pgs.
"U.S. Appl. No. 10/669,881, Response filed Sep. 7, 2007 to Restriction Requirement mailed Jun. 19, 2007", 4 pgs.
"U.S. Appl. No. 10/669,881, Response filed Oct. 2, 2006 to Restriction Requirement mailed Jul. 27, 2006", 6 pgs.
"U.S. Appl. No. 10/669,881, Restriction Requirement Jul. 27, 2006", 5 pgs.
"U.S. Appl. No. 10/669,881, Restriction Requirement mailed Jun. 19, 2007", 5 pgs.
"U.S. Appl. No. 10/752,435, Response filed Jan. 9, 2008 to Final Office Action mailed Jul. 12, 2007", 10 pgs.

(56) References Cited

OTHER PUBLICATIONS

"U.S. Appl. No. 10/752,435, Response filed Jan. 25, 2010 to Non Final Office Action mailed Jul. 21, 2009", 9 pgs.

"U.S. Appl. No. 10/752,435, Response filed Apr. 9, 2007 to Non Final Office Action mailed Oct. 19, 2006", 13 pgs.

"U.S. Appl. No. 10/752,435, Response filed May 12, 2009 to Final Office Action mailed Dec. 8, 2008", 9 pgs.

"U.S. Appl. No. 10/752,435, Response filed Sep. 19, 2008 to Non Final Office Action mailed Mar. 18, 2008", 7 pgs.

"U.S. Appl. No. 10/786,465, Supplemental Amendment filed Mar. 18, 2008", 8 pgs.

"U.S. Appl. No. 10/808,216, Preliminary Amendment filed Jun. 15, 2005", 3 pgs.

"U.S. Appl. No. 11/166,428, Response filed May 12, 2009 to Final Office Action mailed Jan. 12, 2009", 6 pgs.

"U.S. Appl. No. 11/166,428, Response filed Nov. 17, 2008 to Non Final Office Action mailed May 14, 2008", 6 pgs.

"U.S. Appl. No. 11/166,428, Response filed Dec. 22, 2009 to Non Final Office Action mailed Dec. 16, 2009", 8 pgs.

"U.S. Appl. No. 11/365,056, Final Office Action mailed Dec. 9, 2010", 13 pgs.

"U.S. Appl. No. 11/365,056, Non Final Office Action mailed Mar. 23, 2010", 11 pgs.

"U.S. Appl. No. 11/365,056, Response filed Sep. 28, 2010 to Non Final Office Action mailed Mar. 23, 2010", 5 pgs.

"U.S. Appl. No. 11/365,056, Response filed Dec. 10, 2009 to Restriction Requirement mailed Jun. 10, 2009", 44 pgs.

"U.S. Appl. No. 11/365,056, Restriction Requirement mailed Jun. 10, 2009", 5 pgs.

"U.S. Appl. No. 11/540,428, Response filed May 12, 2011 to Non Final Office Action mailed Nov. 12, 2010", 12 pgs.

"U.S. Appl. No. 11/540,428, Response filed Oct. 1, 2010 to Restriction Requirement mailed Mar. 29, 2010", 6 pgs.

"U.S. Appl. No. 11/540,428, Restriction Requirement mailed Mar. 29, 2010", 9 pgs.

"U.S. Appl. No. 11/633,724, Final Office Action mailed Jun. 22, 2010", 6 pgs.

"U.S. Appl. No. 11/633,724, Response filed Jun. 8, 2010 to Final Office Action mailed Dec. 8, 2009", 4 pgs.

"U.S. Appl. No. 11/978,753, Response filed Mar. 3, 2011 to Non Final Office Action mailed Sep. 3, 2010", 9 pgs.

"U.S. Appl. No. 11/981,112, Final Office Action mailed Oct. 8, 2013", 9 pgs.

"U.S. Appl. No. 11/981,112, Response filed Jan. 6, 2010 to Non Final Office Action mailed Jul. 8, 2009", 7 pgs.

"U.S. Appl. No. 11/981,112, Response filed Nov. 1, 2010 to Final Office Action mailed Apr. 29, 2010", 7 pgs.

"U.S. Appl. No. 12/288,032, Restriction Requirement mailed Nov. 4, 2011", 9 pgs.

"U.S. Appl. No. 12/288,045, Restriction Requirement mailed Nov. 16, 2011", 9 pgs.

"U.S. Appl. No. 12/315,015, Non Final Office Action mailed Sep. 27, 2013", 7 pgs.

"U.S. Appl. No. 12/942,232, Non Final Office Action mailed Oct. 9, 2013", 13 pgs.

"U.S. Appl. No. 13/157,242, Non Final Office Action mailed Oct. 31, 2013", 6 pgs.

"U.S. Appl. No. 13/162,384, Final Office Action mailed Aug. 27, 2013", 14 pgs.

"U.S. Appl. No. 13/162,384, Response filed Oct. 18, 2013 to Final Office Action mailed Aug. 27, 2013", 5 pgs.

"Australian Application Serial No. 2002351188, Office Action mailed Mar. 30, 2007", 1 pg.

"Australian Application Serial No. 2002351188, Office Action mailed Dec. 8, 2008", 3 pgs.

"Australian Application Serial No. 2004287354, Office Action mailed Oct. 13, 2009", 2 pgs.

"Australian Application Serial No. 2004287355, Office Action mailed May 11, 2009", 2 pgs.

"Australian Application Serial No. 2005204615, Office Action mailed Jan. 20, 2010", 4 pgs.

"Australian Application Serial No. 2006302908, Office Action mailed Mar. 4, 2011", 8 pgs.

"Australian Application Serial No. 2006305689, Office Action mailed Sep. 5, 2011", 3 pgs.

"Australian Application Serial No. 2006309241, Office Action mailed Mar. 4, 2011", 6 pgs.

"Canadian Application Serial No. 2,464,900, Office Action mailed Sep. 29, 2009", 3 pgs.

"Canadian Application Serial No. 2,539,585, Office Action mailed Aug. 31, 2010", 2 pgs.

"Canadian Application Serial No. 2,546,681, Office Action mailed Feb. 25, 2011", 3 pgs.

"Canadian Application Serial No. 2,546,721, Office Action mailed Feb. 25, 2011", 3 pgs.

"Canadian Application Serial No. 2,551,685, Office Action mailed Jan. 17, 2011", 3 pgs.

"Canadian Application Serial No. 02823581.9, Office Action mailed Mar. 1, 2006", 7 pgs.

"Canadian Application Serial No. 02823581.9, Office Action mailed Apr. 18, 2008", 6 pgs.

"Canadian Application Serial No. 02823581.9, Office Action mailed Aug. 8, 2007", 4 pgs.

"Canadian Application Serial No. 02823581.9, Office Action mailed Nov. 17, 2006", 7 pgs.

"Chinese Application Serial No. 02823581.9, Response filed Jan. 31, 2007 to Office Action mailed Nov. 17, 2006", 8 pgs.

"Chinese Application Serial No. 02823581.9, Response filed Apr. 7, 2006 to Office Action mailed Mar. 1, 2006", 4 pgs.

"Chinese Application Serial No. 02823581.9, Response filed May 19, 2008 to Office Action mailed Apr. 18, 2008", (W/English Translation), 38 pgs.

"Chinese Application Serial No. 02823581.9, Response filed Dec. 3, 2007 to Office Action mailed Aug. 8, 2007", 6 pgs.

"Chinese Application Serial No. 200480027649.7, Response filed Jan. 19, 2010 to Office Action mailed Sep. 4, 2009", 5 pgs.

"Chinese Application Serial No. 200480031226.2, Office Action mailed Jan. 23, 2009", 9 pgs.

"Chinese Application Serial No. 200480031226.2, Office Action mailed Apr. 27, 2010", (W/English Translation), 7 pgs.

"Chinese Application Serial No. 200480031226.2, Office Action mailed Dec. 21, 2010", (W/English Translation), 10 pgs.

"Chinese Application Serial No. 200480031226.2, Response filed Feb. 25, 2011 to Office Action mailed Dec. 21, 2010", (W/English Translation), 18 pgs.

"Chinese Application Serial No. 200480031226.2, Response filed May 22, 2009 to Office Action mailed Jan. 23, 2009", 5 pgs.

"Chinese Application Serial No. 200480031226.2, Response filed Jul. 12, 2010 to Office Action mailed Apr. 27, 2010", 5 pgs.

"Chinese Application Serial No. 200580002026.9, Office Action mailed Jun. 19, 2009", (W/English Translation), 12 pgs.

"Chinese Application Serial No. 200580002026.9, Response filed Jan. 4, 2010 to Office Action mailed Jun. 19, 2009", 10 pgs.

"Chinese Application Serial No. 200580009570.6, Office Action mailed May 9, 2008", (W/English Translation), 2 pgs.

"Chinese Application Serial No. 200580009570.6, Response filed Nov. 21, 2008 to Office Action mailed May 9, 2008", 7 pgs.

"Chinese Application Serial No. 200680034052.4, Response filed Mar. 1, 2010 to Office Action mailed Aug. 14, 2009", 4 pgs.

"Chinese Application Serial No. 200680034052.4, Response filed Sep. 26, 2010 to Office Action mailed May 11, 2010", 5 pgs.

"Chinese Application Serial No. 200680038882.4, Office Action mailed May 11, 2010", (W/English Translation), 18 pgs.

"Chinese Application Serial No. 200680046854.7, Office Action mailed Apr. 14, 2010", (W/English Translation), 18 pgs.

"Chinese Application Serial No. 200680046854.7, Response filed Sep. 26, 2010 to Office Action mailed Apr. 14, 2010", 10 pgs.

"Chinese Application Serial No. 200680047552.1, Office Action mailed Jun. 4, 2010", (W/English Translation), 7 pgs.

"Chinese Application Serial No. 200680047552.1, Response filed Dec. 20, 2010 to Office Action mailed Jun. 4, 2010", 10 pgs.

(56) References Cited

OTHER PUBLICATIONS

"Chinese Application Serial No. 200810210922.X, Office Action mailed Jan. 19, 2012", (W/English Translation), 6 pgs.
"Chinese Application Serial No. 200810210922.X, Office Action mailed Apr. 2, 2010", (W/English Translation), 4 pgs.
"Chinese Application Serial No. 200810210922.X, Office Action mailed Aug. 23, 2011", 6 pgs.
"Chinese Application Serial No. 200810210922.X, Response filed Jun. 1, 2012 to Office Action mailed Jan. 19, 2012", 5 pgs.
"Chinese Application Serial No. 200810210922.X, Response filed Aug. 12, 2010 to Office Action mailed Apr. 2, 2010", 10 pgs.
"Chinese Application Serial No. 200910139527.1, Response filed Nov. 28, 2011 to Office Action mailed Jul. 12, 2010", 9 pgs.
"European Application Serial No. 02789196.9, European Search Report mailed Aug. 14, 2009", 5 pgs.
"European Application Serial No. 02789196.9, Office Action mailed Feb. 6, 2012", 4 pgs.
"European Application Serial No. 02789196.9, Office Action mailed Mar. 7, 2012", 3 pgs.
"European Application Serial No. 02789196.9, Office Action mailed Apr. 19, 2010", 4 pgs.
"European Application Serial No. 02789196.9, Office Action mailed Jul. 14, 2011", 3 pgs.
"European Application Serial No. 02789196.9, Response filed Jan. 18, 2012 to Office Action mailed Jul.14, 2011", 19 pgs.
"European Application Serial No. 02789196.9, Response filed Feb. 16, 2012 to Office Action mailed Feb. 6, 2012", 9 pgs.
"European Application Serial No. 02789196.9, Response filed Apr. 5, 2012 to Office Action mailed Mar. 7, 2012", 5 pgs.
"European Application Serial No. 02789196.9, Response filed Oct. 25, 2010 to Office Action mailed Apr. 19, 2010", 16 pgs.
"European Application Serial No. 05704902.5, European Search Report mailed Aug. 29, 2011", 3 pgs.
"European Application Serial No. 06802578.2, European Search Report mailed Mar. 7, 2013", 10 pgs.
"German Application Serial No. 10297483.7, Office Action mailed Jan. 9, 2006", 4 pgs.
"German Application Serial No. 10297483.7, Office Action mailed Jul. 8, 2006", 2 pgs.
"German Application Serial No. 10297483.7, Office Action mailed and Response filed Oct. 30, 2006", 8 pgs.
"German Application Serial No. 10297483.7, Response filed Jul. 7, 2006 to Office Action mailed Jan. 9, 2006", 14 pgs.
"German Application Serial No. 10297483.7, Response filed Oct. 26, 2006 to Office Action mailed Jul. 8, 2006", 3 pgs.
"Great Britain Application Serial No. 0411107.6, Office Action mailed Feb. 28, 2005", 3 pgs.
"Great Britain Application Serial No. 0411107.6, Office Action mailed Sep. 29, 2005", 1 pg.
"Great Britain Application Serial No. 0411107.6, Response filed Aug. 23, 2005 to Office Action mailed Feb. 28, 2005", 3 pgs.
"Great Britain Application Serial No. 0411107.6, Response filed Oct. 31, 2005 to Office Action mailed Sep. 29, 2005", 4 pgs.
"Great Britain Application Serial No. 0522152.8, Office Action mailed Dec. 5, 2005", 5 pgs.
"Great Britain Application Serial No. 0522152.8, Response filed Apr. 26, 2006 to Office Action mailed Dec. 5, 2005", 48 pgs.
"International Application Serial No. PCT/US2002/032753, International Preliminary Examination Report mailed Aug. 16, 2004", 3 pgs.
"International Application Serial No. PCT/US2002/032753, International Search Report mailed Mar. 6, 2003", 1 pg.
"International Application Serial No. PCT/US2005/005453, International Preliminary Report on Patentability mailed Feb. 16, 2006", 3 pgs.
"International Application Serial No. PCT/US2005/005453, International Search Report mailed Aug. 30, 2005", 1 pg.
"International Application Serial No. PCT/US2005/005453, International Written Opinion mailed Aug. 30, 2005", 3 pgs.
"Japanese Application Serial No. 2003-546789, Office Action mailed Oct. 7, 2009", 3 pgs.
"Japanese Application Serial No. 2003-546789, Response filed May 21, 2009 to Office Action mailed Feb. 26, 2009", 6 pgs.
"Japanese Application Serial No. 2006-528036, Office Action mailed Jan. 19, 2010", 3 pgs.
"Japanese Application Serial No. 2006-536616, Office Action mailed Jun. 23, 2008", (W/English Translation), 8 pgs.
"Japanese Application Serial No. 2006-536616, Response filed Dec. 19, 2008 to Office Action mailed Jun. 23, 2008", (W/English Translation), 9 pgs.
"Japanese Application Serial No. 2006-536617, Office Action mailed Jun. 17, 2008", (W/English Translation), 3 pgs.
"Japanese Application Serial No. 2006-536617, Response filed May 12, 2009 to Office Action mailed Jun. 17, 2008", (W/English Translation), 19 pgs.
"Japanese Application Serial No. 2006-547608, Office Action mailed Jun. 23, 2008", (W/English Translation), 5 pgs.
"Japanese Application Serial No. 2006-547608, Respone filed Dec. 19, 2008 to Office Action mailed Jun. 23, 2008", (W/English Translation), 10 pgs.
"Japanese Application Serial No. 2007504965, Response filed Mar. 11, 2011 to Office Action mailed Sep. 14, 2010", 8 pgs.
"Japanese Application Serial No. 2008-306790, Office Action mailed May 31, 2011", 1 pg.
"Japanese Application Serial No. 2008-306790, Response filed Nov. 29, 2011 to Office Action mailed May 8, 2012", 2 pgs.
"Japanese Application Serial No. 2008-306790, Response filed Nov. 9, 2011 to Office Action mailed May 31, 2011", (W/English Translation), 12 pgs.
"Japanese Application Serial No. 2008-316282, Office Action mailed May 16, 2011", 2 pgs.
"Japanese Application Serial No. 2008-316296, Office Action mailed Feb. 28, 2011", 2 pgs.
"Japanese Application Serial No. 2008-316296, Office Action mailed Jun. 22, 2010", 2 pgs.
"Japanese Application Serial No. 2008-323279, Office Action mailed Sep. 30, 2010", 1 pg.
"Japanese Application Serial No. 2008-323290, Office Action mailed Jun. 6, 2012", (W/English Translation), 8 pgs.
"Japanese Application Serial No. 2008-323290, Office Action mailed Jun. 8, 2011", (W/English Translation), 8 pgs.
"Japanese Application Serial No. 2008-323290, Response filed Dec. 7, 2011 to Office Action mailed Jun. 8, 2011", (W/English Translation), 16 pgs.
"Japanese Application Serial No. 2008-536574, Office Action mailed Mar. 11, 2010", (W/English Translation), 4 pgs.
"Japanese Application Serial No. 2008-536574, Office Action mailed Oct. 3, 2011", (W/English Translation), 7 pgs.
"Japanese Application Serial No. 2008-536575, Office Action mailed Jul. 7, 2011", (W/English Translation), 5 pgs.
"Japanese Application Serial No. 2008-536576, Office Action mailed Jul. 19, 2011", (W/English Translation), 4 pgs.
"Japanese Application Serial No. 2008-536577, Notice of Allowance mailed May 30, 2012", 3 pgs.
"Japanese Application Serial No. 2008-536577, Response filed Jan. 6, 2012 to Office Action mailed Jul. 8, 2011", (W/English Translation), 3 pgs.
"U.S. Appl. No. 12/288,034, Final Office Action mailed Nov. 4, 2013", 8 pgs.
"U.S. Appl. No. 13/495,836, Response filed Nov. 5, 2013 to Non Final Office Action mailed Aug. 5, 2013", 8 pgs.

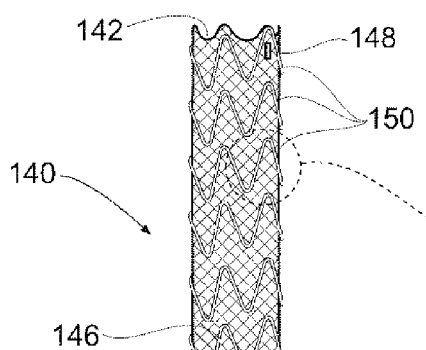
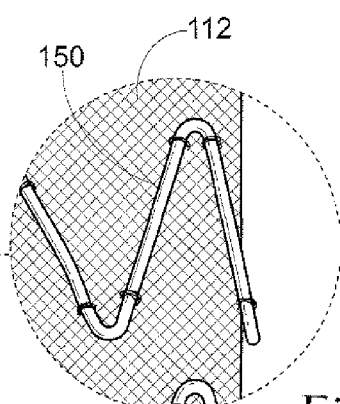
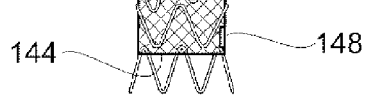
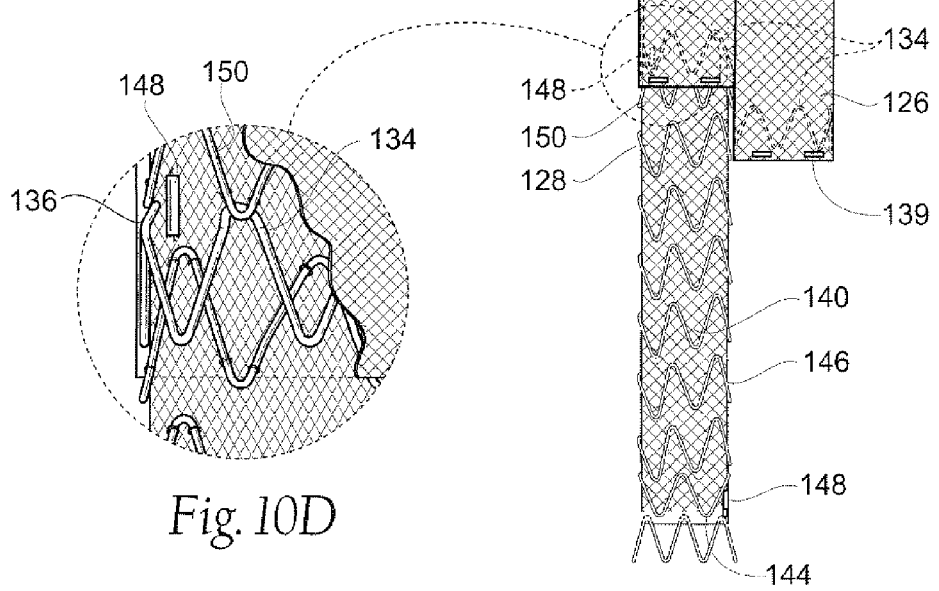
Fig. 10A
Fig. 10B
Fig. 10C
Fig. 10D

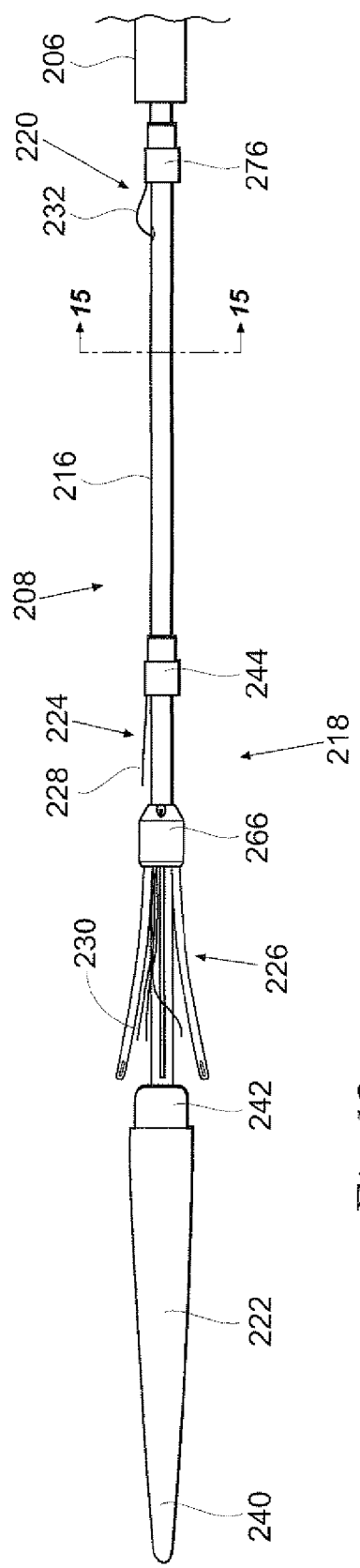
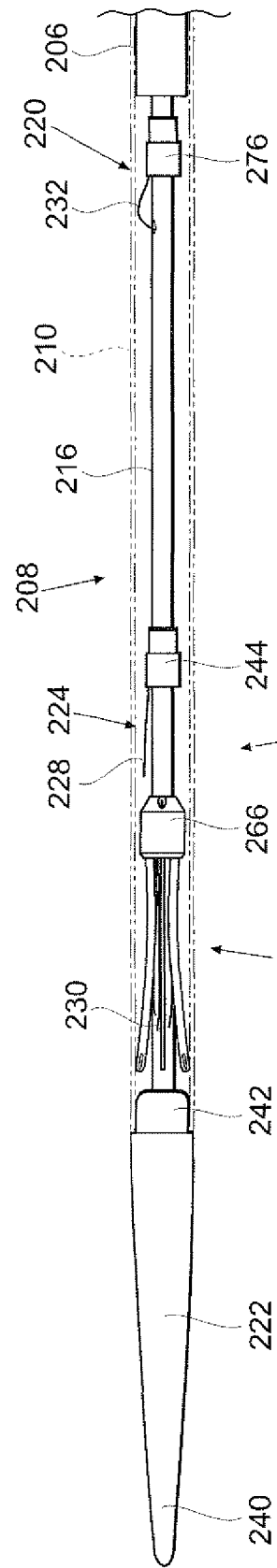
Fig.12
Fig.13

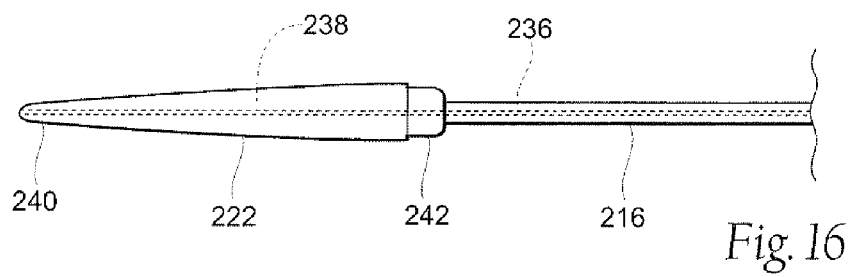
Fig. 16
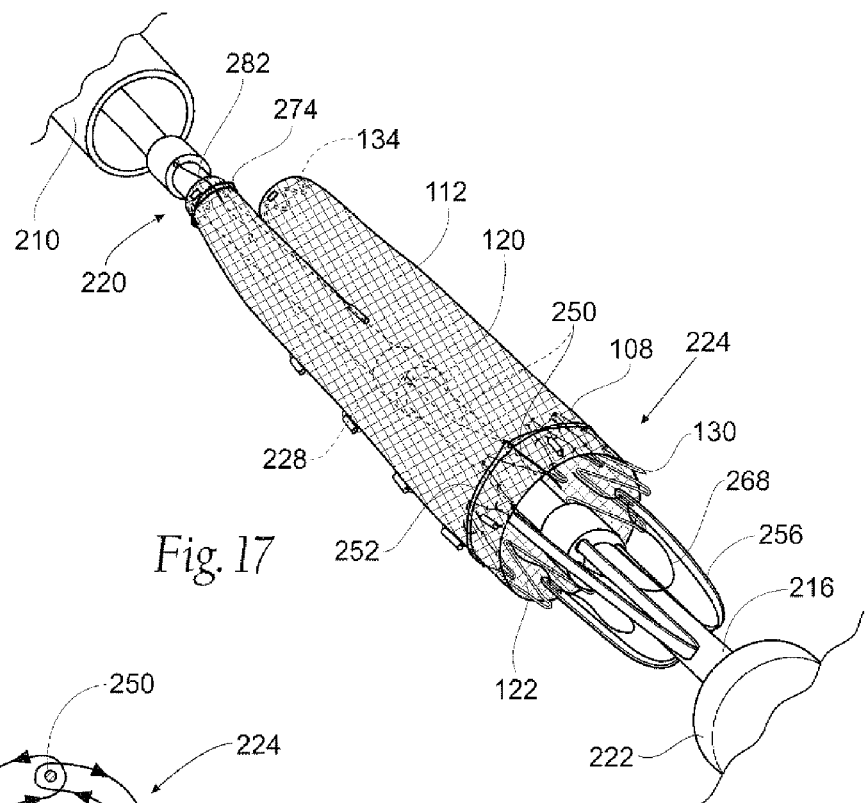
Fig. 17
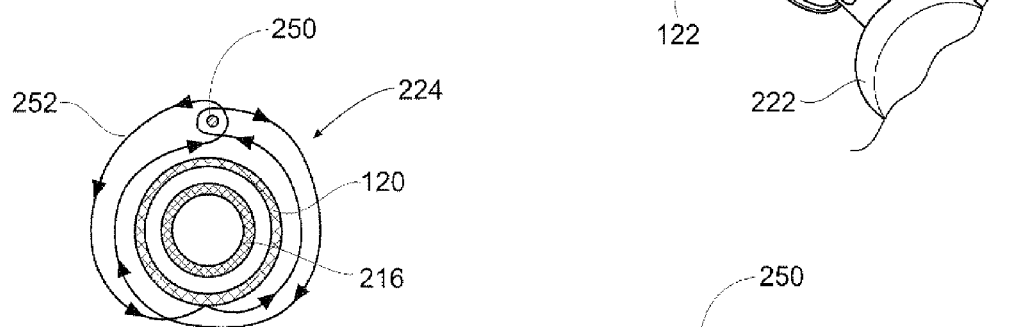
Fig. 18A
Fig. 18B

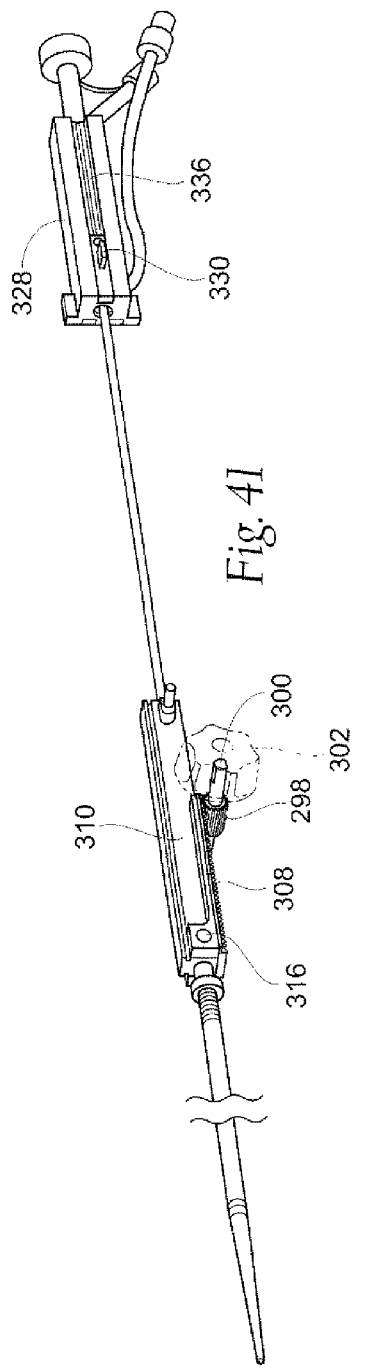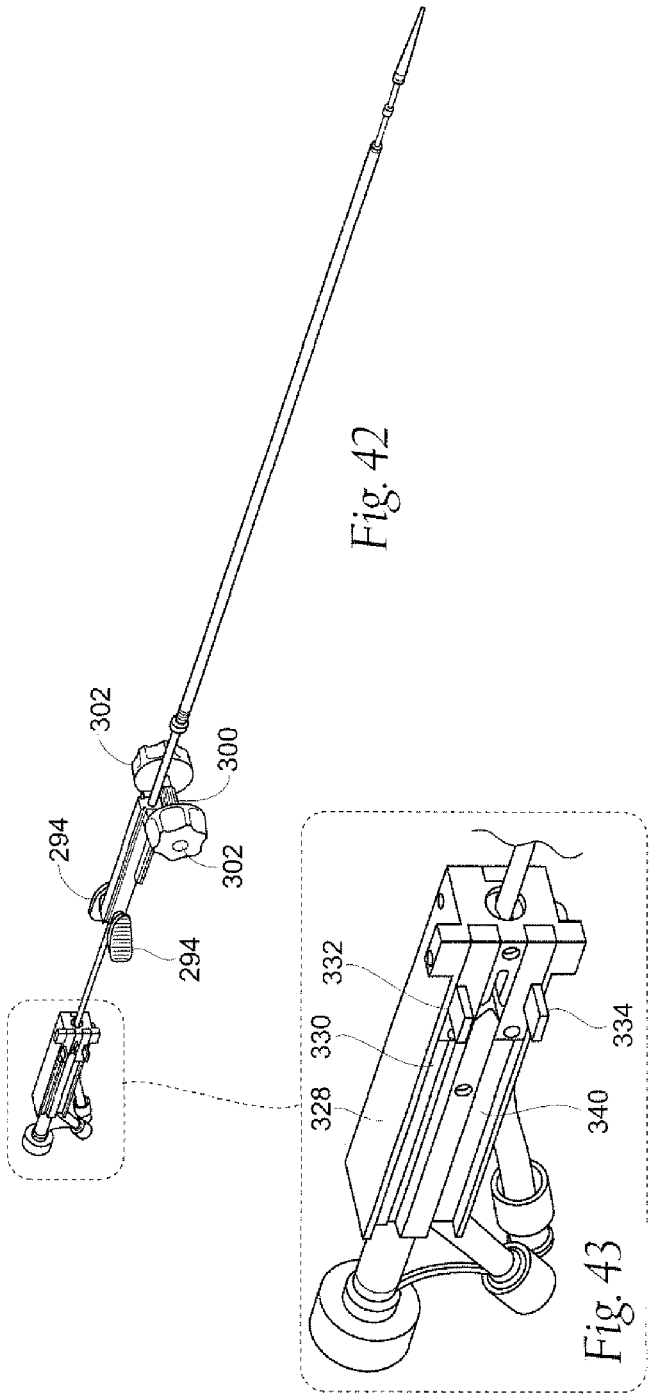

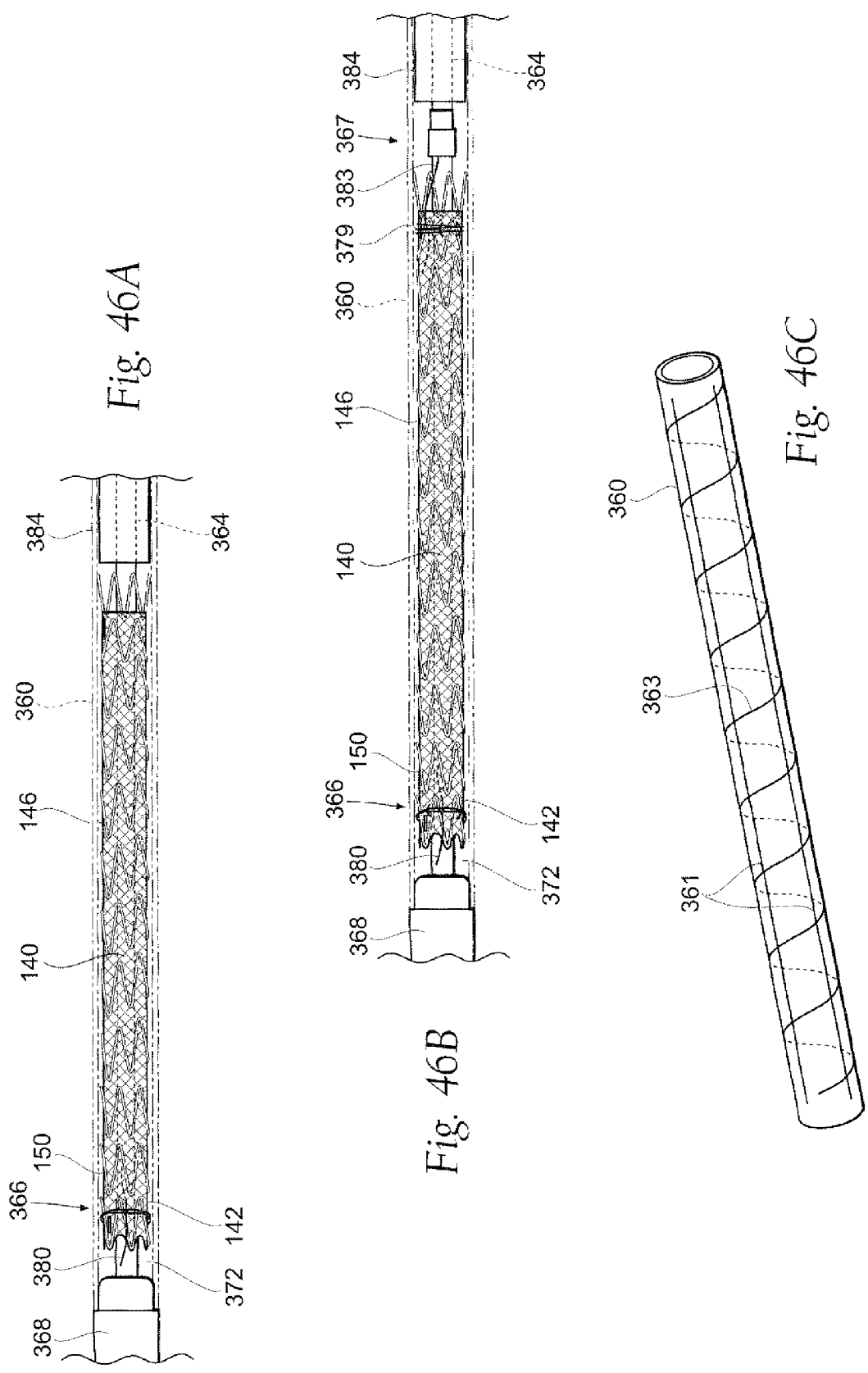

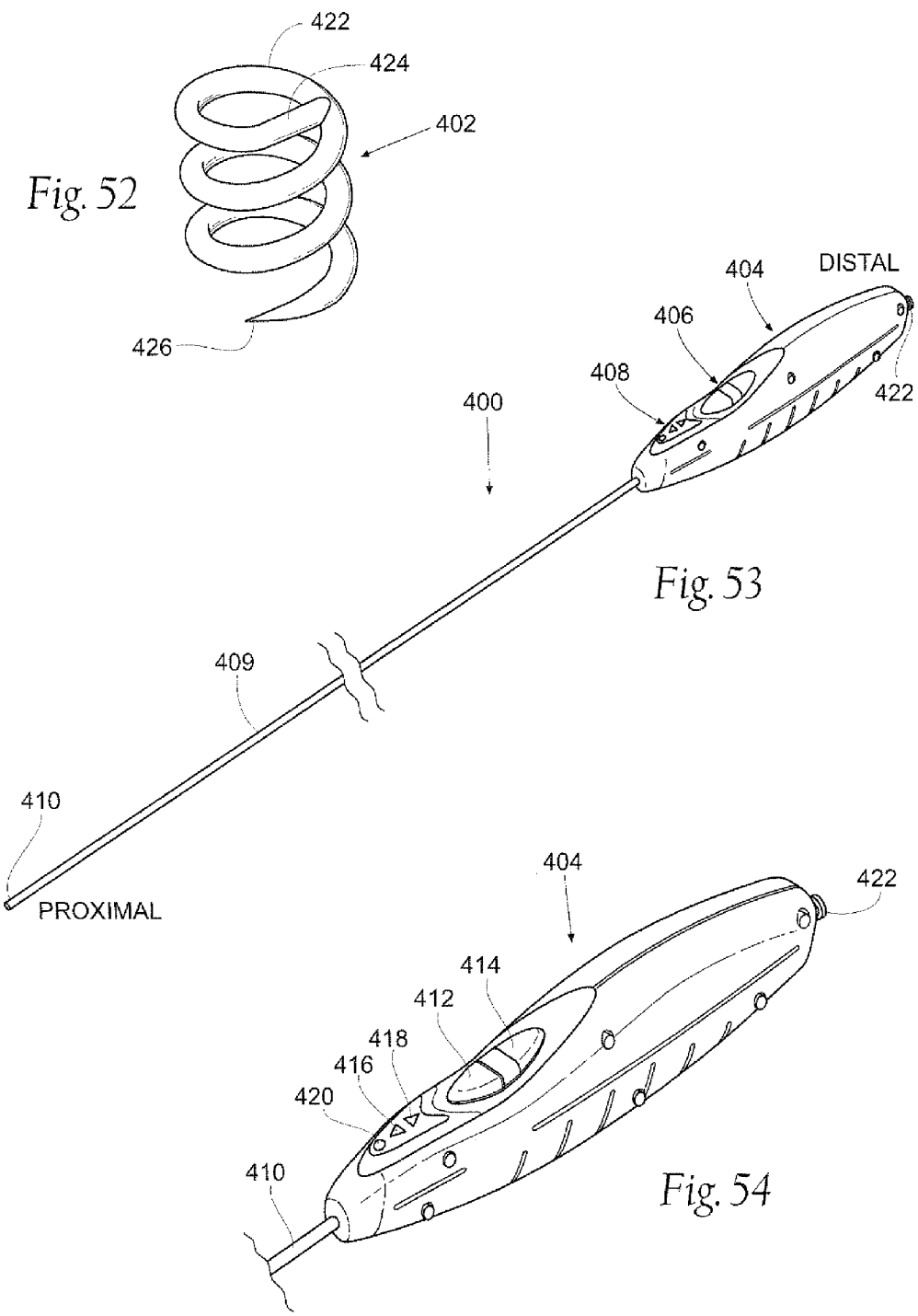

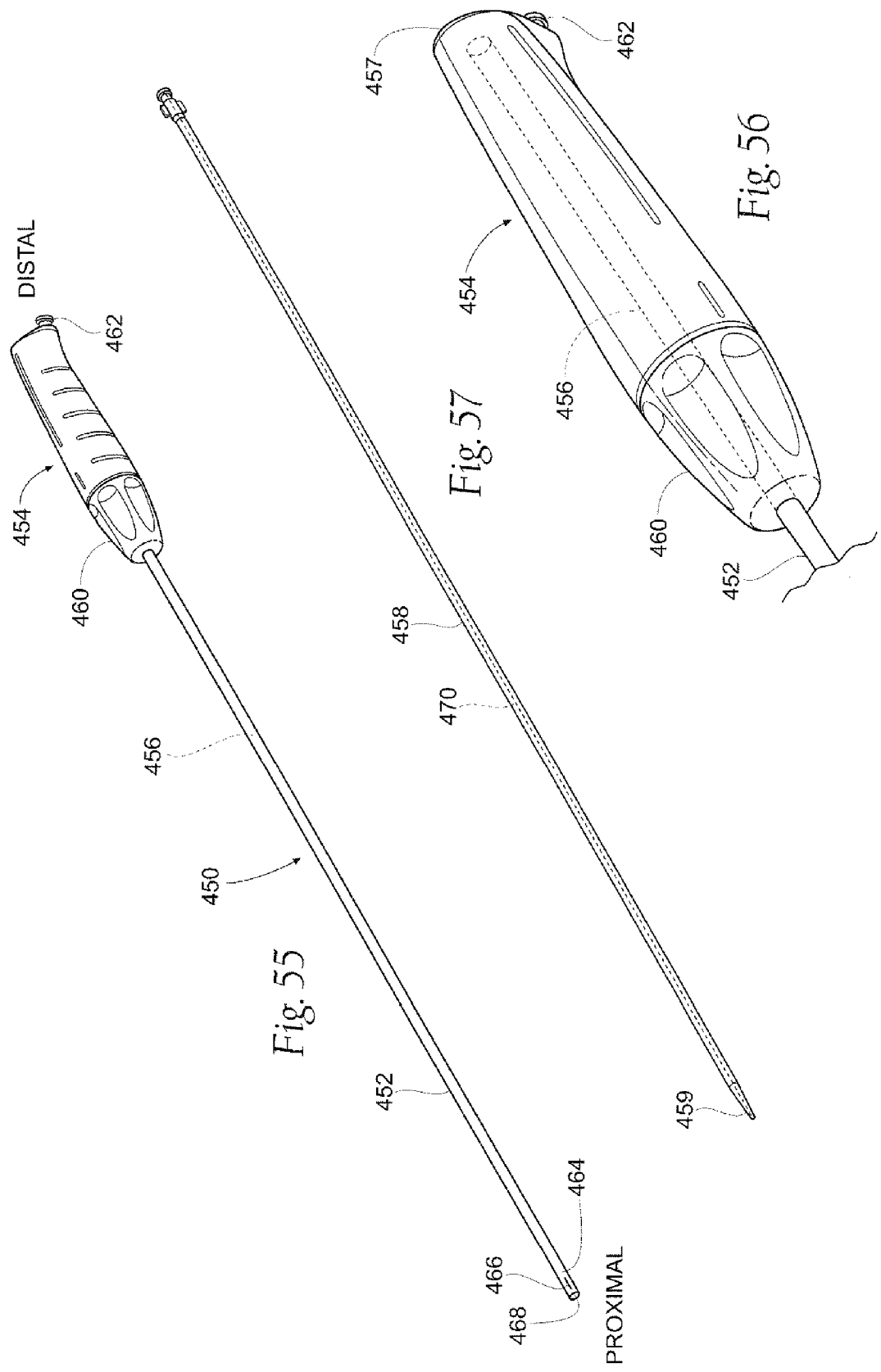

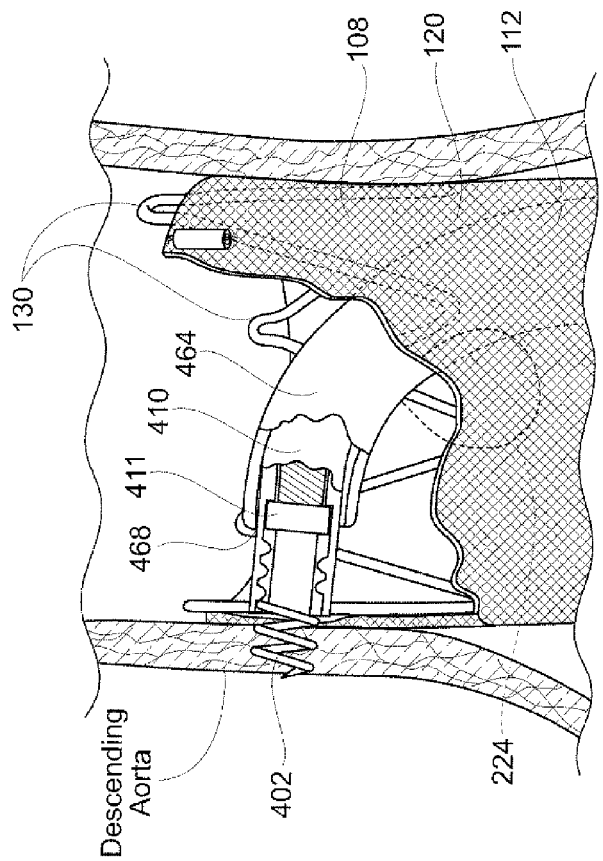
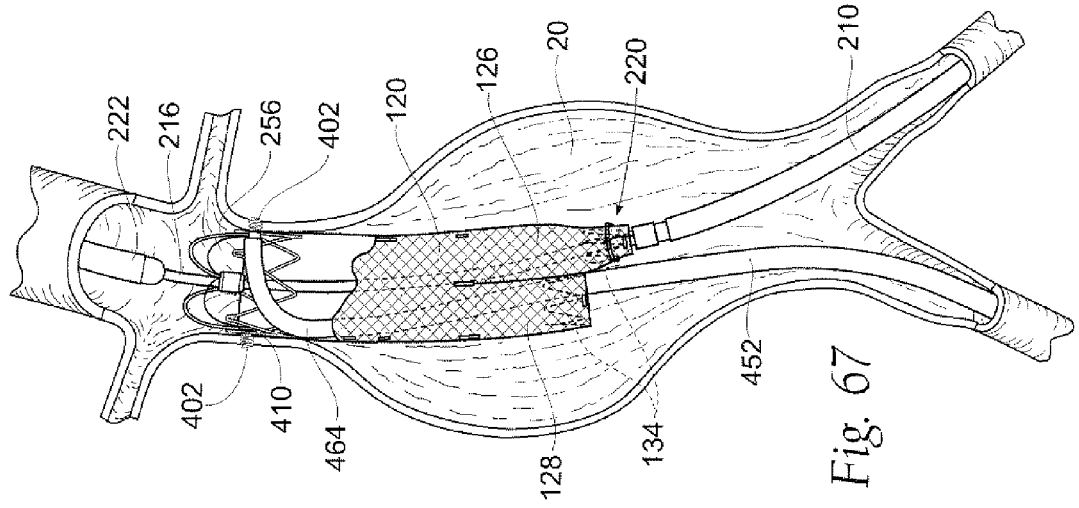
Fig. 66
Fig. 67

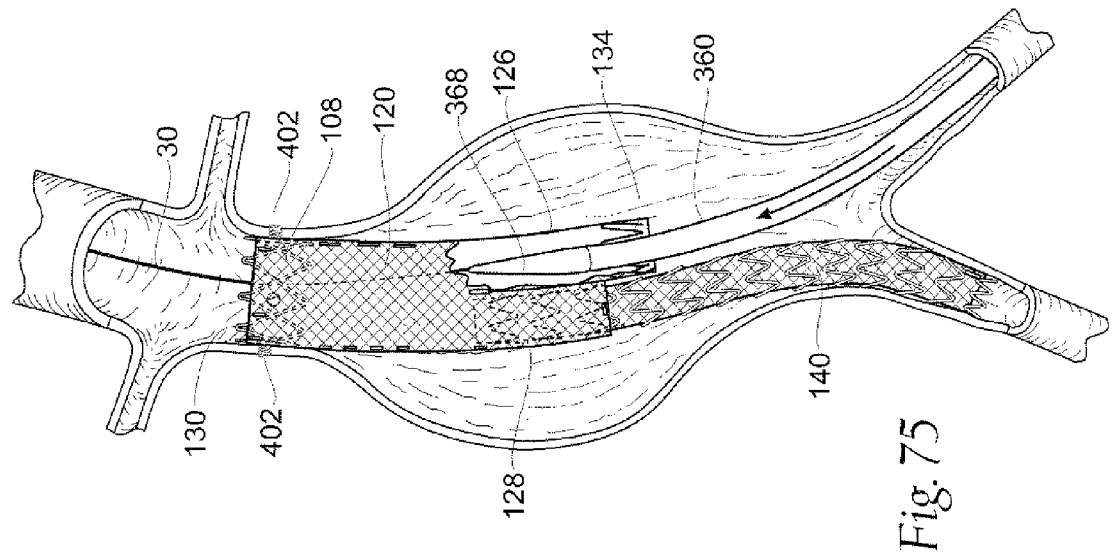
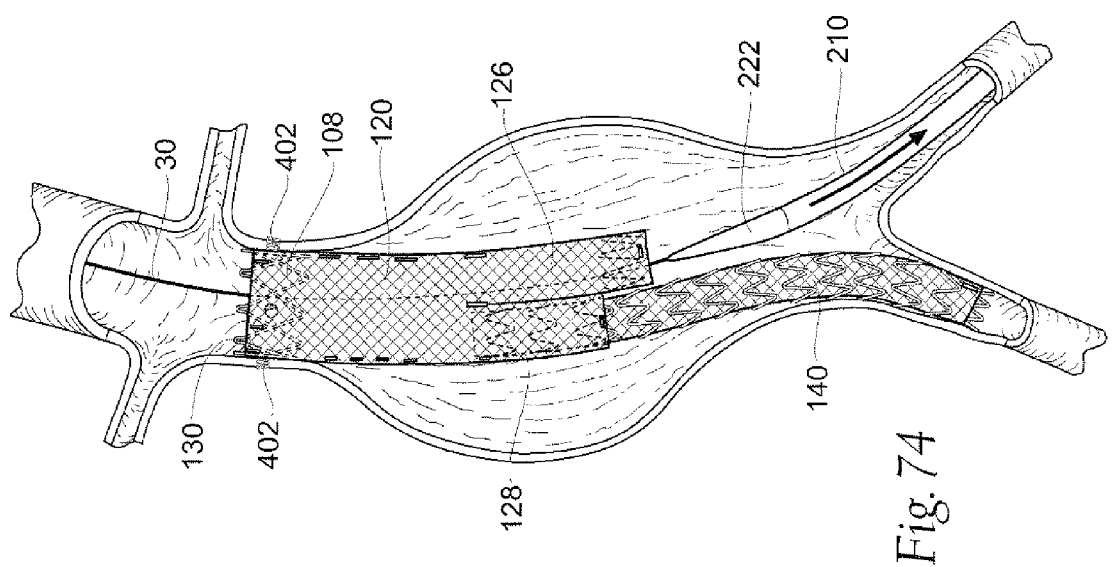

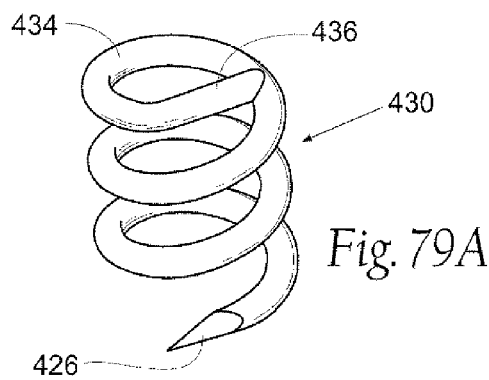
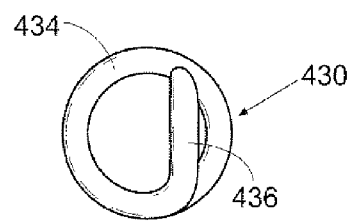
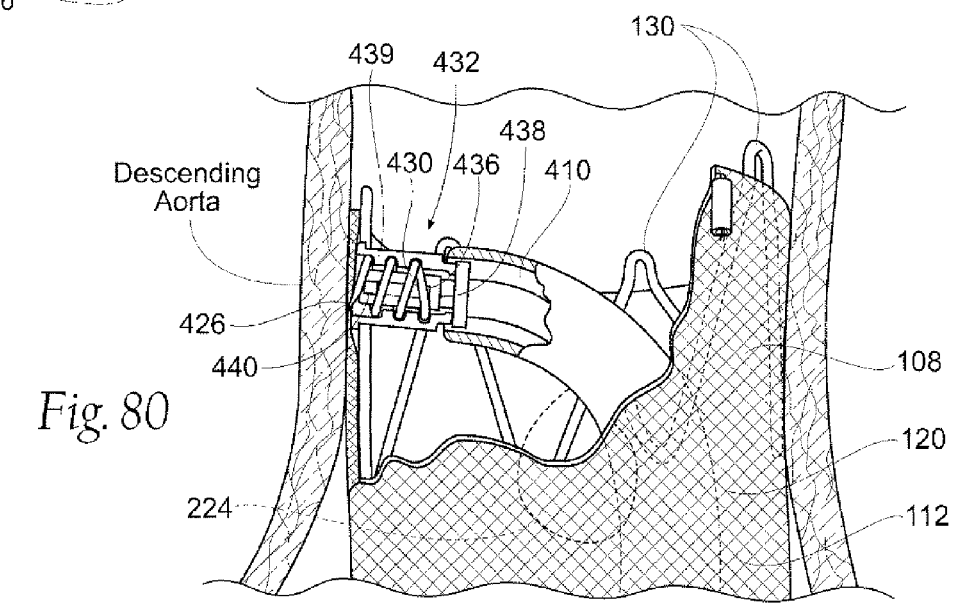
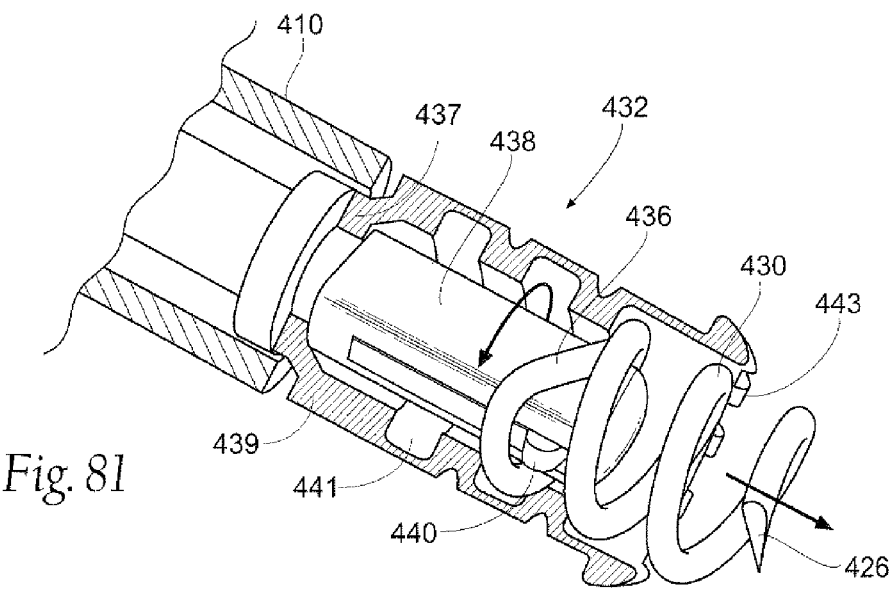

DEVICES, SYSTEMS, AND METHODS FOR PROSTHESIS DELIVERY AND IMPLANTATION, INCLUDING THE USE OF A FASTENER TOOL

RELATED APPLICATIONS

This application is divisional of co-pending U.S. patent application Ser. No. 11/254,950, filed 20 Oct. 2005, which is a continuation-in-part of co-pending U.S. patent application Ser. No. 11/254,619, filed 20 Oct. 2005, and entitled "Devices, Systems, and Methods for Guiding an Operative Tool Into an Interior Body Region", which is incorporated herein by reference. U.S. patent application Ser. No. 11/254,950 also is a continuation-in-part of U.S. patent application Ser. No. 10/692,283, filed 23 Oct. 2003, now U.S. Pat. No. 7,147,657, and entitled "Prosthesis Delivery Systems and Methods," which claims the benefit of U.S. Provisional Patent Application Ser. No. 60/488,753, filed 21 Jul. 2003, and entitled "Endoprosthesis Delivery Systems and Methods." U.S. patent application Ser. No. 11/254,950 also is a continuation-in-part of co-pending U.S. patent application Ser. No. 10/786,465, filed 25 Feb. 2004, and entitled "Systems and Methods for Attaching a Prosthesis Within a Body Lumen or Hollow Organ," which is a continuation-in-part of U.S. patent application Ser. No. 10/693,255, now U.S. Pat. No. 6,929,661, and entitled "Multi-Lumen Prosthesis Systems and Methods," which claims the benefit of U.S. Provisional Patent Application Ser. No. 60/489,011, filed Jul. 21, 2003, and entitled "Bifurcated Prosthesis Systems and Methods." U.S. patent application Ser. No. 11/254,950 also is a continuation-in-part of co-pending U.S. patent application Ser. No. 10/307,226, filed 29 Nov. 2002, and entitled "Intraluminal Prosthesis Attachment Systems and Methods." U.S. patent application Ser. No. 11/254,950 is also a continuation-in-part of U.S. patent application Ser. No. 10/669,881, filed 24 Sep. 2003, now U.S. Pat. No. 7,491,232, entitled "Catheter-Based Fastener Implantation Apparatus and Methods with Implantation Force Resolutions." U.S. patent application Ser. No. 11/254,950 is also a continuation-in-part of U.S. patent application Ser. No. 11/166,411, filed 24 Jun. 2005, entitled "Endovascular Aneurysm Repair System," which is a division of U.S. patent application Ser. No. 10/271,334, filed 15 Oct. 2002, now U.S. Pat. No. 6,960,217, which claims the benefit of U.S. Provisional Patent Application Ser. No. 60/333,937, filed 28 Nov. 2001, and entitled "Endovascular Aneurysm Repair System."

FIELD OF THE INVENTION

The invention relates generally to devices, systems, and methods for the delivery and implantation of a prosthesis to a targeted site within the body, e.g., for the repair of diseased and/or damaged sections of a hollow body organ and/or blood vessel.

BACKGROUND OF THE INVENTION

The weakening of a vessel wall from damage or disease can lead to vessel dilatation and the formation of an aneurysm. Left untreated, an aneurysm can grow in size and may eventually rupture.

For example, aneurysms of the aorta primarily occur in the abdominal region, usually in the infrarenal area between the renal arteries and the aortic bifurcation. Aneurysms can also occur in the thoracic region between the aortic arch and renal arteries. The rupture of an aortic aneurysm results in massive hemorrhaging and has a high rate of mortality.

Open surgical replacement of a diseased or damaged section of vessel can eliminate the risk of vessel rupture. In this procedure, the diseased or damaged section of vessel is removed and a prosthetic prosthesis, made either in a straight or bifurcated configuration, is installed and then permanently attached and sealed to the ends of the native vessel by suture. The prosthetic prosthesis for these procedures are usually unsupported woven tubes and are typically made from polyester, ePTFE or other suitable materials. The prosthesis are longitudinally unsupported so they can accommodate changes in the morphology of the aneurysm and native vessel. However, these procedures require a large surgical incision and have a high rate of morbidity and mortality. In addition, many patients are unsuitable for this type of major surgery due to other co-morbidities.

Endovascular aneurysm repair has been introduced to overcome the problems associated with open surgical repair. The aneurysm is bridged with a vascular prosthesis, which is placed intraluminally. Typically these prosthetic prostheses for aortic aneurysms are delivered collapsed on a catheter through the femoral artery. These prostheses are usually designed with a fabric material attached to a metallic scaffolding (stent) structure, which expands or is expanded to contact the internal diameter of the vessel. Unlike open surgical aneurysm repair, intraluminally deployed prostheses are not sutured to the native vessel, but rely on either barbs extending from the stent, which penetrate into the native vessel during deployment, or the radial expansion force of the stent itself is utilized to hold the prosthesis in position. These prosthesis attachment means do not provide the same level of attachment when compared to suture and can damage the native vessel upon deployment.

Accordingly, there is a need for improved prosthesis delivery devices, systems, and methods that deliver a prosthetic graft to a body lumen, the prosthesis being able to adapt to changes in aneurysm morphology and able to be deployed safely and without damage to the native vessel.

SUMMARY OF THE INVENTION

The devices, systems, and methods for delivering and implanting radially expandable prostheses in the body lumens are described. In particular, the present invention provides improved devices, systems, and methods for implanting vascular prostheses into blood vessels, including both arterial and venous systems. In the exemplary embodiments, prostheses are placed in vasculature to reinforce aneurysms, particularly abdominal aortic aneurysms.

One aspect of the invention provides devices, systems, and methods for fastening a prosthesis into a hollow body organ or blood vessel. The devices, systems, and methods include a fastener applier that is sized and configured for securing a prosthesis, the fastener applier comprising a handle assembly positioned at the caudal end of the fastener applier, a fastener applier shaft coupled to the handle assembly, and a fastener driver for advancing a fastener into the prosthesis and tissue, the fastener driver coupled to the fastener applier shaft at the cephalad end of the fastener applier shaft, the fastener driver including a housing and a release latch, wherein the release latch prevents premature release of the fastener from the fastener driver. The fastener driver housing may also include an internally threaded portion and a non-threaded portion, the non-threaded portion providing an area where the fastener can be rotated but not advanced out of the driver, the advancement out of the driver only taking place if the fastener has been previously engaged in tissue or the prosthesis.

In one embodiment, the handle assembly may further include a motion control assembly to be used by an operator, the motion control assembly providing motion control of the fastener within the fastener driver. The motion control assembly may include a forward control function and a reverse control function. The handle assembly may also include an indication assembly to provide information to an operator, the indication assembly providing at least one of an audible and visual indication. The information provided may include at least one of a fastener position or timing or status or error, or any combination.

In one embodiment, fastener is a helical fastener. The helical fastener may include a fastener body having a distal end for penetrating tissue in response to a force and a proximal end for releasably coupling the fastener body to the fastener applier, and a stop structure associated with the proximal end to prevent over-penetration of the fastener body into tissue, the stop structure bisecting the diameter of the fastener body. The stop structure may be offset from the diameter of the fastener body.

An additional aspect of the invention provides devices, systems, and methods for storing a fastener used for securing a prosthesis into a hollow body organ or blood vessel. The devices, systems, and methods comprise a base structure, and at least one receptacle positioned within the base structure, the receptacle sized and configured to releasably store at least one fastener. The receptacle may be sized and configured to releasably store at least one helical fastener. The helical fastener may include a fastener body having a distal end for penetrating tissue in response to a force and a proximal end for releasably coupling the fastener body to the fastener applier, and a stop structure associated with the proximal end to prevent over-penetration of the fastener body into tissue, the stop structure bisecting the diameter of the fastener body. The stop structure may be offset from the diameter of the fastener body.

In one embodiment the receptacle is sized and configured to present the fastener to a fastener applier. There may also be a post positioned within the receptacle to releasably restrain the fastener. A pliable material may also be included within the receptacle to position a tip of the fastener in the pliable material to releasably restrain the fastener. The fastener may also be releasably restrained within the receptacle by friction between the fastener and the receptacle wall.

Yet an additional aspect of the invention provides devices, systems, and methods for installing a fastener to a fastener applier used for securing a prosthesis in to a hollow body organ or blood vessel. The devices, systems, and methods comprise providing an apparatus for storing a fastener, the apparatus comprising a base structure, and at least one receptacle positioned within the base structure, the receptacle sized and configured to releasably store at least one fastener, providing a fastener applier for securing a prosthesis, the fastener applier comprising a handle assembly positioned at the caudal end of the fastener applier, a fastener applier shaft coupled to the handle assembly, and a fastener driver for advancing a fastener into the prosthesis and tissue, the fastener driver coupled to the fastener applier shaft at the cephalad end of the fastener applier shaft, the fastener driver including a housing and a release latch, wherein the release latch prevents premature release of the fastener from the fastener driver, positioning the fastener driver so as to allow the fastener driver to couple to releasably stored fastener, and coupling the fastener to the fastener applier. The step of coupling the fastener to the fastener applier may also include operating a motion control assembly positioned on the handle assembly to retract the fastener out of the receptacle and onto the fastener driver.

In one embodiment, the receptacle is sized and configured to releasably secure at least one helical fastener. The helical fastener may include a fastener body having a distal end for penetrating tissue in response to a force and a proximal end for releasably coupling the fastener body to the fastener applier, and a stop structure associated with the proximal end to prevent over-penetration of the fastener body into tissue, the stop structure bisecting the diameter of the fastener body. The stop structure may be offset from the diameter of the fastener body.

Other features and advantages of the invention shall be apparent based upon the accompanying description, drawings, and claims.

BRIEF DESCRIPTION OF THE DRAWINGS

FIG. 10A is a side view of an alternative embodiment of the prosthesis lumen extension of FIG. 9A, and shows securing stents without deflected apices.

FIG. 10B is an enlarged view showing detail of the securing stents of the lumen extension shown in FIG. 10A.

FIG. 10C is a side view showing the alternative embodiment of the prosthesis lumen extension of FIG. 10A coupled to the main body component of the multi-lumen prosthesis.

FIG. 10D is an enlarged view showing detail of the securing stents of the alternative embodiment of the lumen extension coupled to the distal stent of the main body prosthesis, as shown in FIG. 10C.

FIG. 12 is a side view of one embodiment of the proximal end of the deployment catheter of FIG. 11.

FIG. 13 is a side view of the proximal end of the deployment catheter of FIG. 11, and showing a jacket covering components of the deployment catheter.

FIG. 16 is a side view of the catheter tip and central shaft of the deployment catheter showing the catheter tip lumen and central shaft lumen.

FIG. 17 is a perspective view of the main body component of the multi-lumen prosthesis positioned on the proximal end of the deployment catheter prior to deployment, and showing the first proximal retaining means in a compressed condition.

FIG. 18A is a side view of one embodiment of a suture loop path around the main body component of the multi-lumen prosthesis.

FIG. 18B is a side view of an alternative embodiment of a suture loop path around the multi-lumen prosthesis of FIG. 18A, showing multiple suture loops.

FIG. 41 is a perspective view of a second side of one embodiment of a rack and pinion mechanism and a release system positioned within the deployment catheter handle assembly.

FIG. 42 is a perspective view of a second side of one embodiment of a rack and pinion mechanism and a release system positioned within the deployment catheter handle assembly.

FIG. 43 is a perspective view showing detail of the release system positioned within the deployment catheter handle assembly.

FIG. 46A is a side view of a proximal section of the lumen extension deployment catheter of FIG. 45A, and showing a jacket covering the lumen extension positioned on the catheter shaft prior to deployment.

FIG. 46B is a side view of an alternative embodiment of a proximal section of the lumen extension deployment catheter of FIG. 45B, and showing a jacket covering the lumen extension positioned on the catheter shaft prior to deployment and including a distal retaining means.

FIG. 46C is a perspective view of an alternative embodiment of the lumen extension deployment catheter jacket of FIG. 44 showing structural reinforcement.

FIG. 52 is an enlarged perspective view of one embodiment of a helical fastener that can be used in association with a fastener tool or device shown in FIG. 53.

FIG. 53 is a perspective view of a fastener tool that embodies features of the invention.

FIG. 54 is a perspective view of the handle assembly of the fastener tool of FIG. 53.

FIG. 55 is a perspective view of a steerable guide device that embodies features of the invention.

FIG. 56 is a perspective view of the handle assembly of the steerable guide device of FIG. 55.

FIG. 57 is a perspective view of an obturator or dilator that may be used in conjunction with the steerable guide device of FIG. 55.

FIG. 66 is an enlarged perspective view of the deployment of the main body component of the multi-lumen prosthesis within the descending aorta, and showing the steerable guide device and the fastener tool just after fastening a helical fastener through the prosthesis material and into tissue.

FIG. 67 is a perspective view of the deployment of the main body component of the multi-lumen prosthesis within the aneurysm of FIG. 58, and showing the deflected end of the steerable guide device and the fastener tool after being repositioned for deployment of an additional helical fastener.

FIG. 74 is a perspective view of the deployment of the main body component of the multi-lumen prosthesis within the aneurysm of FIG. 58, and showing the withdrawal of there jacketed main body deployment catheter over the fist guide wire.

FIG. 75 is a perspective view of the deployment of a second lumen extension component of the multi-lumen prosthesis within the aneurysm of FIG. 58, and showing the lumen extension catheter being positioned partially within a prosthesis lumen.

FIG. 79A is an enlarged perspective view of an alternative embodiment of a helical fastener that can be used in association with a fastener tool or device shown in FIG. 53.

FIG. 79B is an enlarged top view of the alternative fastener of FIG. 79A showing a "D" shape.

FIG. 80 is an enlarged perspective view of the deployment of the main body component of the multi-lumen prosthesis within the descending aorta, and showing the steerable guide device and the fastener tool having an alternative fastener driver just prior to fastening the helical fastener of FIG. 79A through the prosthesis material and into tissue.

FIG. 81 is an enlarged perspective view of the fastener driver and fastener of FIG. 80, and showing the fastener rotating off of the fastener carrier.

DETAILED DESCRIPTION OF THE INVENTION

This Specification discloses various catheter-based devices, systems, and methods for delivering and implanting radially expandable prostheses in the body lumens. For example, the various aspects of the invention have application in procedures requiring the repair of diseased and/or damaged sections of a hollow body organ and/or blood vessel. The devices, systems, and methods that embody features of the invention are also adaptable for use with systems and surgical techniques that are not necessarily catheter-based.

The devices, systems, and methods are particularly well suited for treating aneurysms of the aorta that primarily occur in the abdominal region, usually in the infrarenal area between the renal arteries and the aortic bifurcation, as well as aneurysms that also occur in the thoracic region between the aortic arch and renal arteries. For this reason, the devices, systems, and methods will be described in this context. Still, it should be appreciated that the disclosed devices, systems, and methods are applicable for use in treating other dysfunctions elsewhere in the body, which are not necessarily aorta-related.

I. Overview

Figure 1:
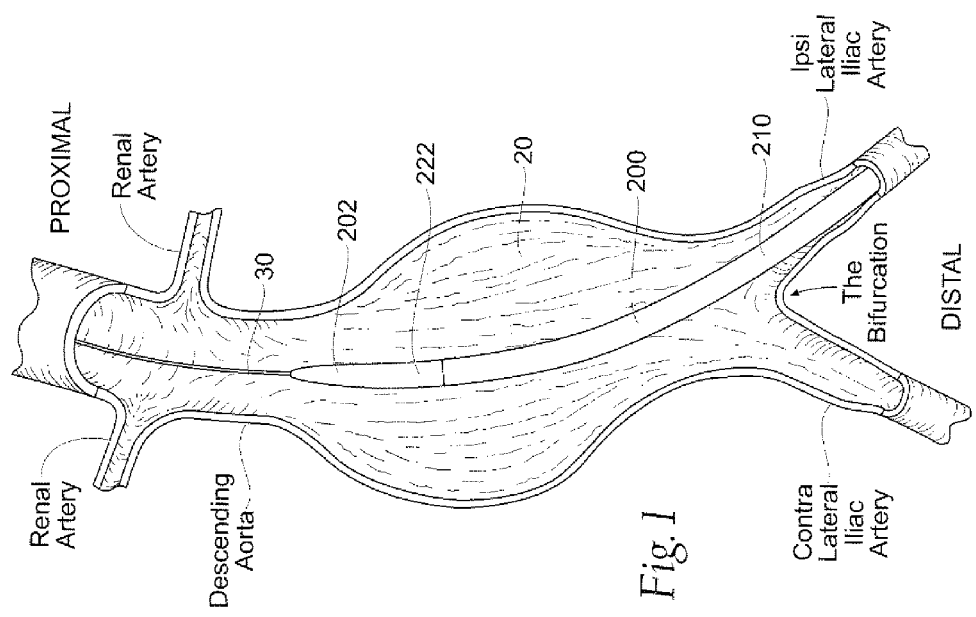
FIG. 1 is a perspective view of one embodiment of a prosthesis deployment catheter shown positioned with in an abdominal aortic aneurysm.

FIG. 1 depicts a portion of the descending aorta and shows an abdominal aortic aneurysm 20. For the purposes of illustration, FIG. 1 shows the targeted site for delivery and implantation of a prosthesis as being within the abdominal aortic aneurysm 20. It is to be appreciated that the targeted site can also be elsewhere in the body. In the illustrated arrangement, the prosthesis takes the form of an endovascular graft.

In order to provide a consistent orientation for the devices, systems, and methods described herein, the terms proximal or cephalad will be used to describe a relation or orientation toward the head or heart, and the terms distal or caudal will be used to describe a position or orientation toward the feet or away from the heart. Therefore, the devices, systems, and methods can be described as having a proximal or cephalad component and a distal or caudal component. The use of these terms also applies to the implantation apparatus as used in the implantation process described, i.e., the deployment catheter handle is distal or caudal as the handle of the deployment catheter is oriented toward the feet and away from the heart.

The proximal or cephalad end 202 of a prosthesis deployment catheter 200 can be seen in FIG. 1 positioned over a first guide wire 30 (the guide wire being previously positioned) and extending through at least a portion of the abdominal aortic aneurysm 20. The deployment catheter 200 carries the main body of the prosthesis 120 (see FIG. 2), which is placed at the targeted site, e.g., by radial expansion of the main body prosthesis 120 (see FIG. 3). After expansion of the main body prosthesis 120, one or more fasteners 402 (see FIG. 4) may be introduced by a fastener device 400 to anchor the proximal end 108 of the main body prosthesis, in place.

Figure 2:
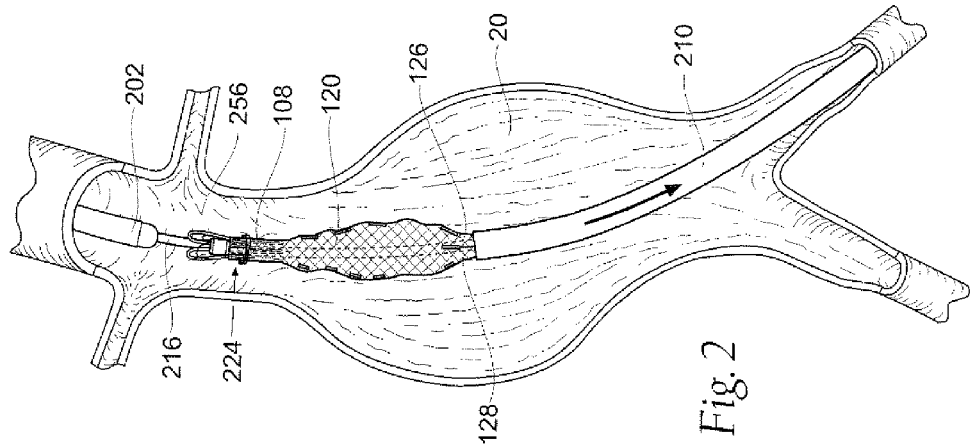
FIG. 2 is a perspective view of one embodiment of the deployment of a prosthesis within the aneurysm of FIG. 1, with the jacket partially retracted.
Figure 4:
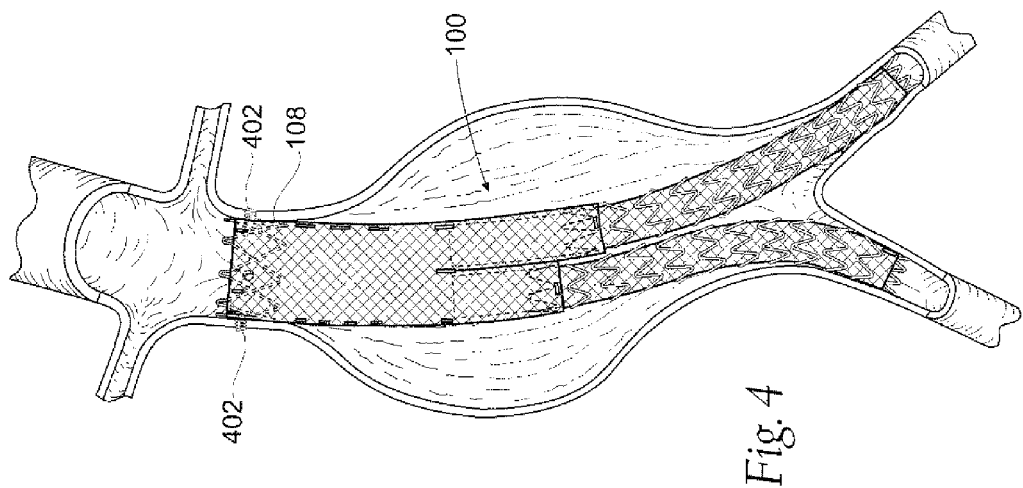
FIG. 4 is a perspective view of one embodiment of the completed deployment of a multi-lumen prosthesis within the aneurysm of FIG. 1.
Figure 3:
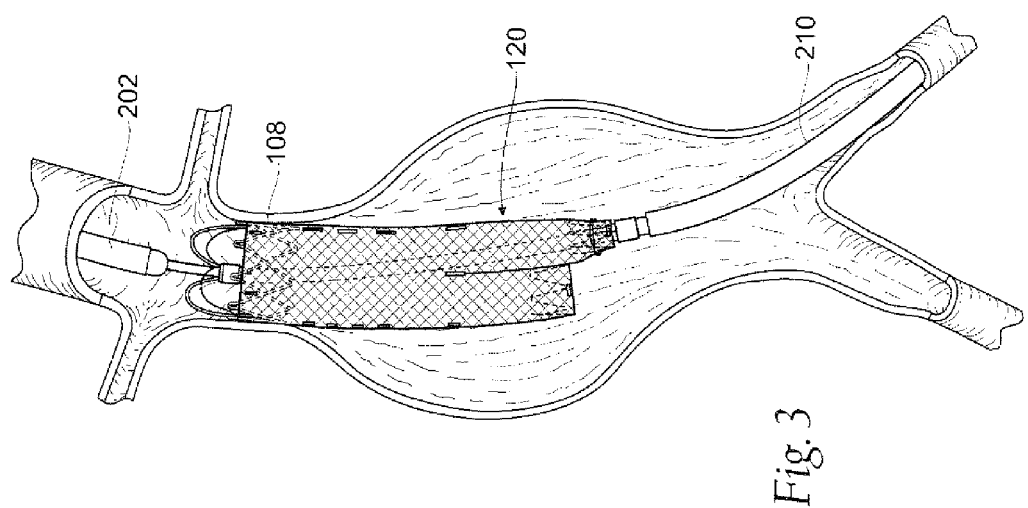
FIG. 3 is a perspective view of one embodiment of the deployment of a prosthesis within the aneurysm of FIG. 1, with the jacket fully retracted and showing radial expansion of the proximal end.

FIG. 2 depicts the initial stage of the main body prosthesis 120 deployment at the targeted site. While the deployment method can vary, in the illustrated embodiment, the delivery catheter 200 has a movable jacket or outer sheath 210, which overlays the main body prosthesis 120. When the outer jacket 210 is pulled distally, or in a caudal direction, the main body prosthesis 120 is exposed but may remain in an undeployed configuration until releasing means has been activated. Once the releasing means has been activated, the main body prosthesis or a portion(s) of the main body prosthesis 120 is free to radially expand, thereby enlarging to contact at least a portion of the internal walls of the blood vessel. The prosthesis deployment process is continued, including the deployment of one or more lumen extensions, until a multi-lumen or bifurcated prosthesis 100 is fully deployed within the vessel, as can be seen in FIG. 4 and will be described in greater detail later.

It is to be understood that the terms prosthesis and prostheses both can mean an independent component, or multiple components coupled together, or multiple components not necessarily coupled together. The prosthesis may be either coupled together at or near the targeted site, or exterior the body, or a combination of both.

Figure 5:
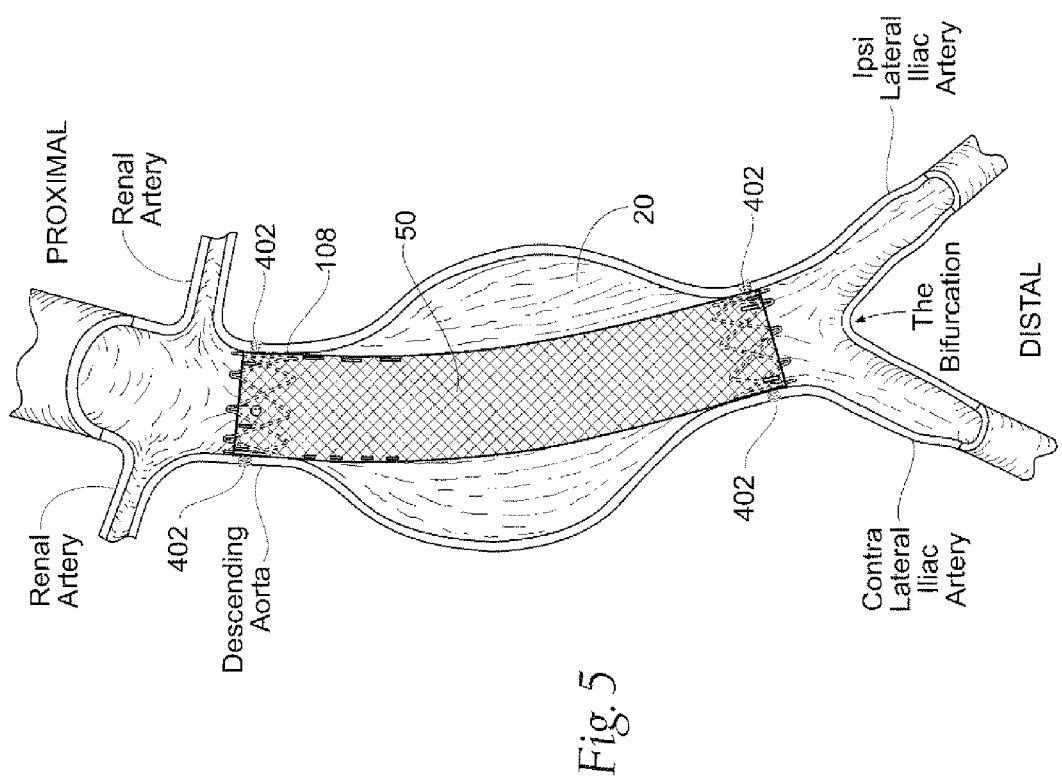
FIG. 5 is a perspective view of an alternative embodiment of the completed deployment of a single lumen prosthesis within the aneurysm of FIG. 1.

In a desirable embodiment, the prosthesis is a multi-lumen prosthesis. In an alternative embodiment, the prosthesis is a straight prosthesis. The prosthesis 100 may be self-expanding, or, the prosthesis 100 can utilize an expanding member, such as a balloon or mechanical expander. FIG. 4 depicts a completely deployed multi-lumen or bifurcated prosthesis 100 that is sized and configured to be positioned within the aorta and extend across the aneurysm and into the contralateral iliac artery and the ipsilateral iliac artery. FIG. 5 depicts a completely deployed straight prosthesis 50.

It is to be appreciated that one or more fasteners 402 can be introduced into the multi-lumen prosthesis 100 to anchor the main body 120 and/or lumen extensions 140 in place at different times or at the same time during the procedure.

II. General Methods of Endovascular Implantation

The prosthesis or prostheses 100 as just described lend themselves to implantation in a hollow organ in various ways. The prosthesis may be implanted using catheter-based technology via a peripheral intravascular access site, such as in the femoral artery, optionally with the assistance of image guidance. Image guidance includes but is not limited to fluoroscopy, ultra sound, magnetic resonance, computed tomography, or combinations thereof. Alternatively, the prosthesis can be implanted, e.g., in an open chest surgical procedure.

FIGS. 58 to 78 show a representative embodiment of the deployment of a prosthesis of the type shown in FIG. 4 by a percutaneous, catheter-based procedure. Percutaneous vascular access is achieved by conventional methods into the femoral artery, for example.

The implantation of the multi-lumen prosthesis 100 is first described here in a number of general steps. The multi-lumen prosthesis and each of the various tools used to implant the prosthesis are then described with additional detail below. The multi-lumen prosthesis 100 is described in section III and the various implantation apparatus are described in section IV. Additionally, the general implantation steps are then described again with additional detail below in section V.

A first implantation step can be generally described as deploying the main body 120 of the prosthesis. The deployment catheter 200 is positioned within the aortic aneurysm 20 and the main body of the pros thesis is allowed to deploy. Proximal and distal retaining means hold the main body prosthesis in a predetermined relationship to the proximal end 202 of the deployment catheter. By activating a proximal releasing means, the proximal end 108 of the main body prosthesis 120 may be partially or fully released from the deployment catheter shaft so as to allow the proximal stent 130 to expand to contact the aorta or a portion of the aorta. At this step the prosthesis may not be fully released from the deployment catheter. The main body prosthesis 120 may be attached to the deployment catheter 200 through a second proximal retaining means. The proximal end 108 or other areas of the main body prosthesis 120 is fastened to the vessel wall to resist axial migration of the prosthesis.

Next, an extension catheter 350 carrying a first prosthesis lumen extension 140 is guided through the vasculature and to the main body prosthesis 120. The first lumen extension is telescopically fitted within the second lumen 128 of the main body prosthesis 120 and allowed to radially expand. The extension catheter is then removed, leaving the lumen extension 140 coupled to the main body prosthesis 120 and extending into the contralateral iliac artery.

If the main body prosthesis 120 is attached to the deployment catheter 200 through a second proximal retaining means, a second releasing means is activated to allow the proximal end 108 of the main body prosthesis 120 to release from the deployment catheter shaft 216. The distal releasing means is then activated, allowing the distal end 110 of the main body prosthesis 120 to release from the deployment catheter shaft 216 and radially expand. The deployment catheter 200 is then removed from the body.

Lastly, the extension catheter 350 carrying a second prosthesis lumen extension 140 is guided through the vasculature and to the main body prosthesis 120. The second lumen extension 140 is telescopically fitted within the first lumen 126 of the main body prosthesis and allowed to radially expand. The extension catheter 350 is then removed, leaving the lumen extension 140 coupled to the main body prosthesis 120 and extending into the ipsilateral iliac artery. The multi-lumen prosthesis 100 is now fully deployed across the aortic aneurysm.

III. Multi-Lumen Prosthesis Assembly

Figure 6:
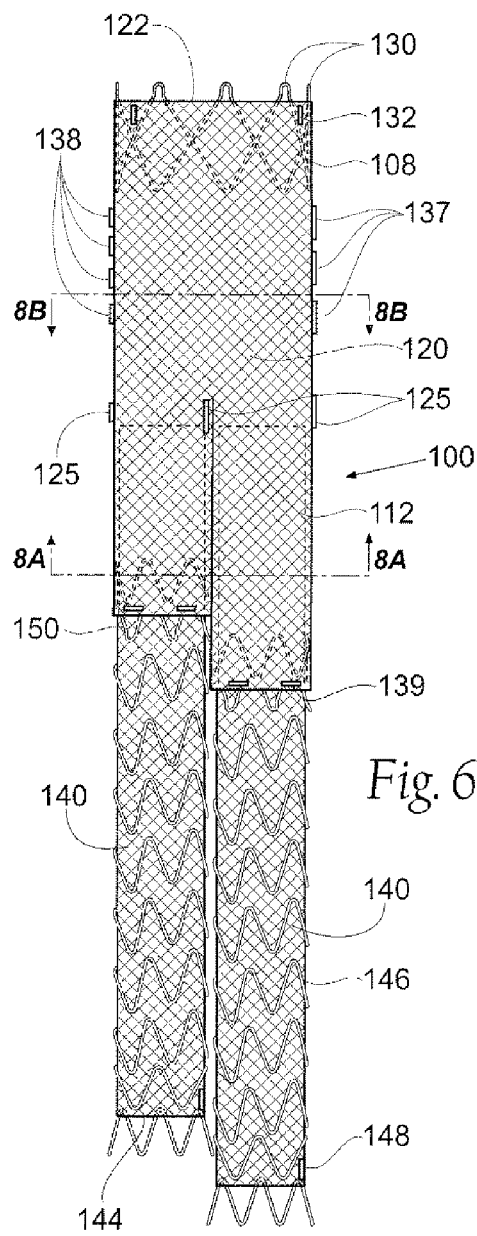
FIG. 6 is a side view of the multi-lumen prosthesis assembly that embodies features of the invention, the multi-lumen prosthesis assembly shown with lumen extensions.

FIG. 6 shows a multi-lumen prosthesis assembly 100 that embodies features of the invention. In the illustrated embodiment, the multi-lumen prosthesis assembly 100 comprises a main body component 120 and at least one lumen extension 140, desirably two lumen extensions.

The main body component 120 is sized and configured to fit within a hollow body organ and/or a blood vessel. As described in this Specification, the targeted site of deployment is within the aorta adjacent the renal arteries, as will be described in greater detail later. However, this targeted site of deployment is selected for purposes of illustrating the features of the prosthesis 100, and is not intended to be limiting.

Figure 7A:
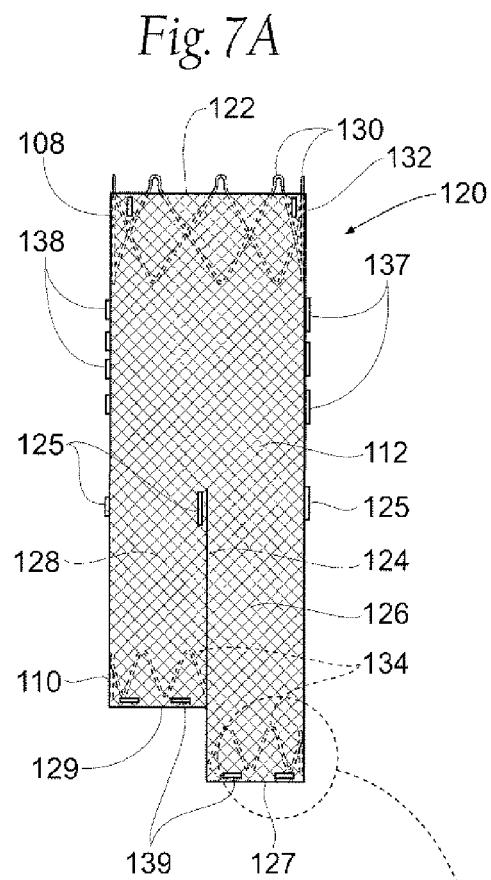
FIG. 7A is a side view of the main body component of the multi-lumen prosthesis assembly.
Figure 7B:
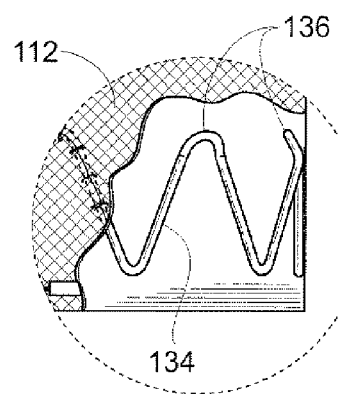
FIG. 7B is an enlarged view showing detail of the distal stent curved apices of the multi-lumen prosthesis shown in FIG. 7A.
Figure 7C:
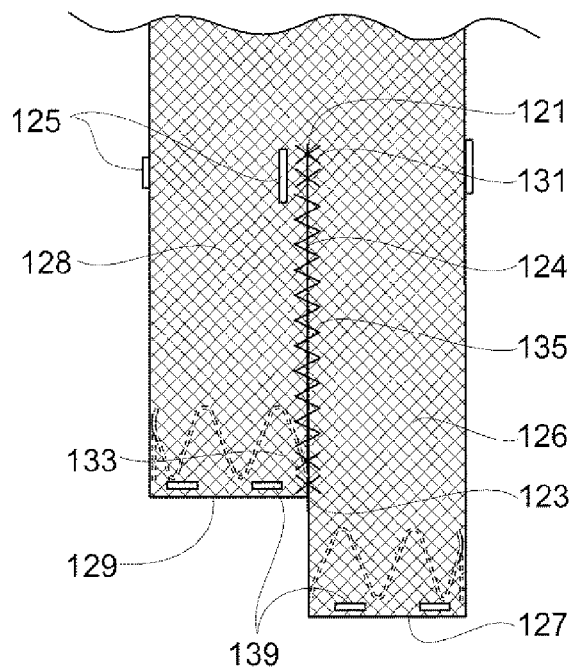
FIG. 7C is a side view of one embodiment of the prosthesis septum, showing stitches and weaving to form the septum.

Referring to FIG. 7A, the main body component 120 has a proximal and distal end 108, 110, and includes an interior communicating with a proximal opening 122 for fluid flow into or from the prosthesis. The main body component 120 includes a septum 124 within its interior. The length of the septum 124 within the prosthesis 120 can vary. In the illustrated embodiment, the septum 124 does not extend along the entire length of the main body component 120, but is spaced a distance from the proximal opening 122. In the illustrated arrangement, the septum 124 comprises a longitudinal seam. The seam can be formed by coupling the opposing surfaces together (i.e., the front and back) of the prosthesis material 112 (which is typically a fabric) by sewing, heat bonding, stitching or weaving, for example, or any combination. The coupling of the opposing surfaces together thereby creates a septum or shared, common wall between two lumens, the first lumen 126 and the second lumen 128 (see FIGS. 8A and 8B). Typically the seam 124 would be located along the midline of the main body to create two equally sized lumens 126 and 128. However, the location of the seam 124 could be moved, if different sized lumens were desired. In one embodiment shown in FIG. 7C, the septum 124 is formed by a stitch(s) 131 at the septum's proximal end 121, a stitch(s) 133 at the septums distal end 123, and a weave(s) 135 in-between the stitches 131, 133 at the septum's proximal end 121 and distal end 123. The combination of stitches and weaving, for example, provides added stability to the septum 124.

Figure 8A:
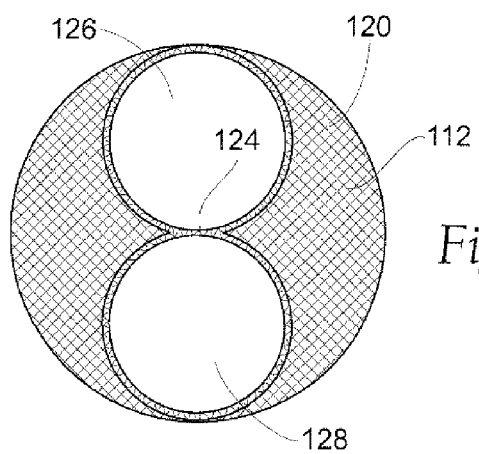
FIG. 8A is a section view of the distal end of the main body component of the multi-lumen prosthesis taken generally along line 8A-8A of FIG. 6.
Figure 8B:
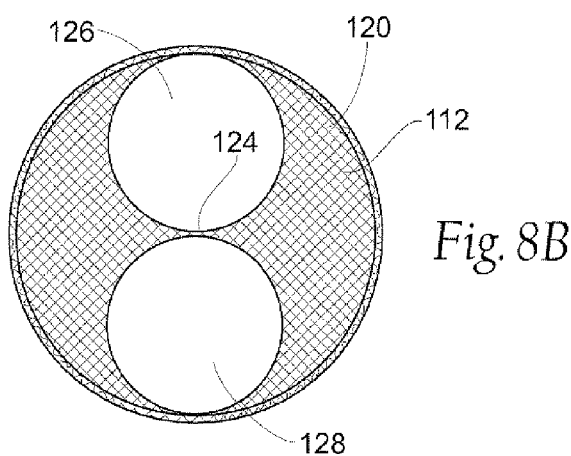
FIG. 8B is a section view of the proximal end of the main body component of the multi-lumen prosthesis taken generally along line 8B-8B of FIG. 6.

The septum 124 transforms at least a portion of the interior of the main body component 120 into the multi-lumen flow channel configuration. In the illustrated embodiment, the multi-lumen flow channel configuration comprises dual first and second interior lumens 126 and 128. Due to the septum 124, the dual first and second interior lumens 126 and 128 of the multi-lumen flow channel configuration do not form branched or divergent lumens. The shared common wall or seam (the septum 124) prevents divergence and maintains the lumens 126 and 128 in a non-divergent, generally parallel flow relationship (as FIGS. 8A and 8B show).

In the illustrated arrangement, the septum 124 runs generally along the mid-line of the main body component 120, making the multi-lumen flow channel configuration within the main body component 120 essentially symmetric. However, it should be appreciated that the septum 124 could form a non-symmetric multi-lumen flow channel configuration. It should also be appreciated that multiple septums can be present within the interior, transforming the interior of the main body component 120 into several flow lumens. The length of the septum can vary. In a representative embodiment, the septum 124 is typically greater than 10 mm in length and not less than 5 mm in length.

In the illustrated embodiment, the first lumen 126 defines a flow channel sized and configured to reach a targeted destination or source spaced a defined distance from the proximal opening 122, while the truncated second lumen 128 communicates with generally the same targeted destination as the proximal opening 122 of the main body component 120 itself. Furthermore, the septum 124 is sized and configured to accommodate the coupling of a flow channel extension 140 to the first lumen 126 and to the truncated second lumen 128, to likewise extend their reach to another targeted source or destination spaced from the proximal opening 122, if desired.

Figure 7D:
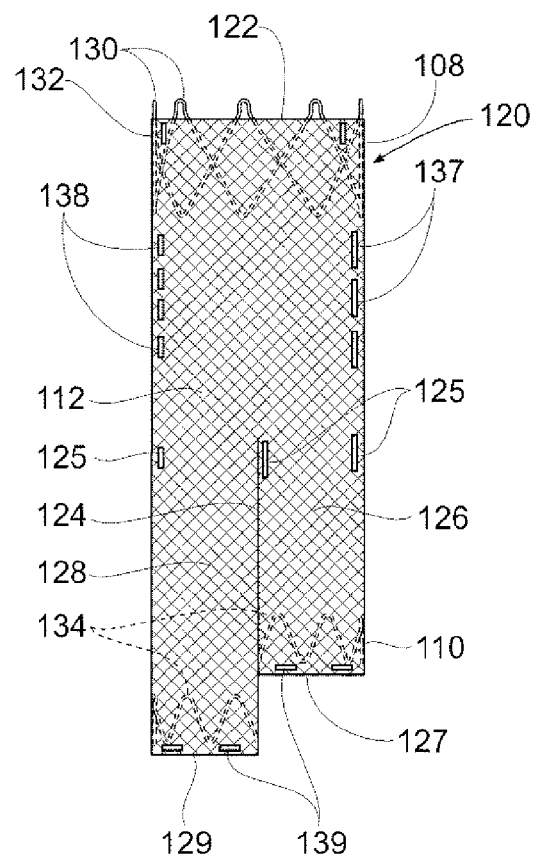
FIG. 7D is a side view of an alternative embodiment of the main body component of the multi-lumen prosthesis assembly of FIG. 7A, showing the main body prosthesis having a second lumen extending beyond the first lumen.

The second lumen 128 is truncated along at least a portion of the septum 124. As a result, the distal opening 127 of the first lumen 126 can be said to extend beyond the distal opening 129 of the second lumen 128. Still, the shared common wall (the septum 124) prevents divergence and maintains the lumens 126 and 128 in a non-divergent, generally parallel flow relationship. It is to be appreciated that the first and second lumens 126, 128 may be reversed, i.e., the second lumen 128 may extend beyond the first lumen 126 (see FIG. 7D).

Figure 9A:
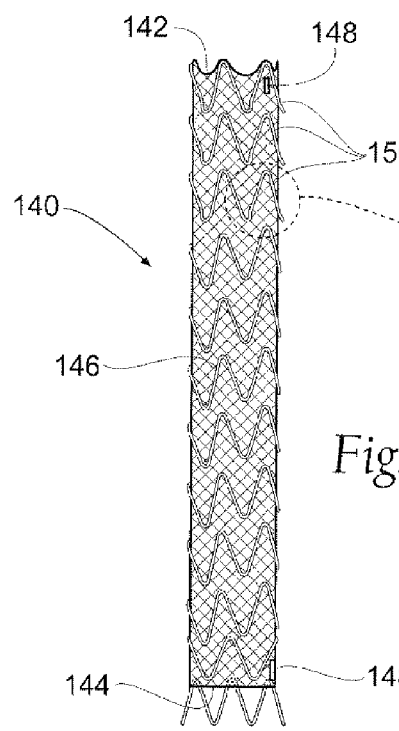
FIG. 9A is a side view of a prosthesis lumen extension.
Figure 9B:
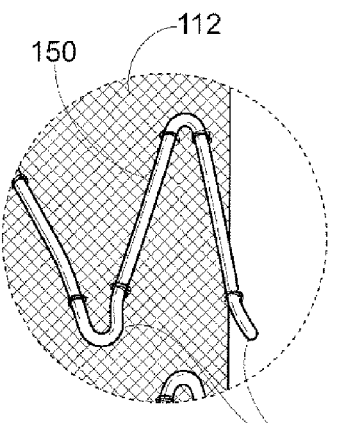
FIG. 9B is an enlarged view showing detail of the securing stent curved apices of the lumen extension shown in FIG. 9A.
Figure 9D:
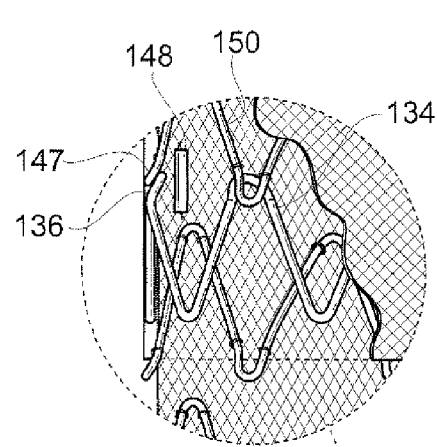
FIG. 9D is an enlarged view showing detail of the curved apices of both the securing stent of the lumen extension coupled to the distal stent of the main body prosthesis, as shown in FIG. 9C.
Figure 9C:
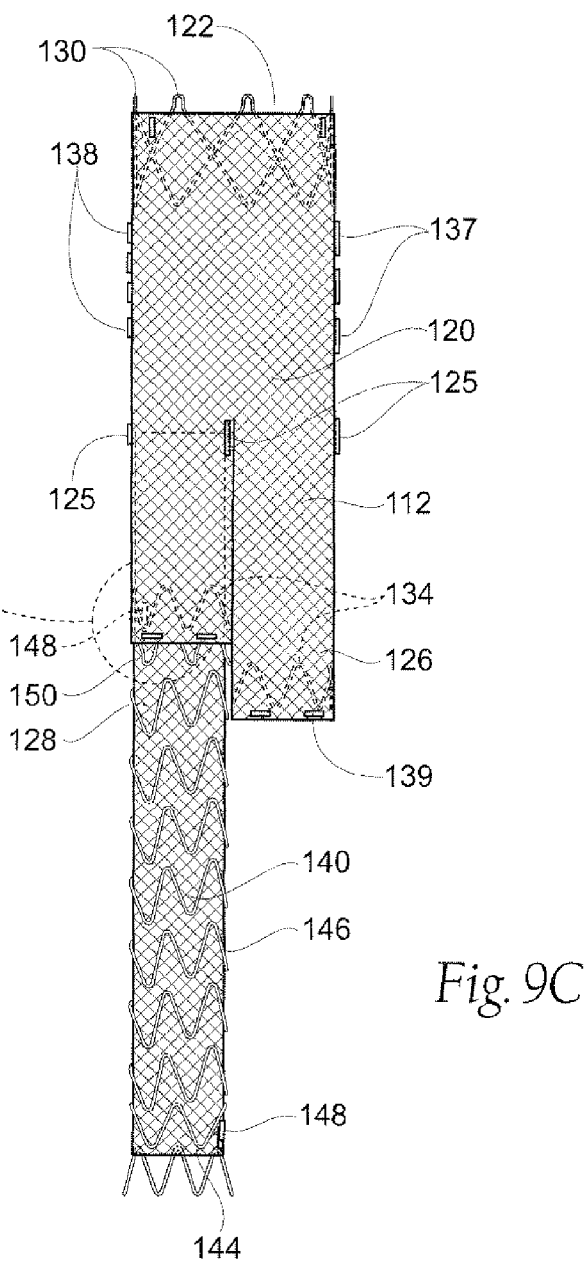
FIG. 9C is a side view of one extension lumen coupled to the main body component of the multi-lumen prosthesis.

In this arrangement, the multi-lumen prosthesis assembly 100 desirably includes a first and second flow channel lumen extension 140 (see FIG. 6). The first and second lumen extensions 140 desirably comprise the same construction, i.e., they are duplicates of each other. Referring to FIG. 9A, the lumen extension 140 includes a proximal end 142 that is sized and configured to be telescopically fitted within the first lumen 126 and/or the truncated second lumen 128 of the main body component 120. The distal end 144 of the lumen extension 140 is sized and configured to extend the reach of the first lumen 126 and the truncated second lumen 128 to another targeted destination or source spaced a defined distance from the main body component proximal opening 122. As a result, a portion of the extended second lumen 128 is joined to the first lumen 126 by the septum 124, and a portion of the extended second lumen 128 is not joined by the septum 124 to the lumen extension 140 of the first lumen 126.

Both the first lumen 126 and the truncated second lumen 128 of the main body component 120, which is joined by the septum 124 to the first lumen 126, provide an interface region or socket that is fully enclosed within the body of the main body component 120 itself. The first lumen 126 and the truncated second lumen 128 are therefore not prone to kinking or twisting or other kinds of movement independent of the main body component 120. Passage of a guide wire through the first lumen 126 or the second lumen 128 can occur unimpeded.

Being telescopically fitted within the interface region or socket and enclosed within the main body component 120, the mechanical properties of the lumen extension 140 are supplemented by the structural support and integrity of the main body component 120 itself, and vice versa. Coupled together, the main body component 120 and the lumen extension 140 provide enhanced resistance to migration and/or separation of the lumen extension 140 from the main body component 120. Seated within the enclosed interface region, the lumen extension 140 is peripherally sealed within the main body component 120 to resist leaks or seepage of fluids around the lumen extension 140. The septum 124 can be tapered, curved, wavy, or otherwise non-linear to enhance the connection between the lumen extension 140 and the main body component 120.

In one illustrated use (see FIG. 3), the main body component 120 can be deployed in the aorta in the region of the bifurcation of the first and second iliac, or ipsilateral and contralateral iliac arteries. When the main body prosthesis 120 is deployed, both the first lumen 126 and the second lumen 128 remains in communication with the aorta. After the main body component 120 is deployed, the first lumen extension 140 can be fitted within the distal opening 127 of the first lumen 126, and the second lumen extension 140 can be fitted within the distal opening 129 of the second lumen 128, so that the distal end 144 of the first extension 140 can be sized to reach into the first iliac of the bifurcation, while the distal end 144 of the second extension 140 can reach into the second iliac of the bifurcation (see FIG. 4). In this arrangement, the first lumen extension 140 of lumen 126 serves as a first lumen or ipsilateral lumen of the prosthesis 100, and the lumen extension 140 of the second lumen 128 serves as a second lumen or contralateral lumen.

The main body component 120 may include a proximal sealing stent 130 at its proximal end 108, which may extend beyond the prosthetic material 112 (see FIG. 7A). The proximal stent 130 orients the main body prosthesis 120 within the lumen and aids in maintaining the position of the main body prosthesis 120 in the aorta without obstructing the normal blood flow into the renal arteries. The proximal sealing stent 130 may be a self-expanding zigzag or diamond shaped stent, for example, and is desirably sewn inside the prosthesis material 112, although the stent may be outside, or may be wrapped between two layers of prosthesis material 112, for example.

Typically, this region of the aorta (proximal neck of the aneurysm just below the renal arteries) is also one area where one or more fasteners 402 may be introduced by a fastener device 400 to anchor the prosthesis 100 in place (see FIG. 4). However, it should be noted that other areas through out the main body 120 and lumen extensions 140 can also be fastened in place. It is desirable that this region of the main body component 120 be sized and configured for the receipt and retention of fasteners, e.g., the size and spacing of diamond or zigzag stent patterns to specially accommodate the placement of fasteners; and/or the use of woven fibers with an "X-pattern" or a "sinusoidal pattern" to specially accommodate placement of fasteners; and/or to fold over the prosthetic material 112 to form multiple layers, to reinforce the prosthesis in the region where fasteners 402 are placed; and/or the use of denser weave patters or stronger fibers from, e.g., Kevlar™ material or Vectran™ material or metallic wire woven alone or interwoven with typical polyester fibers in the region were fasteners are placed. It may also be desirable to fluoroscopically indicate this region of the prosthesis with radiopaque markers 132 on the prosthetic material 112 or proximal sealing stents 130 to aid in positioning the fastening devices.

Additional stents may be utilized throughout the main body component 120. Desirably, a minimal number of stents would be utilized within the main body component 120.

The multiple lumens 126 and 128 in the main body component 120 may typically be supported with distal stent rings 134 sewn or otherwise attached to the inside or outside of the prosthetic material 112. The proximal apices 136 of the stent rings 134 desirably are angled or curved inwardly (see FIG. 7B). The inward angle provides a retentive feature when the lumen extension 140 is positioned within a first or second lumen (see FIG. 10B). Alternative retentive features may also be used, such as hooks, barbs, loops of fabric or loops/folds of graft material or pockets in graft material, for example. Ideally, the distal stent rings 134 in one lumen 126 are staggered axially in position with the stent rings 134 in the other lumen 128, so that they do not overlap each other when the main body component 120 is radially compressed prior to deployment.

Rotational orientation of the main body component 120 within the vessel lumen or hollow body organ is accomplished with additional radiopaque markers 137 and 138 attached to the main body prosthesis 120 for visualization under fluoroscopy. Typically, these markers may be attached to the prosthetic material 112. Still, the markers 137 and 138 may be attached to the proximal sealing stent 130 or distal stent rings 134 instead of or in addition to the prosthetic material 112 to help fluoroscopically determine the location of all prosthesis openings. The radiopaque markers typically are in the form of marker bands, tight wound coils, or wire made from radiopaque materials such as platinum, platinum/iridium, tantalum, or gold for example.

Desirably, one or more markers 137, 138, are longer than the other, and are attached on opposite sides of the main body component 120 with the longer markers 137 aligned on the side with the first lumen 126 and the shorter markers 138 aligned on the side with the second lumen 128, for example. In an alternative embodiment the markers could be aligned with the septum. The markers 137 and 138 enable the clinician to determine the desired rotational orientation of the main body prosthesis 120 in the delivery system so that, upon deployment, the first distal opening 127 and the second distal opening 128 are aligned with the desired iliac arteries. The proximal markers 132 may also be included to enable the clinician to determine the position of the proximal end 108 of the main body component 120 in relation to the fixation point of the aorta. Additionally, distal markers 139 may be included to aid in the location of the distal openings 127, 129, and the insertion of the lumen extension 140. Insertion depth marker(s) 125 may be attached near the septum 124, or may be attached to the septum, or may be attached to the prosthesis material 112, for example, to indicate the location of and insertion depth for the lumen extension 140.

As previously described, the main body 120 (and the lumen extension 140) desirably utilizes a prosthetic material 112. The material 112 of the main body 120 may carry individual self-expanding, zigzag or diamond type stent rings, for example. The stent rings need not be attached to one another throughout the main body prosthesis 120. However, it may be desirable in certain locations within the prosthesis structure 120 to have attachments between the individual stent rings to provide stability and/or additional radial support.

As previously stated, the septum 124 is formed by sewing, heat bonding, stitching, or weaving opposing surfaces (i.e., the front and back) of the prosthetic material 112 of the main body component 120 together. In the region of the septum 124, the stent rings 134 extend from the septum 124 about the formed lumen, but do not enter or otherwise interrupt the septum 124 itself. The septum 124 is continuous and is formed separate from the supporting structure of stent rings 134.

The individual distal stent rings 134 allow for longitudinal main body prosthesis 120 compliance while maintaining radial support of the prosthesis lumens. This technical feature allows the prosthesis to more readily accommodate changes in vessel/aneurysm morphology.

The stents can be made, e.g., from Nitinol®. Still, other materials, manufacturing methods and designs can be used. Each of the stents may be sewn onto prosthetic material 112. In certain locations it is desired to have the stents attached to the outer diameter of the prosthetic material 112. Still, it is also contemplated that the stents could be attached to the inner diameter of the prosthetic material 112.

In the illustrated embodiment, the prosthetic material 112 is woven polyester, and the attachment of the stents is made with polyester suture. However, it is also contemplated that other attachment means could be utilized to secure the stents to the prosthetic material 112. These means include bonding; capturing the stents between two layers of prosthetic material 112; and incorporating the stents directly into the woven prosthetic material 112.

As seen in FIG. 9A, the lumen extension 140 has at least one spiral stent 146 positioned along at least a portion of the length of the extension and attached to the outside of prosthetic material 112 to provide stability and/or additional radial support. However, as in the main body component 120, it is contemplated that the stent 146 could also be placed on the inside of the prosthetic material 112, or the spiral stent 146 could be captured between two layers of prosthetic material (not shown). The prosthetic layer 112 could be a continuous tube or non-tubular. The prosthetic material 112 could cover the entire lumen extension 140 or the prosthetic material 112 could cover only a portion of the lumen extension. Furthermore, as previously discussed, the spiral stent 146 need not be one continuous stent along the length of the extension. The addition of the spiral stent 146 to the lumen extension 140 aids in the deployment of the lumen extension and allows for longitudinal compliance while maintaining radial support of the lumen within the lumen extension 140. Typically, radiopaque extension markers 148 are used on each end of the extension 140 to aid in the visualization of the placement of the lumen extension 140 within the lumen of the first distal opening 127 and the second distal opening 129 of the main body component 120.

As shown in FIGS. 9A through 9D, the engaging stent or stents 150 in the lumen extension 140 can be sized, configured, and arranged to engage the stent rings 134 in the first lumen 126 and the second lumen 128 of the main body 120. The distal apices 147 of at least one engaging stent 150 are angled outwardly to engage the mating distal stent 134 on the main body component 120 (seen particularly in FIGS. 9B and 9D). This engagement prevents the lumen extension 140 from moving or migrating axially in relation to the first lumen 126 and the second lumen 128 after the lumen extension 140 has been deployed. In an alternative embodiment shown in FIGS. 10A through 10D, the spiral stents 146, which are attached to the outside of the lumen extension 140, may engage with the distal stents 134 of the main body 120 without being angled outwardly. In either of these embodiments, additional features may be included with the main body 120 or the lumen extensions 140 to help prevent the lumen extension 140 from moving or migrating axially in relation to the main body 120, such as hooks, barbs, loops of fabric or loops/folds of graft material, or pockets in graft material, for example.

During use (see FIG. 58), the deployment catheter 200 is navigated over the guide wire 30 through an iliac to the desired location within the aorta near the renal arteries. The catheter 200 carries the main body component 120 of the multi-lumen prosthesis system 100 in a radially reduced configuration. At the targeted site, the retaining jacket 210 is retracted which allows the distal stent 134 of the second lumen 128 to radially expand into the position shown in FIG. 60. The distal stent 134 of the first lumen 126 and the proximal stent 130 are not allowed to expand until releasing means have been activated.

Figure 69:
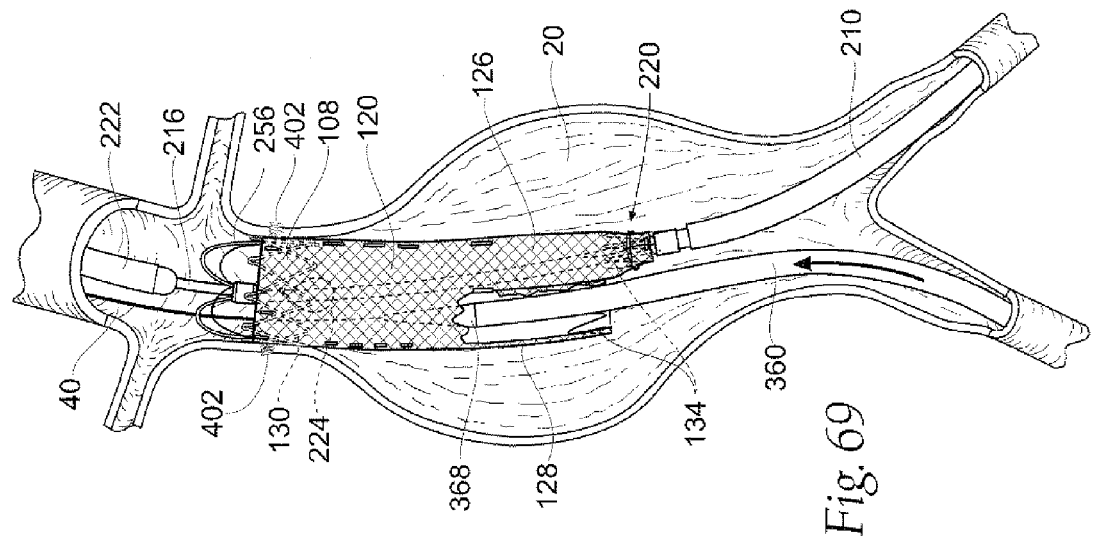
FIG. 69 is a perspective view of the deployment of a lumen extension component of the multi-lumen prosthesis within the aneurysm of FIG. 58, and showing the lumen extension catheter being positioned partially within a prosthesis lumen.
Figure 71:
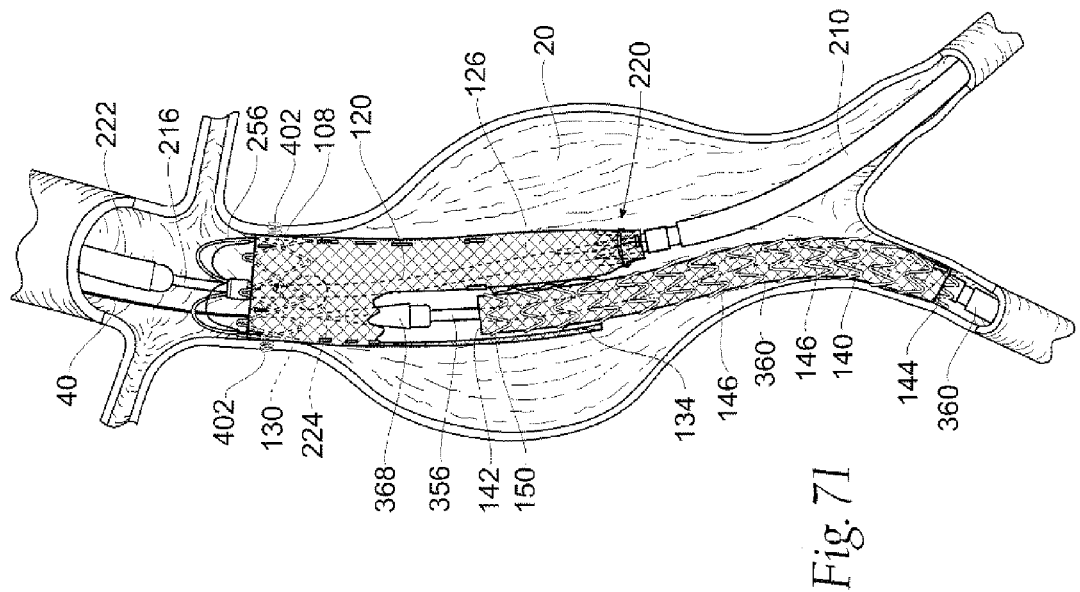
FIG. 71 is a perspective view of the deployment of the lumen extension component of the multi-lumen prosthesis within the aneurysm of FIG. 58, and showing the lumen extension coupled to and fully expanded within a lumen of the main body component after the release of the proximal retaining means.
Figure 70:
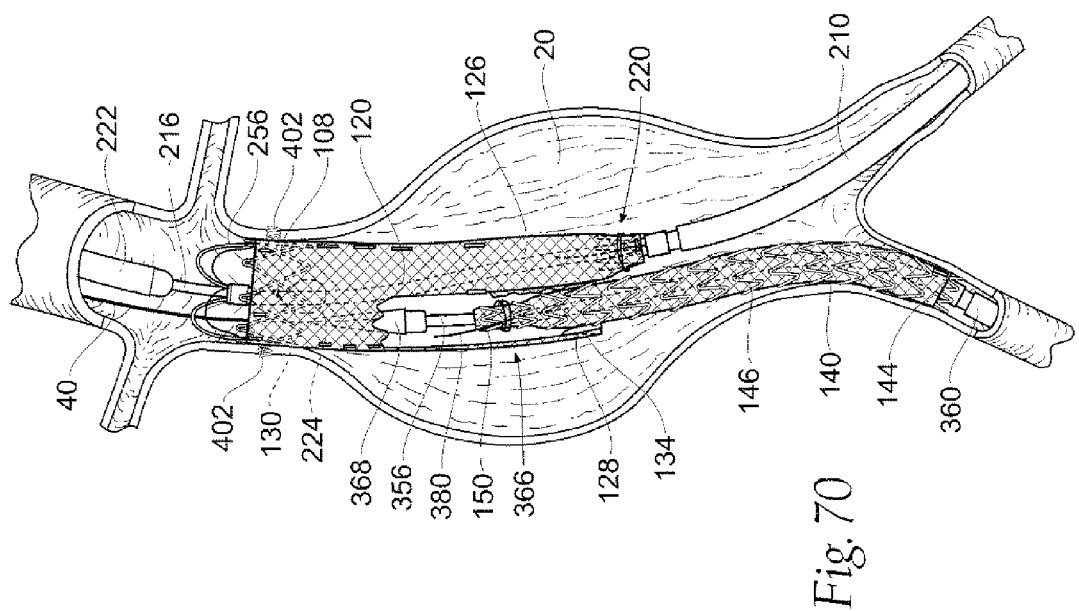
FIG. 70 is a perspective view of the deployment of the lumen extension component of the multi-lumen prosthesis within the aneurysm of FIG. 58, and showing the jacket retracted from the lumen extension deployment catheter and prior to the release of a proximal retaining means.
Figure 77:
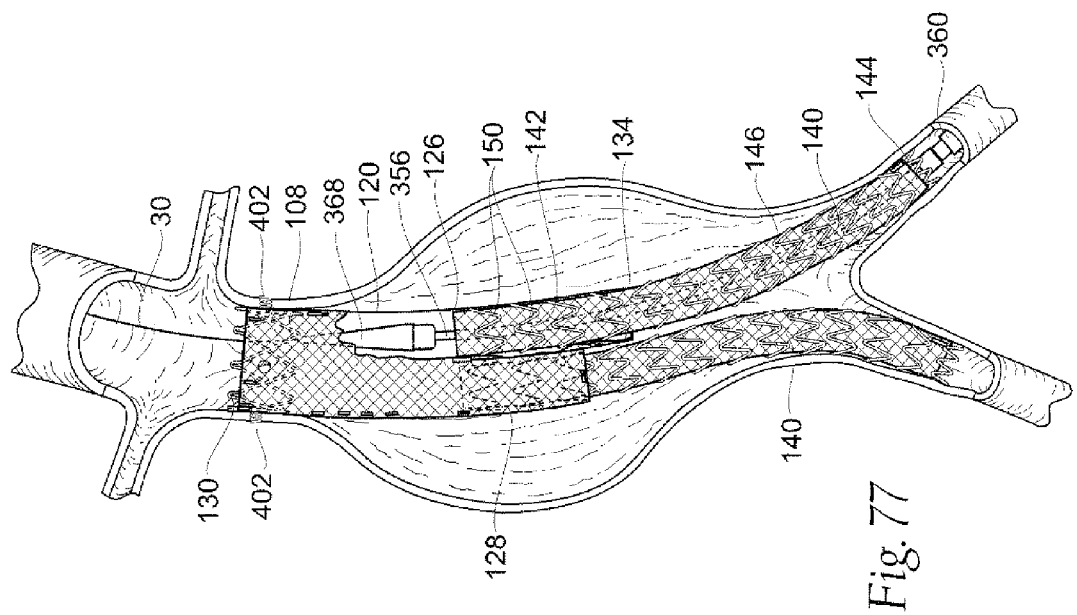
FIG. 77 is a perspective view of the deployment of the second lumen extension component of the multi-lumen prosthesis within the aneurysm of FIG. 58, and showing the second lumen extension coupled to and fully expanded within a lumen of the main body component after the release of the proximal retaining means.
Figure 78:
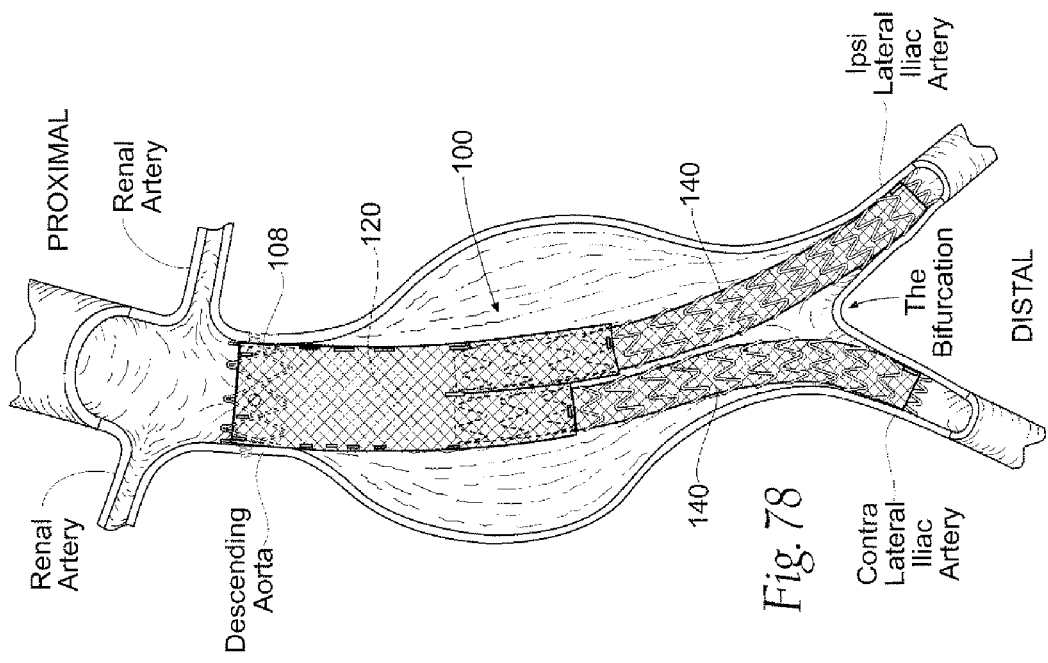
FIG. 78 is a perspective view of one embodiment of the completed deployment of the multi-lumen prosthesis within the aneurysm of FIG. 58.

As FIGS. 69 and 70 show, the first lumen extension 140 is carried in a radially compressed condition by an over-the-wire extension catheter 350 coming from the contralateral iliac, for example. The catheter 350 deploys the first lumen extension 140, such that the proximal end 142 of the lumen extension 140 is telescopically received within the second lumen 128 of the main body component 120 and the distal end 144 extends into the contralateral iliac, as FIG. 71 shows. The second lumen extension 140 is then carried in a radially compressed condition by the extension catheter 350 coming from the ipsilateral iliac, for example. The extension catheter 350 deploys the second lumen extension 140, such that the proximal end 142 of the lumen extension 140 is telescopically received within the first lumen 126 of the main body component 120 and the distal end 144 extends into the ipsilateral iliac, as FIG. 77 shows. Only when each lumen extension 140 is telescopically received within the first lumen 126 and second lumen 128 of the main body component 120, a bifurcated prosthesis 100 is formed with divergent lumens, as seen in FIG. 78.

IV. Implantation Apparatus

1. Prosthesis Deployment Catheter

Figure 11:
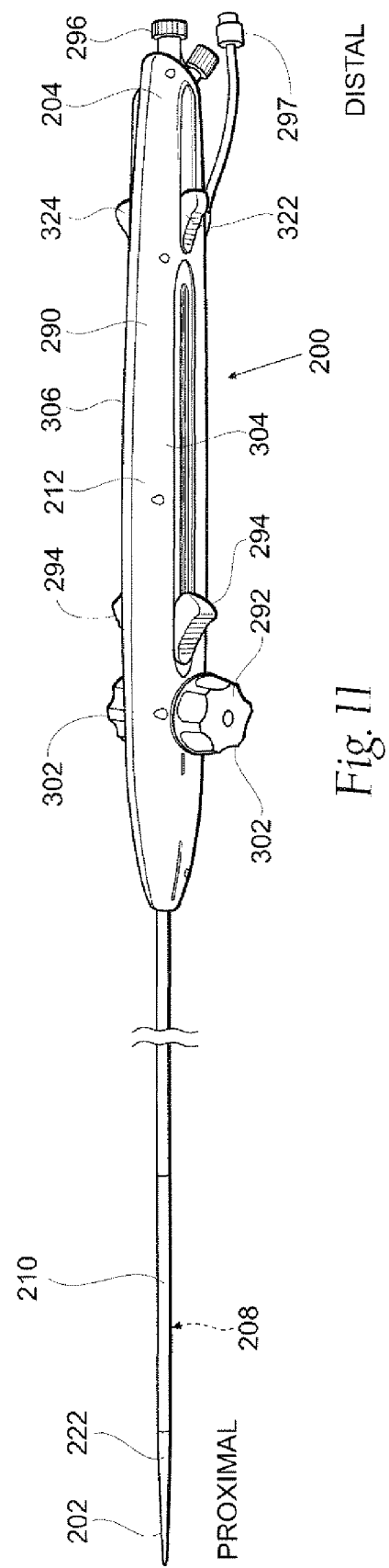
FIG. 11 is a perspective view of a prosthesis deployment catheter that embodies features of the invention.

FIG. 11 shows a prosthesis deployment catheter 200 having features of the invention. The purpose of the catheter 200 is to (i) contain and/or restrain the main body prosthesis 120 prior to its deployment (see FIG. 14A), (ii) deliver the main body prosthesis 120 through the vasculature to a desired location within the body, e.g., a hollow body organ or a blood vessel (see FIG. 1), and (iii) controllably deploy the main body prosthesis 120 in the desired location (see FIGS. 2 and 3), including maintaining a stable position of the main body prosthesis 120 in a partially deployed condition while the main body prosthesis is fastened to the vessel wall. In the illustrated embodiment, the proximal end 202 of the catheter 200 is shown positioned over a guide wire 30 in a body lumen (see FIG. 1). The catheter 200 carries the main body prosthesis 120 in a radially reduced configuration to the targeted site. At the targeted site, the catheter 200 releases the radially reduced prosthesis 120, which expands radially (see FIGS. 2 and 3). After partial or complete expansion or deployment of the main body prosthesis 120, one or more fasteners 402 are desirably introduced by a fastener device 400 to anchor the main body prosthesis 120 in place. The fasteners 402 may also serve to provide apposition of the prosthesis material 112 to the hollow body organ or vessel wall and to seal and/or repair a fluid leak. Further details of the fastener device and fastener can be found in section three (3) below.

As previously described, the prosthesis 100 can be sized and configured to be either straight or bifurcated form. FIG. 4 depicts a completely deployed bifurcated prosthesis 100. FIG. 5 depicts a completely deployed straight prosthesis 50.

For the purposes of illustration, FIG. 1 shows the targeted site as being within an abdominal aortic aneurysm. Of course, the targeted site can be elsewhere in the body.

As shown in FIGS. 11 through 14B, the catheter 200 comprises an inner assembly 208, an outer jacket 210, and a handle assembly 212. These components will now be individually described in greater detail.

A. The Inner Assembly

In the illustrated embodiment (see FIGS. 12 through 14B), the inner assembly 208 comprises a central shaft 216, which functions as a carrier for the main body prosthesis 120, proximal and distal retaining means 218, 220, and a catheter tip component 222. The proximal retaining means 218 desirably comprises a first proximal retaining means 224 and a second proximal retaining means 226. The first proximal retaining means 224 desirably retains at least a portion of the main body prosthesis 120 in a radially compressed, and/or partially radially expanded condition prior to deployment and prior to fastening the main body prosthesis 120 to the vessel wall. The second proximal retaining means 226 desirably functions to stabilize the deployed proximal sealing stent 130 by preventing longitudinal and to a limited extent rotational movement. Each of the first and second proximal retaining means also desirably include a co-acting releasing means or mechanism 228, 230 for maintaining the first or second proximal retaining means 224, 226 in a desired relationship with the main body prosthesis 120 prior to activation. The distal retaining means or mechanism 220 also desirably includes a releasing means or mechanism 232 for activating/releasing the distal retaining means or mechanism 220. The releasing means may comprise a wide variety of devices, such as wire or wires, sutures, magnetics, or fluids, and may include sliding, pulling or pushing, for example.

i. The Central Shaft

Figure 14A:
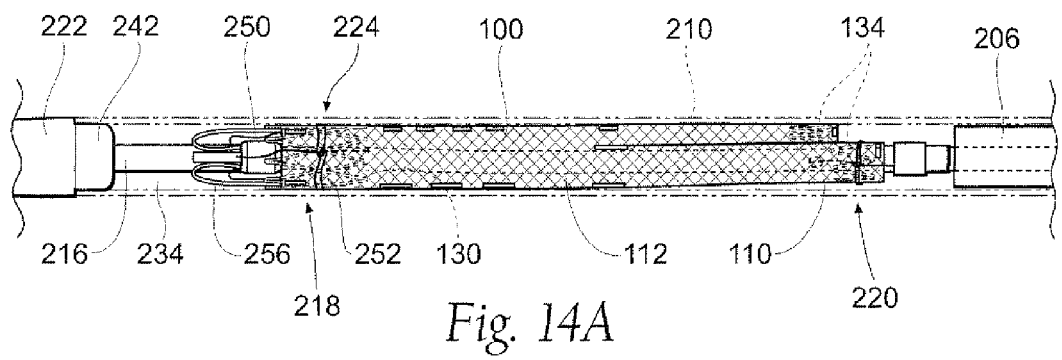
FIG. 14A is a side view of the proximal end of the deployment catheter of FIG. 11, and showing the jacket covering the main body component of the multi-lumen prosthesis prior to deployment.
Figure 14B:
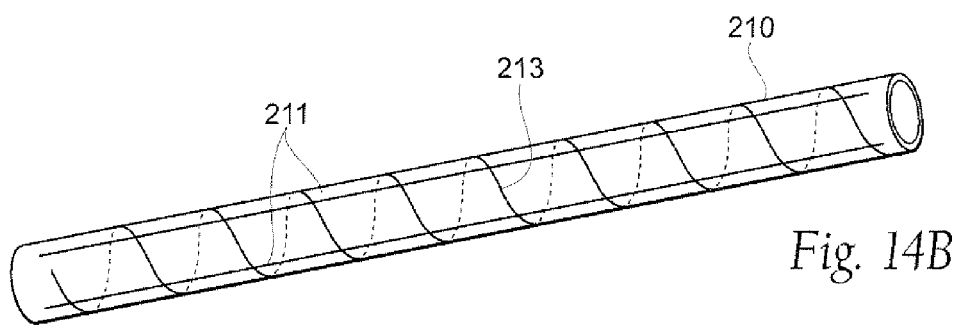
FIG. 14B is a perspective view of an alternative embodiment of the deployment catheter jacket of FIG. 11 showing structural reinforcement.

In the embodiment shown in FIGS. 13 and 14A, the central shaft 216 and the proximal and distal retaining means 218, 220 are located within the confines of the outer jacket 210. In this respect, the outer jacket 210 functions as an enclosure for the main body prosthesis 120 on the carrier (see FIG. 14A). In this arrangement, the catheter tip component 222 is attached to the proximal end of the central shaft 216, and the proximal end of the outer jacket 210 terminates adjacent the catheter tip component 222. Thus, the catheter tip component 222 extends outward beyond the outer jacket 210. The central shaft 216, the proximal and distal releasing means 228, 230, 232, and the outer jacket 210 may be coupled to the handle assembly 212 at the proximal end of the catheter handle assembly 212 (see FIG. 11). As can be seen in FIG. 14A, the main body prosthesis 120 is contained in a cavity 234 defined between the central shaft 216 and the outer jacket 210 in the proximal section of the deployment catheter 200.

The central shaft 216 extends from the handle assembly 212 to the catheter tip component 222. The central shaft 216 may be made, e.g., from stainless steel or other suitable medical materials including other metals or polymers. The central shaft 216 comprises at least one lumen, desirably more than one lumen, and more desirably four lumens.

Figure 15:
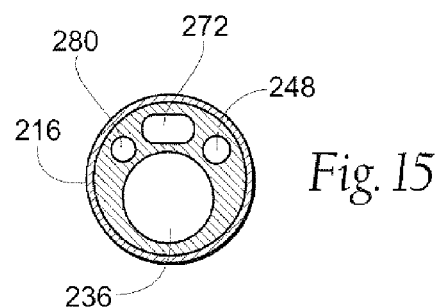
FIG. 15 is a section view of the lumens in the central shaft deployment catheter taken generally along line 15-15 of FIG. 12.

One lumen may be described as the central lumen 236 (see FIG. 15), with an inner diameter between 0.010 and 0.120 inches, desirably between 0.020 and 0.060 inches and most desirably between 0.030 and 0.050 inches. As described, the central lumen 236 allows for the insertion of the guide wire 30 up to 0.038" diameter. The catheter tip component 222 also desirably has at least one lumen 238 (see FIG. 16) configured to align with at least one lumen within the central shaft 216. This lumen 238 allows for the insertion of the guide wire 30 through the central shaft 216 and through the catheter tip component 222. Typically this lumen 238 will have an inner diameter between 0.010 and 0.120 inches, desirably between 0.020 and 0.060 inches and most desirably between 0.030 and 0.050 inches.

ii. Catheter Tip

Desirably, the catheter tip component 222 is flexible and has a long, tapered proximal end 240 and a shorter, tapered distal end 242. The maximum diameter of the catheter tip component 222 is approximately the same as the outside diameter of the proximal end of the outer jacket 210. The proximal end 240 of the catheter tip component 222 provides a smooth tapered transition from the lumen 238 containing the guide wire 30 to the proximal edge of the outer jacket 210. This feature aids in catheter insertion and navigation through tortuous anatomy over the guide wire 30. The tapered section on the distal end 242 of the catheter tip component 222 prevents the catheter tip component 222 from inadvertently engaging the main body prosthesis 120, portions of the surrounding anatomy, or an introducer sheath or the like during removal of the deployment catheter 200 from the body.

iii. Proximal Retaining Means a. First Proximal Retaining Means

Figure 19:
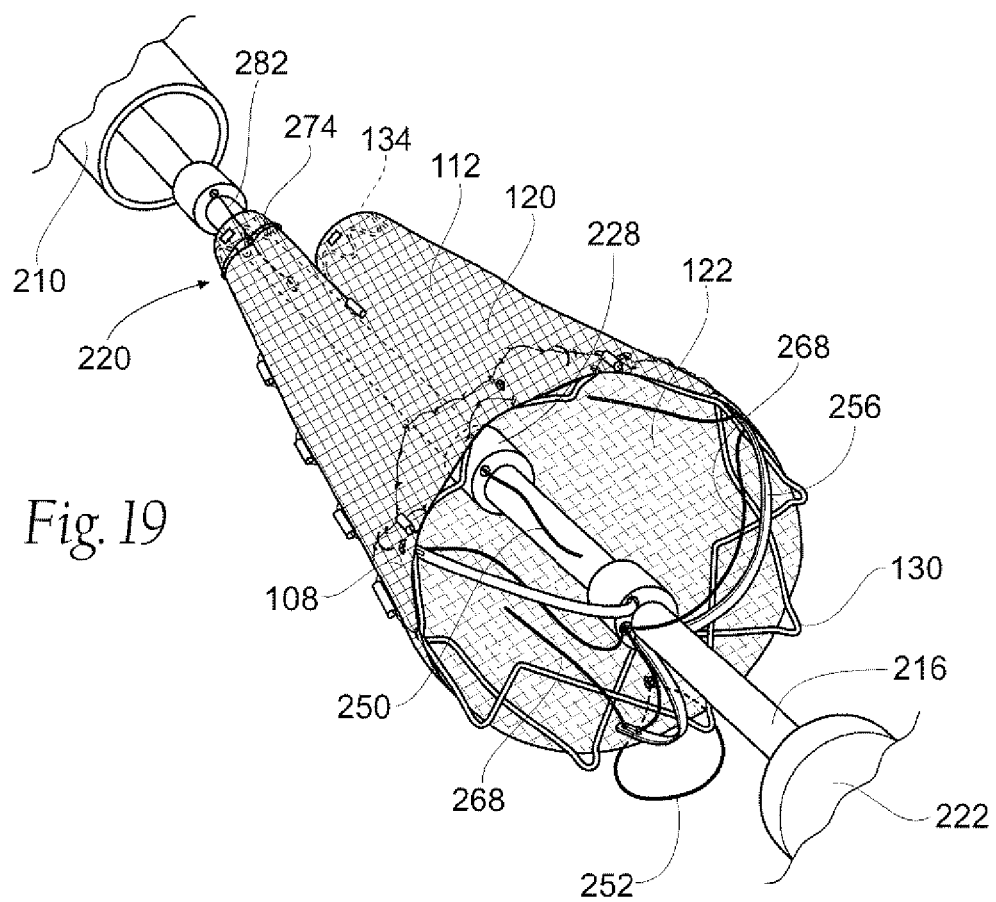
FIG. 19 is a perspective view of the main body component of the multi-lumen prosthesis positioned on the proximal end of the deployment catheter showing the first proximal retaining means released and the proximal end of the main body component expanded.

As can be seen in FIGS. 17 through 19, in the illustrated embodiment, the first proximal retaining means 224 comprises at least one suture, or sutures, 252 and/or equivalent structures, which are coupled to the prosthetic material 112, or one or more stents 130 on the main body prosthesis 120. The suture 252 is, in turn, looped around the releasing means 228, e.g., a release wire 250, when the release wire 250 is in its proximal-most position, as FIGS. 17 and 18A shows. Distal retraction of the wire 250 withdraws the wire 250 from the suture loop 252, and allows the proximal end 108 of the main body prosthesis 120 to radially expand, as FIG. 19 shows. In an alternative embodiment, the suture 252 may comprise more than one suture, i.e., two or more suture loops. FIG. 18B shows the path of two suture loops 252 looped around the release wire 250.

Belt loops or the like may be provided on the main body prosthesis 120 and/or lumen extensions 140 to guide and support the suture loop(s) along the path of the suture loop (see FIGS. 17 and 46B for example). The belt loops can be spaced at desired circumferential intervals, such as every ninety degrees, for example.

In the illustrated embodiment, one end of the suture loop 252 is coupled to the prosthetic material 112 or one or more stents 130 at or near the proximal end 108 of the main body prosthesis 120. The suture loop 252 is then looped around the main body prosthesis 120 and the releasing means 228 in a predetermined pattern, as shown in FIG. 18A, in order to compress and retain the proximal end 108 of the prosthesis 120. The free end of the suture loop 252 is then coupled to the prosthetic material 112 or one or more stents 130 at or near the proximal end 108 of the main body prosthesis 120. FIG. 18B shows two separate loops 252 looped around the main body prosthesis 120 and the release wire 250. It should be appreciated, however, that suture loop 252 could be coupled to stents elsewhere in the main body prosthesis 120, and/or the other components of the main body prosthesis 120 as well.

The suture loop 252 and releasing means 228, e.g., release wire 250, of the embodiment just described retains the prosthesis 120 in a desired relationship to the central shaft (see FIG. 17). The suture loop 252 and the releasing means 228 help to keep the main body prosthesis 120 from moving distally as the outer jacket 210 is retracted. The suture loop 252 also keeps the stent or stents 130 that are retained by the suture loop 252 in a radially compressed condition as the outer jacket 210 is retracted. The suture loop 252 and releasing means 228 prevent the proximal end 108 of the main body prosthesis 120 from self-expanding until the releasing means 228 has been withdrawn. In the illustrated embodiment, the withdrawal of the releasing means 228 is accomplished by operating a control knob to move the releasing means 228 distally, withdrawing the releasing means 228 away from the suture loop 252. Once the releasing means 228 is withdrawn, the restrained components of the main body prosthesis 120 are free to self expand, as FIG. 19 shows.

Figure 20:
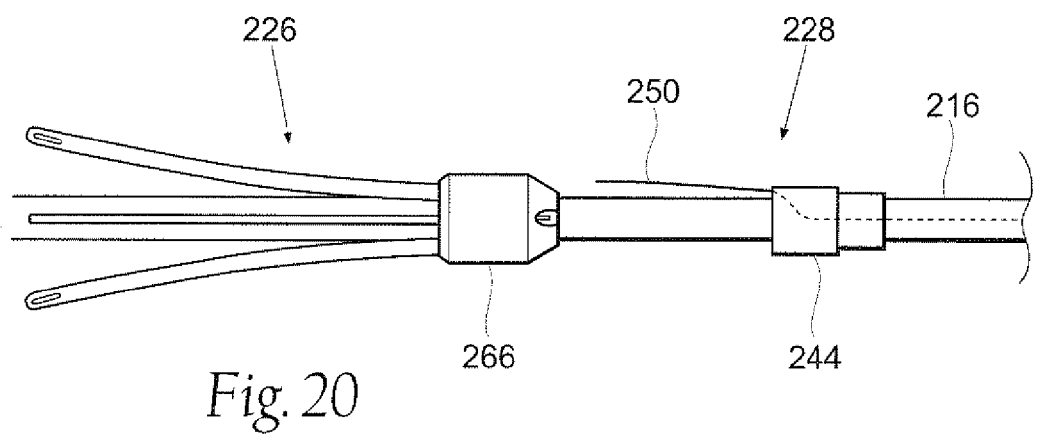
FIG. 20 is a side view of a portion of the distal end of the deployment catheter showing one embodiment of a first proximal releasing means and a first proximal release wire.
Figure 21:
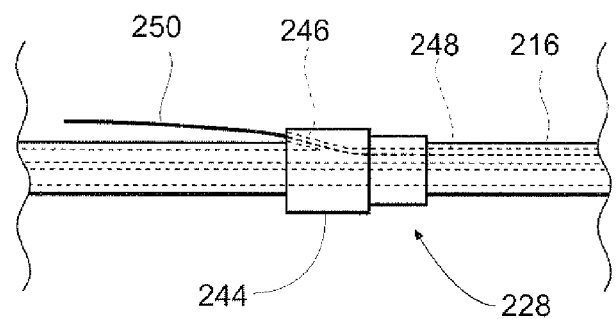
FIG. 21 is a side view of a portion of the proximal end of the deployment catheter showing detail of the first proximal release hub and central shaft lumens.
Figure 22:
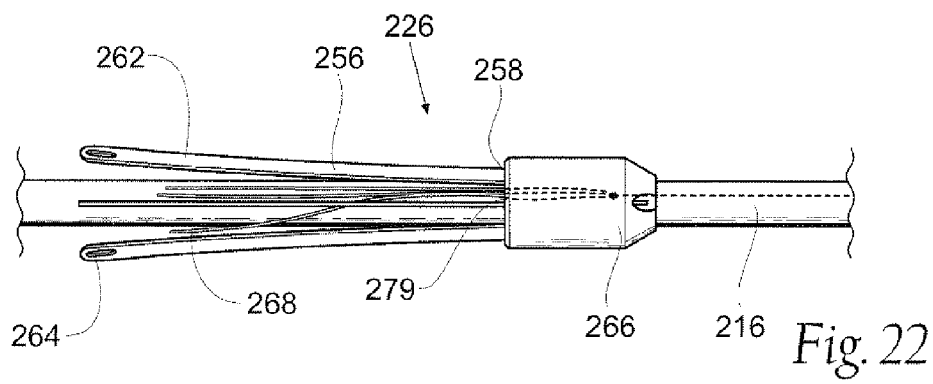
FIG. 22 is a side view of a portion of the distal end of the deployment catheter showing detail of one embodiment of the second proximal releasing means.
Figure 23:
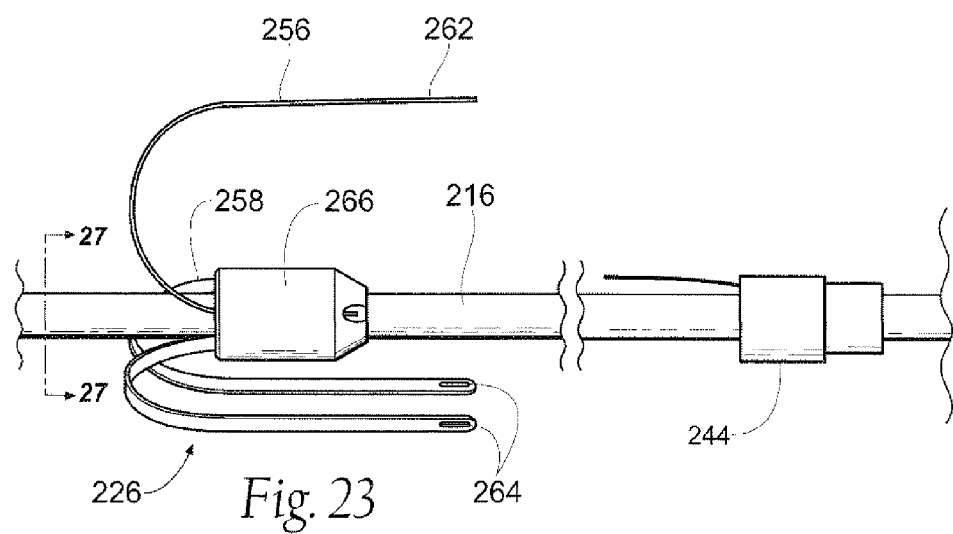
FIG. 23 is a side view showing detail of the stabilizing arms in a pre-deployment configuration, the proximal ends of the stabilizing arms being arched back generally toward a first proximal release hub.

As can be seen in FIGS. 20 and 21, the first proximal releasing means 228 comprises a first proximal release hub 244 positioned over the central shaft 216, and a release wire 250. The first proximal release hub 244 may include a small hole or lumen 246 in the proximal end of the hub 244 that is in fluid communication with a first proximal release lumen 248 within the central shaft 216. Each lumen 246, 248 desirably includes a diameter sufficiently large to accommodate the first proximal release wire 250 extending from the handle assembly 212 to beyond the first proximal release hub 244. It is to be appreciated that the release wire 250 may extend external the shaft 216 as well.

The first proximal retaining means 224 holds the main body prosthesis 120 in a desired configuration prior to deployment (see FIGS. 17 and 18A) and the first proximal releasing means 228 selectively releases the main body prosthesis 120 for the first stage of deployment (see FIG. 19). In the illustrated embodiment, the distal end of the first proximal release wire 250 is connected to an actuator or control button or knob in the handle assembly 212, as will be described further below.

The main body prosthesis 120 is retained by at least the first proximal retaining means 224 along the central shaft 216 in the cavity 234, which extends between the distal end 242 of the catheter tip component 222 and the proximal end of a spacer 206 (as best seen in FIG. 14A). In the illustrated embodiment, the releasing means 228 includes the release wire 250 that may extend through at least a portion of the central shaft 216. The proximal end of the wire 250 passes through the lumen 246 of the first proximal release hub 244. The first proximal release wire 250 is thereby kept in a desired relationship within or along the central shaft 216. The distal end of the first proximal release wire 250 is coupled to the control knob, such that fore and aft movement of the knob moves the release wire 250, respectively, proximally and distally.

As illustrated and described, the first proximal releasing means 228 is coupled to one restrained component of the main body prosthesis 120, i.e., suture loop 252. It should be appreciated, however, that the releasing means 228 can be coupled to the main body prosthesis 120 at two or more restrained regions, so that withdrawal of the releasing means 228 frees the prosthesis at two or more restrained regions. It should also be appreciated that the releasing means 228 can comprise more than a single releasing element. For example, multiple, individual releasing wires 250 could be coupled to the main body prosthesis 120 at different regions, so that release of separate regions of the main body prosthesis 120 can be individually controlled.

b. Second Proximal Retaining

Means

Referring back to FIG. 12, the proximal retaining means 218 may also incorporate a second retaining means 226 which may function in cooperation with, or separate from the first proximal retaining means 224. The second proximal retaining means 226 may be held in place by the second proximal releasing means 230 in a predetermined, spaced relationship with the central shaft 216.

Referring now to FIGS. 22 through 27, the second proximal retaining means 226 may comprise at least one stabilizing arm 256, and/or equivalent structures, and desirably more than one stabilizing arm, such as three stabilizing arms, as shown. The second proximal releasing means 226 may comprise a second proximal release hub 266 and a second proximal release wire or wires 268.

The distal ends 258 of the stabilizing arms 256 are coupled to the second proximal release hub 266. In a pre-deployment configuration, the proximal ends 262 of the stabilizing arms 256 are arched back generally toward the first proximal release hub 244 (see FIGS. 23 and 24) and are releasably attached to the prosthesis material 112 at or near the proximal end 108 of the main body prosthesis 120 (see FIGS. 24 and 25). In a post-deployment configuration, as seen in FIG. 26, the stabilizing arms 256 extend proximally toward the catheter tip 222.

Figure 25:
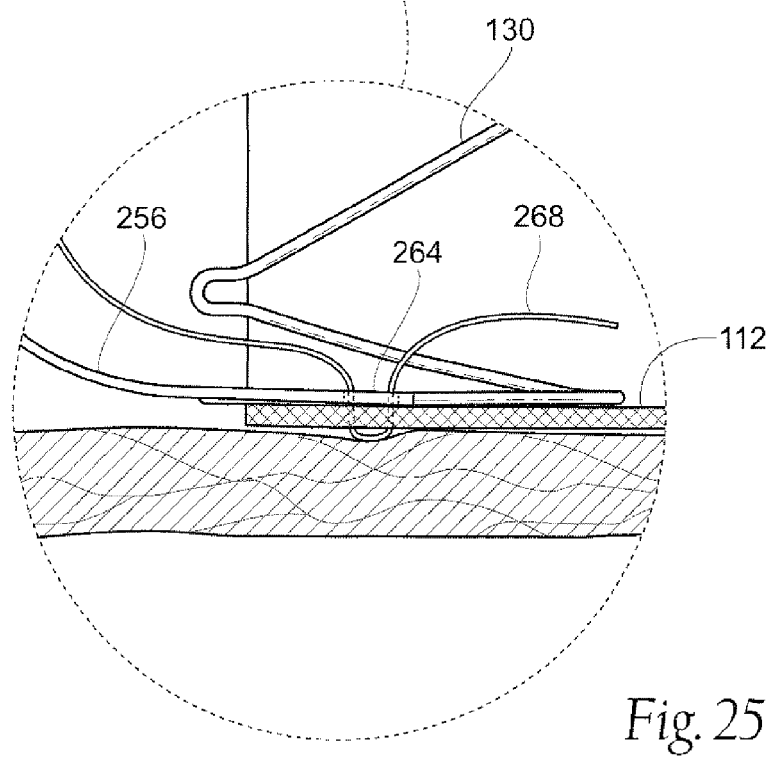
FIG. 25 is a side view showing detail of stabilizing arms coupled to the proximal end of the main body prosthesis, showing the second proximal release wire stitched or otherwise extended through a stabilizing arm aperture and through the prosthesis material, releasably securing the stabilizing arms to the main body prosthesis.

The proximal ends 262 of the stabilizing arms 256 include a stabilizing arm aperture 264. In the pre-deployment configuration, the stabilizing arms 256 are positioned within the proximal opening 122 of the main body prosthesis 120 and the second proximal release wire 268 is stitched or otherwise extended through the stabilizing arm aperture 264 and through the prosthesis material 112, releasably securing the stabilizing arms 256 to the main body prosthesis 120 (as best seen in FIG. 25). Distal retraction of the second proximal release wire 268 (using a second control knob, to be described later) withdraws the second proximal release wire 268 from the prosthesis material 112 and releases the stabilizing arms 264. The main body prosthesis 120 is now free from the retentive feature of the stabilizing arms 256, and the stabilizing arms return to the post-deployment configuration, as shown in FIG. 26. It is to be appreciated that the second proximal release wire 268 may comprise multiple release wires, including one release wire for each stabilizing arm 256. The second proximal release wire 268 may comprise a single wire extending through the central shaft, and then divide into multiple wires to individually engage the stabilizing arms, or the release wire 268 may comprise multiple wires extending through the central shaft 216 to individually engage each stabilizing arm 256. In an alternative embodiment, the stabilizing arms 256 could be positioned in the reverse orientation on the catheter central shaft 216. Stabilizing arms of this configuration would be biased open away from the central shaft 216 and would require a secondary means to retain them in close proximity to the central shaft 216 in order to be rejacketed before catheter removal.

In the embodiment shown in FIGS. 24 through 27, the second proximal retaining means 226 includes a second proximal release hub 266 positioned over the central shaft 216. The second proximal release hub 266 may include a small hole or lumen 270 in the proximal end of the hub 266 that is in fluid communication with the second proximal release lumen 272 within the central shaft (see FIGS. 24 and 27). The lumen 270 and 272 desirably includes a diameter sufficiently large to accommodate at least one second proximal release wire 268 extending from the handle portion 212 to beyond the second proximal release hub 266. It is to be appreciated that the release wire 268 may extend external the shaft 216 as well.

Figure 26:
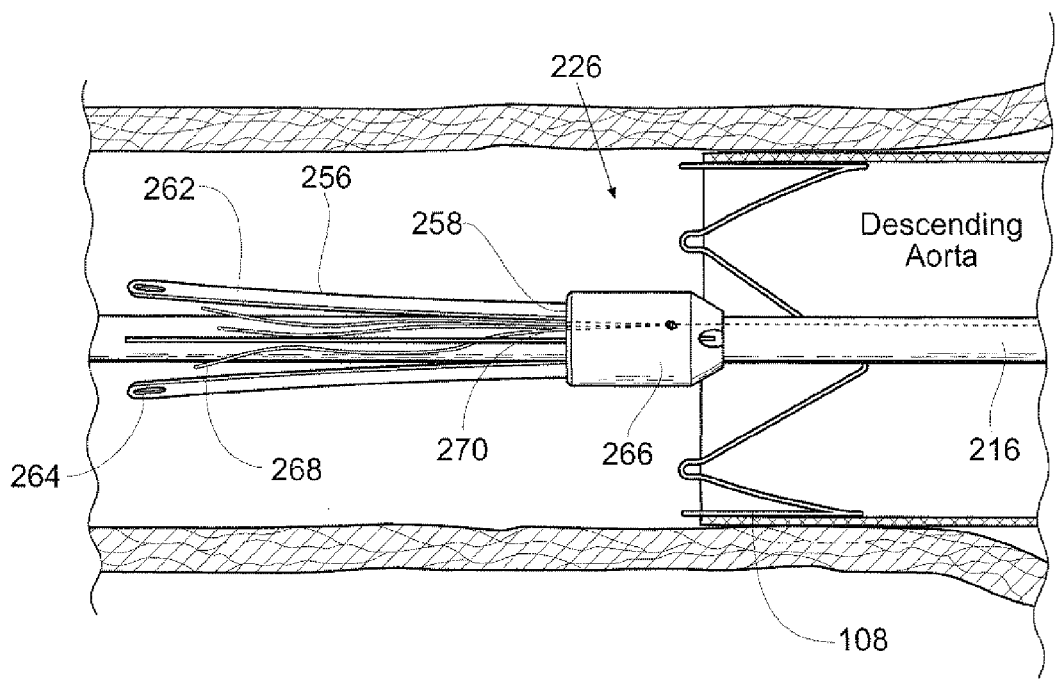
FIG. 26 is a side view of the stabilizing arms of FIG. 23 in a post-deployment configuration with the deployment catheter and multi-lumen prosthesis positioned within the descending aorta, and showing the proximal ends of the stabilizing arms released from the proximal end of the main body prosthesis.
Figure 27:
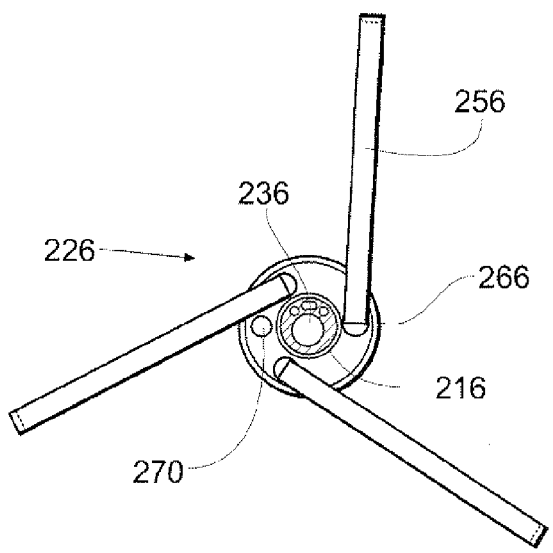
FIG. 27 is a section view of the proximal end of the deployment catheter shaft taken generally along line 27-27 of FIG. 23.

The second proximal retaining means 226 holds the main body prosthesis 120 in a desired con figuration prior to deployment (see FIGS. 19 and 24) and selectively releases the main body prosthesis 120 for the second stage of deployment (see FIG. 26). In the illustrated embodiment, the distal end of the second proximal release wire 268 is connected to an actuator or control button or knob in the handle assembly 212, as will be discussed further below.

Figure 24:
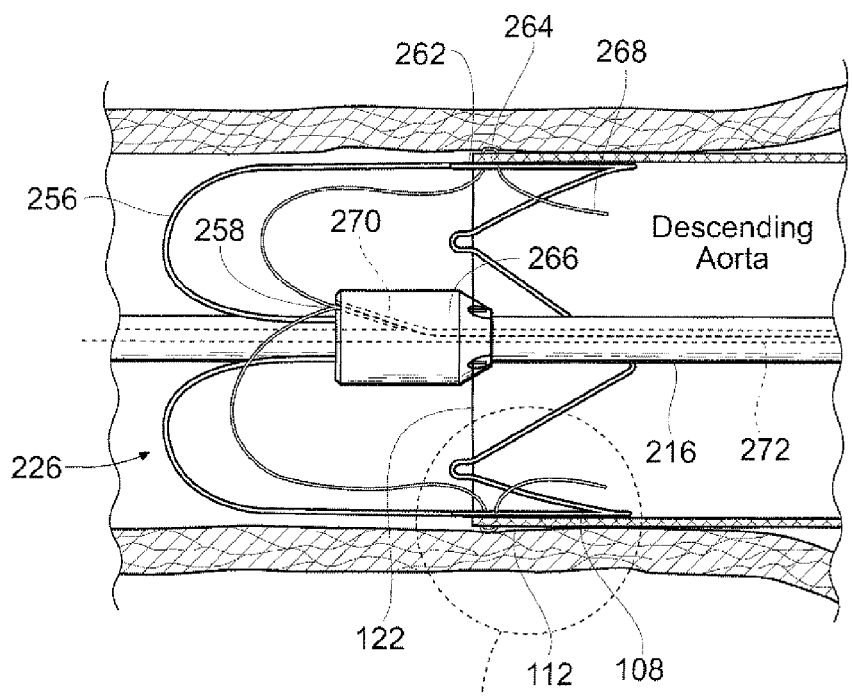
FIG. 24 is a side view of the stabilizing arms of FIG. 23 in a pre-deployment configuration with the deployment catheter and multi-lumen prosthesis positioned within the descending aorta, and showing the proximal ends of the stabilizing arms coupled to the proximal end of the main body prosthesis.

The main body prosthesis 120 is retained by the second proximal retaining means 226 in a spaced apart relationship to the central shaft 216 (see FIG. 24). In the illustrated embodiment, the second proximal releasing means 230 includes the second proximal release wire 268 that may extend through at least a portion of the central shaft 216. The proximal end of the release wire 268 passes through the lumen 270 of the second proximal release hub 266. The second proximal release wire 268 is thereby kept in a desired relationship within or along the central shaft 216. The distal end of the second proximal release wire 268 is coupled to the second control knob, such that fore and aft movement of the second knob moves the second proximal release wire 268, respectively, proximally and distally.

iv. Distal Retaining Means

Figure 28:
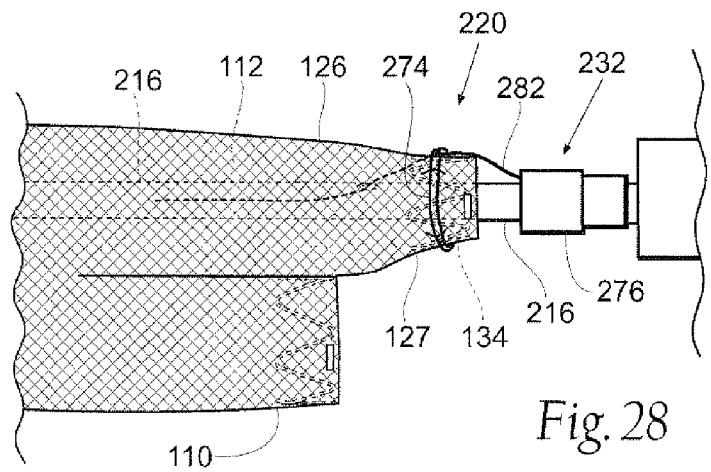
FIG. 28 is a side view of the distal end of the main body prosthesis positioned on the deployment catheter central shaft prior to deployment of the distal retaining means.
Figure 29A:
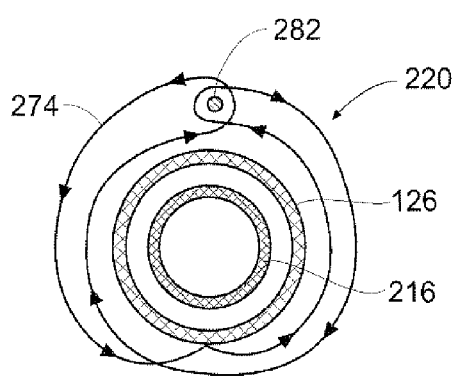
FIG. 29A is a side view of one embodiment of a suture loop path around the distal end of the multi-lumen prosthesis.
Figure 29B:
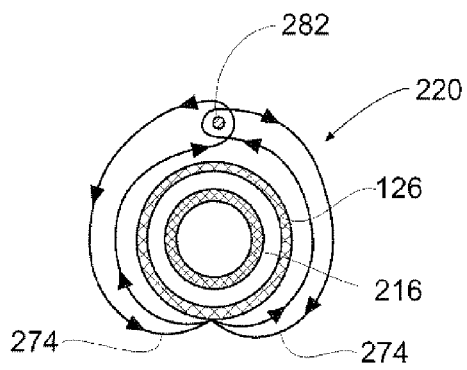
FIG. 29B is a side view of an alternative embodiment of a suture loop path around the distal end of the multi-lumen prosthesis of FIG. 29A, showing multiple suture loops.
Figure 30:
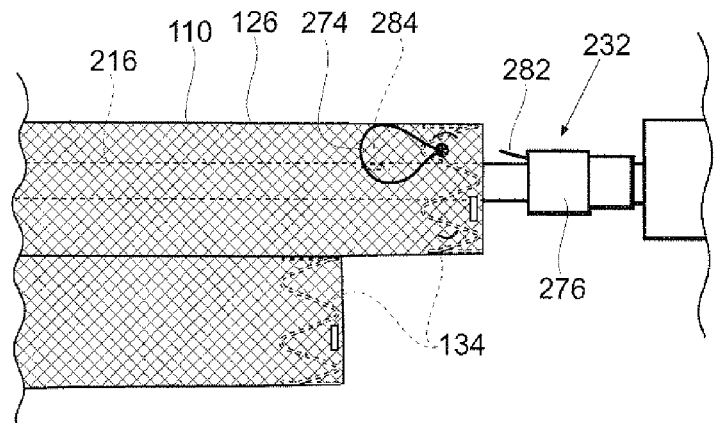
FIG. 30 is a side view of the distal end of the main body component of the multi-lumen prosthesis positioned on the deployment catheter shaft of FIG. 28, showing the distal retaining means released and the distal end of the main body component expanded.
Figure 31:
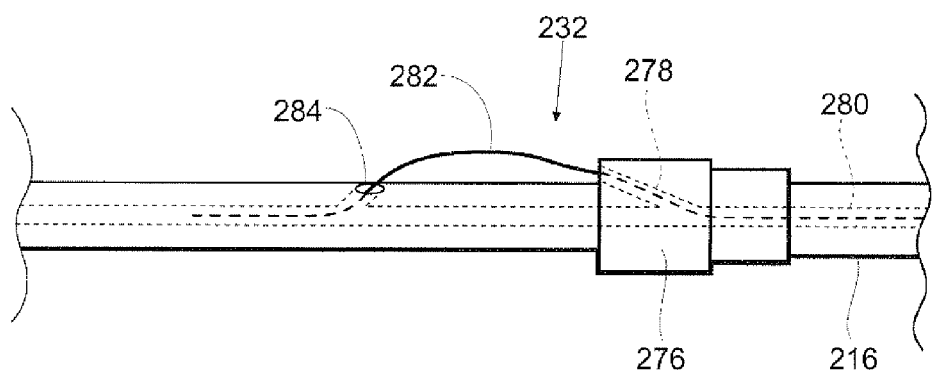
FIG. 31 is a side view of a portion of the proximal end of the deployment catheter showing detail of the distal releasing means and central shaft lumens.

As can be seen in FIGS. 28 through 33, in the illustrated embodiment, the distal retaining means 220 comprises at least one suture, or sutures, 274 and/or equivalent structures, which are coupled to the prosthetic material 112, or one or more stents 134 on the main body prosthesis 120. Desirably, the suture 274 is coupled to the prosthesis material 112 near the distal end 110 of the main body 120, and more desirably near the distal opening 127 of the first lumen 126. The suture 274 is, in turn, looped around the releasing means 232, e.g., a release wire 282, when the release wire 282 is in its proximal-most position, as FIGS. 28 and 29A show. Distal retraction of the wire 282 withdraws the wire 282 from the suture loop 274, and allows the distal end 110 of the main body prosthesis 120 to radially expand, as FIG. 30 shows. In an alternative embodiment, the suture 274 may comprise more than one suture, i.e., two or more suture loops. FIG. 29B shows the path of two suture loops 252 looped around the release wire 292.

As described for the first proximal retaining means, belt loops or the like may be provided on the main body prosthesis 120 and/or lumen extensions 140 to guide and support the suture loop(s) along the path of the suture loop. The belt loops can be spaced at desired circumferential intervals, such as every ninety degrees, for example.

In the illustrated embodiment, one end of the suture loop 274 is coupled to the prosthetic material 112 or one or more stents 134 at or near the distal end 110 of the main body prosthesis 120. The suture loop 274 is then looped around the main body prosthesis 120 and the distal releasing means 232 in a predetermined pattern, as shown in FIG. 29A, in order to compress and retain the distal end 110 of the main body prosthesis 120. The free end of the suture loop 274 is then coupled to the prosthetic material 112 or one or more stents 134 at or near the proximal end 110 of the main body prosthesis 120. FIG. 29B shows two separate loops 252 looped around the main body prosthesis 120 and the release wire 250. It should be appreciated, however, that suture loop 274 could be coupled to stents elsewhere in the main body prosthesis 120, and/or the other components of the main body prosthesis 120 as well.

The suture loop 274 and releasing means 232, e.g., release wire 282, of the embodiment just described retain the distal end of the main body prosthesis 120 to the central shaft 216 (see FIG. 28). The suture loop 274 and the releasing means 232 keep the main body prosthesis 120 from moving distally as the outer jacket 210 is retracted. The releasing means 232 also keeps the stent or stents 134 that are retained by the suture loops 274 in a radially compressed condition as the outer jacket 210 is retracted. The suture loop 274 and releasing means 232 prevent the distal end 110 of the main body prosthesis 120 from self-expanding until the releasing means 232 has been withdrawn. In the illustrated embodiment, the withdrawal of the releasing means 232 is accomplished by operating a control knob to move the releasing means 232 distally, withdrawing the releasing means 232 and away from the suture loop 252. Once there leasing means 232 is withdrawn, the restrained components of the main body prosthesis 120 are free to self expand, as FIG. 30 shows.

In the embodiment shown in FIGS. 28 through 31, the distal releasing means 232 includes a distal release hub 276 positioned over the central shaft 216 and a release wire 282. The distal release hub may include a small hole or lumen 278 in the proximal end of the hub that is in fluid communication with a distal release lumen 280 within the central shaft 216 (see FIG. 31). Each lumen 278, 280 desirably includes a diameter sufficiently large to accommodate a distal release wire 282 extending from the handle assembly 212 to beyond the distal release hub. It is to be appreciated that the release wire 282 may extend external to the shaft 216 as well.

The distal retaining means 220 holds the distal end 110 of the main body prosthesis 120 in a desired configuration prior to deployment of the distal end (see FIG. 28) and the distal releasing means 232 selectively releases the distal end 110 of the main body prosthesis 120 for the final stage of deployment (see FIG. 30). In the illustrated embodiment, the distal end of the distal releasing means 232 is connected to an actuator or control button or knob in the handle assembly 212, as will be described further below.

In the illustrated embodiment, the distal releasing means 232 includes the distal release wire 282 that may extend through at least a portion of the central shaft 216. The proximal end of the wire 282 passes through the lumen 278 of the distal release hub 276. The proximal end of the distal release wire 282 then may extend back into the central shaft 216 through the second distal release hole or lumen 284 positioned spaced apart from the distal release hub 276. The proximal end of the release wire 282 is thereby kept in a desired relationship within or along the central shaft 216. The distal end of the distal release wire 282 is coupled to the distal control knob, such that fore and aft movement of the distal control knob moves the distal release wire 282, respectively, distally and proximally.

As illustrated and described, the distal releasing means 232 is coupled to the main body prosthesis 120 or a component of the main body prosthesis, i.e., suture loop 274. It should be appreciated, however, that the distal releasing means 232 can be coupled to the main body prosthesis 120 at two or more restrained regions, so that withdrawal of the distal releasing means 232 frees the prosthesis at two or more restrained regions. It should also be appreciated that the distal releasing means 232 can comprise more than a single releasing element. For example, multiple, individual releasing wires 282 could be coupled to the main body prosthesis 120 at different regions, so that release of separate regions of the distal end of the main body prosthesis 120 can be individually controlled.

Figure 32:
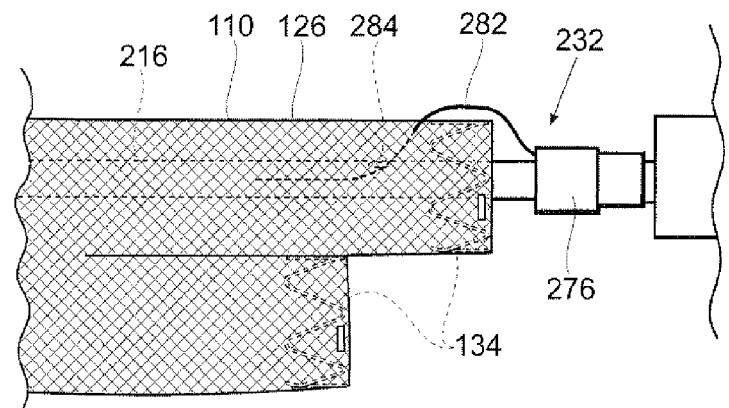
FIG. 32 is a side view of an alternative embodiment of the distal end of the main body prosthesis positioned on the deployment catheter central shaft prior to deployment of the distal retaining means.
Figure 33:
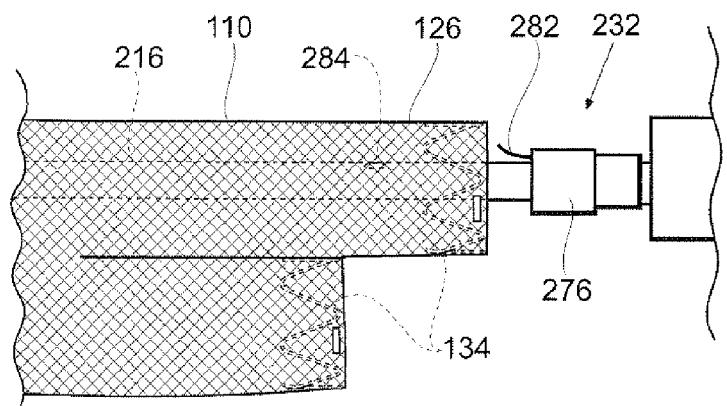
FIG. 33 is a side view of the distal end of the main body component of the multi-lumen prosthesis positioned on the deployment catheter shaft of FIG. 32, showing the alternative distal retaining means released and the distal end of the main body component expanded.

In an alternative embodiment, the distal retaining means 220 may comprise the prosthesis material 112. As can be seen in FIG. 32, the distal release wire 282 may be threaded through the prosthesis material 112 near the distal end 110 of the main body prosthesis 120, e.g., the first lumen 126. The distal release wire 282 then desirably extends into the second distal lumen 284. The proximal end of the release wire 282 is thereby kept in a desired relationship within or along the central shaft 216 to retain the wire 282. In this configuration, the distal stent(s) 134 are not radially restrained. As the outer jacket is retracted, the distal end 110 of the main body prosthesis 120 is free to radially expand. The distal release wire 282 serves to maintain the position of the distal end 110 relative to the catheter shaft 216. This feature allows for a greater flow of fluid through the lumens of the main body prosthesis while still maintaining longitudinal or axial control of the main body prosthesis 120 during the deployment process. In the illustrated embodiment, the withdrawal of the release wire 282 is accomplished by operating a control knob to move the release wire 282 distally, withdrawing the release wire 282 from the prosthesis material 112 and releasing the restrained components of the main body prosthesis 120 from the catheter shaft 216, as FIG. 33 shows.

B. The Outer Jacket

As previously described, the outer jacket 210 serves to restrain the stents 130, 134 on the main body prosthesis 120 from expanding and allows for a controlled deployment of the main body prosthesis 120 within the body (see FIG. 14A). In the illustrated arrangement, the outer jacket 210 is coupled to an actuator or knob 302 on the handle assembly 212, as will be described in greater detail below.

As FIG. 14A shows, the outer jacket 210 extends proximally over the spacer 206 and main body prosthesis 120 and terminates adjacent the distal end 242 of the catheter tip component 222. Typically, the outer jacket 210 can be made of a polymer tube or similar materials known in the art. In one embodiment, the jacket 210 may be free of structural reinforcement. In an alternative embodiment (shown in FIG. 14B), the jacket 210 may include structural reinforcement, such as but not limited to, a wire or rod 211 positioned longitudinally along a length of the jacket, and/or a wire or rod 213 positioned helically around a length of the jacket. The structural reinforcement may also be in the form of a coil(s) or braided wire, for example. The plasticity of the structural reinforcement may be altered to affect the flexibility of the jacket 210 depending on a selected application. In addition, the structural reinforcement may extend along the full length of the jacket 210, or may be positioned along only a portion or portions of the length of the jacket. The structural reinforcement may be embedded within the jacket 210, or may be coupled to the interior or exterior surface of the jacket.

In the illustrated embodiment, the outer jacket 210 is configured to maintain a consistent diameter throughout its entire length (see FIG. 11). The outer jacket may also be tapered due to a difference in outer diameters of the catheter tip component 222. The diameter of the outer jacket 210 is intended to contain the main body prosthesis 120, and optionally an extension portion 140 or portions of the main body prosthesis 120, if present. The outer diameter continues distally to the handle assembly 212. The relatively small size of the outer diameter of the outer jacket 210 also allows for better blood circulation passed the deployment catheter 200.

Returning to FIG. 14A, the spacer 206 provides support for the outer jacket 210 and, by occupying space within the outer jacket 210, reduces the amount of air entrapped within the deployment catheter 200. The proximal end of the spacer 206 desirably terminates adjacent the distal end 110 of the main body prosthesis 120. In this arrangement, the cavity 234 containing the main body prosthesis 120 extends from the distal end 242 of the catheter tip component 222 to the proximal end of the spacer 206. As FIG. 14A shows, the spacer 206 is positioned over the central shaft 216 and the distal end of the spacer 206 is connected to the handle assembly 212. Typically, the spacer 206 can have an outer diameter slightly less than the inner diameter of the outer jacket 210. The spacer 206 can comprise a single lumen or an array of multiple lumens for passage of the various components within the spacer 206.

C. Handle Assembly

The handle assembly 212 provides the operator with longitudinal or axial control and rotational control of the deployment catheter 200 within the body and provides access to the actuator(s) or control means for deploying the main body prosthesis 120.

Figure 34:
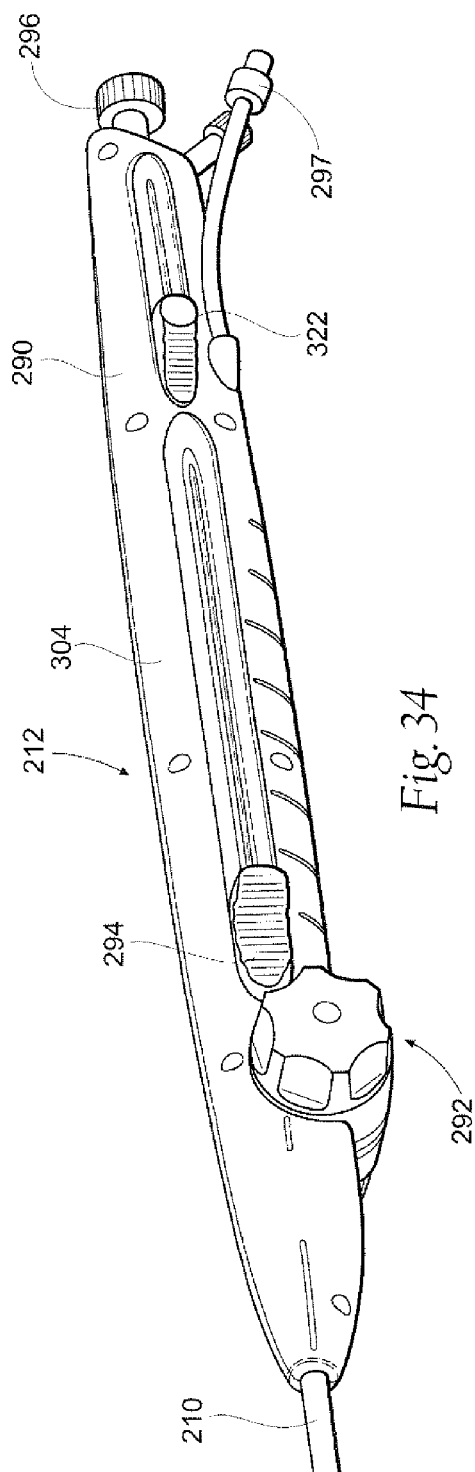
FIG. 34 is a perspective view of a first side of the deployment catheter handle assembly that embodies features of the invention.
Figure 35:
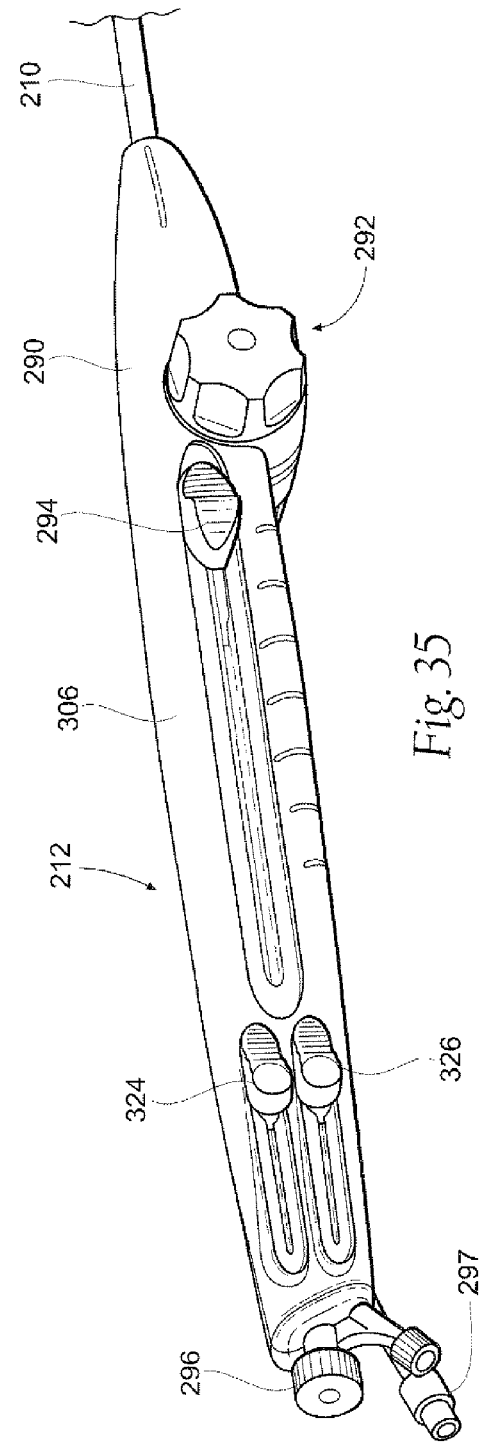
FIG. 35 is a perspective view of a second side of the deployment catheter handle assembly that embodies features of the invention.
Figure 36:
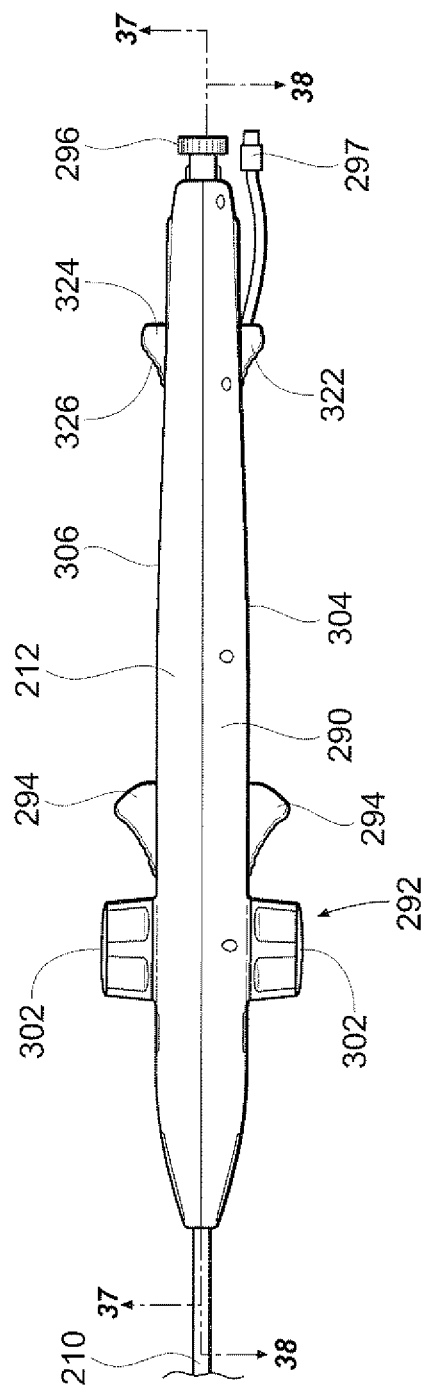
FIG. 36 is a top view of the deployment catheter handle assembly of FIG. 34.

Referring to FIGS. 34 through 36, the handle assembly 212 comprises a handle body 290, a jacket retraction means 292, which is connected to the distal end of the outer jacket 210, a sliding knob 294 which may also be connected to the distal end of the outer jacket 210, and at least one actuator or knob which is attached to the distal end of the proximal and distal releasing means. Desirably, the handle 212 comprises a separate knob for each of the first proximal releasing means 228, the second proximal releasing means 230, and the distal releasing means 232.

Figure 37:
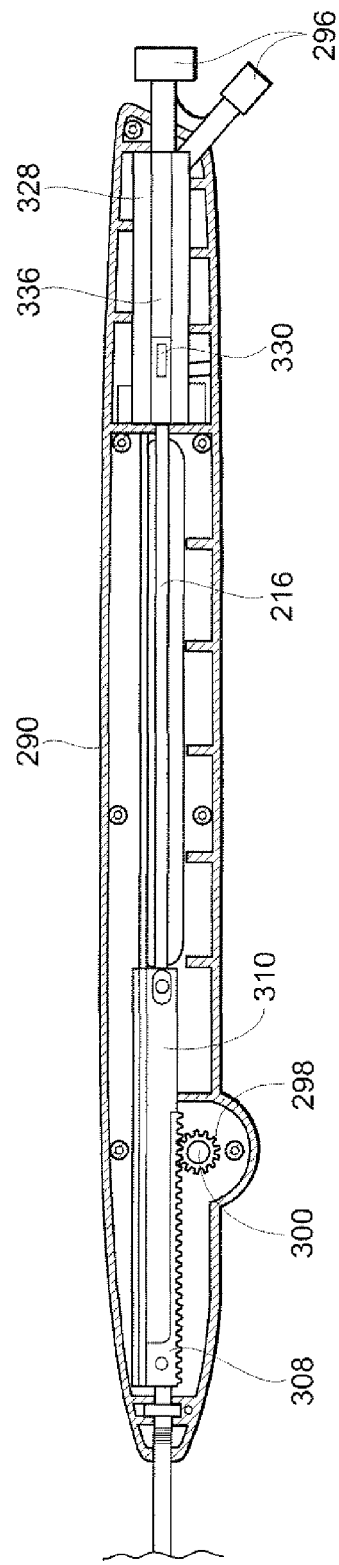
FIG. 37 is a section view of the deployment catheter handle assembly of FIG. 34 taken generally along line 37-37 of FIG. 36.
Figure 38:
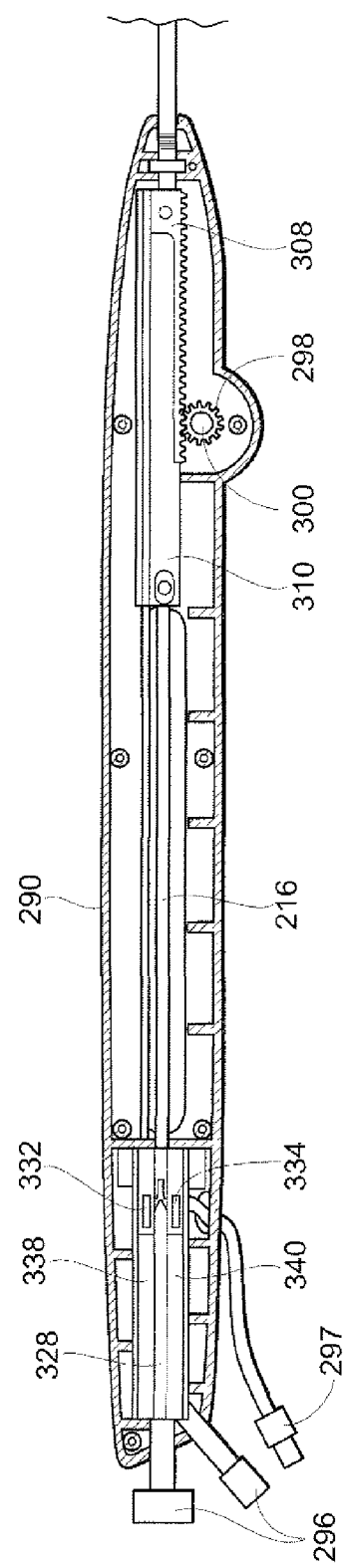
FIG. 38 is a section view of the deployment catheter handle assembly of FIG. 34 taken generally along line 38-38 of FIG. 36.

In the illustrated embodiment, the central shaft 216 is captured within the handle 212 and has a guide wire receiving luer 296 and an infusion valve 297 coupled to its distal end, which is located at the distal end of the handle assembly 212 (see FIGS. 37 and 38). This feature prevents the position of the main body prosthesis 120 from moving relative to the handle body 212 while the outer jacket 210 is retracted, and allows for irrigation or flushing of the catheter shaft 216, such as with a saline solution.

Figure 39:
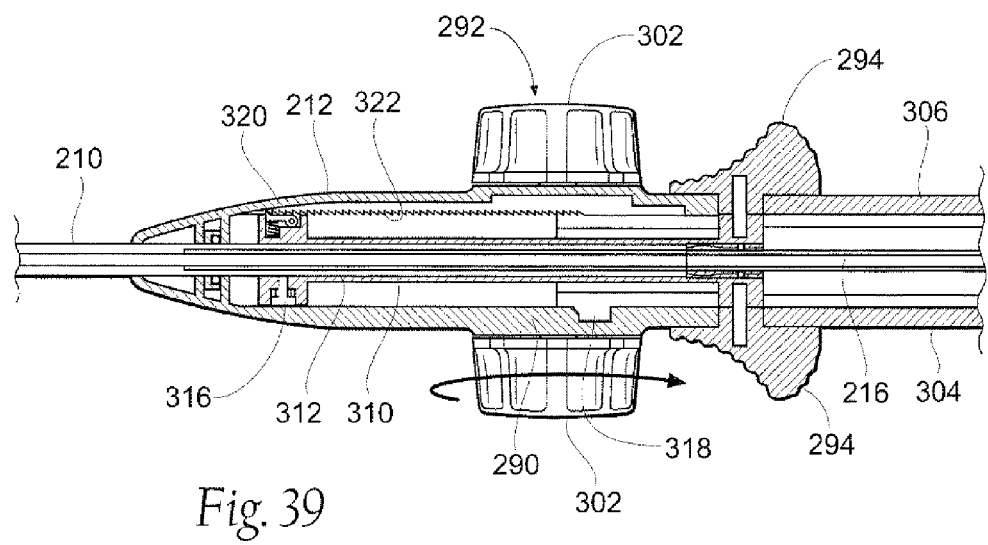
FIG. 39 is a top view of a portion of the deployment catheter handle assembly of FIG. 34 showing the jacket retraction means prior to jacket retraction.
Figure 40:
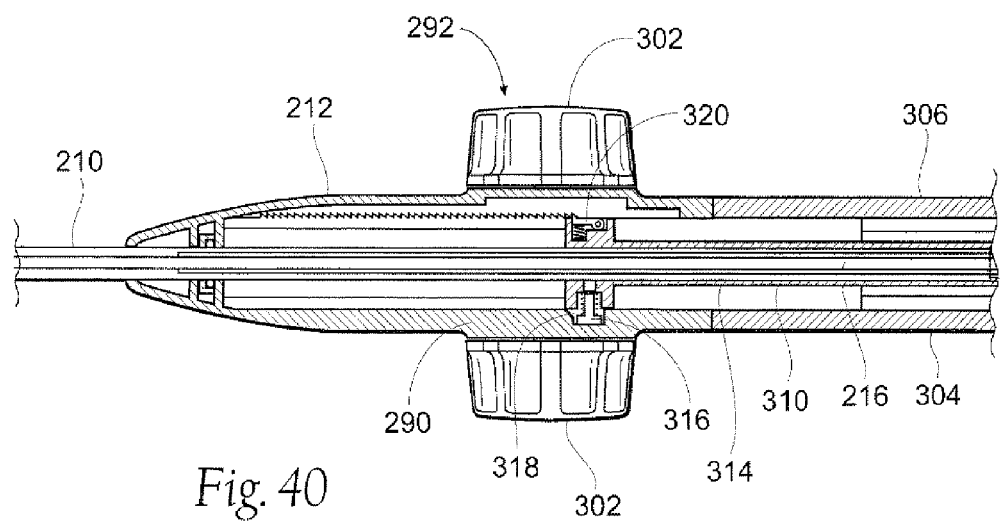
FIG. 40 is a top view of a portion of the deployment catheter handle assembly of FIG. 39 showing the jacket retraction means after the jacket has been retracted.

To withdraw the outer jacket 210 from the catheter tip 222 and expose the proximal end of the main body prosthesis 120 (see FIGS. 37 through 40), the jacket retraction means 292 is used. The jacket retraction means 292 may include a variety of different mechanisms to selectively control the retraction of the jacket 210 from the catheter tip 222. In the illustrated embodiment, the jacket retraction means 292 comprises a rack and pinion type control mechanism to provide a mechanical advantage sufficient to withdraw the jacket 210 from the catheter tip 222. A pinion 298 is carried by a gear axle 300, and is rotated by a starting knob 302 positioned on at least one end of the gear axle 300, as best seen in FIG. 41. A single starting knob may be present, or as shown in FIGS. 39 and 40, two co-acting starting knobs 302 may be available for the clinician, one positioned on a first side 304 and one positioned on a second side 306 of the handle 212. A complimentary rack 308 is carried by a jacket slide 310. The pinion 298 controls distal movement of the rack 308 along the jacket slide 310 between a first (jacket extended) position 312, shown in FIG. 39, and a second (jacket retracted) position 314, shown in FIG. 40.

The jacket slide 310 is coupled to the jacket 210 and is temporarily coupled to the gear rack 308 via a spring loaded connecting pin 316. The connecting pin 316 disengages the jacket slide 310 at a predetermined position in the handle body 290 by springing or otherwise retracting into a recess 318 in the handle body 290. When the connecting pin 316 disengages, the jacket slide 310 is free to travel in both a proximal and distal direction without re-engaging the rack 308. The rack 308 desirably remains in this retracted position 314. A ratchet pawl, such as a spring backed ratchet pawl 320 may be coupled to the rack 308 to allow the rack to travel in a distal direction, but restrict proximal travel of the rack 308. Ratchet teeth 322 may be provided in the handle body 290 to engage the ratchet pawl 320.

Figure 60:
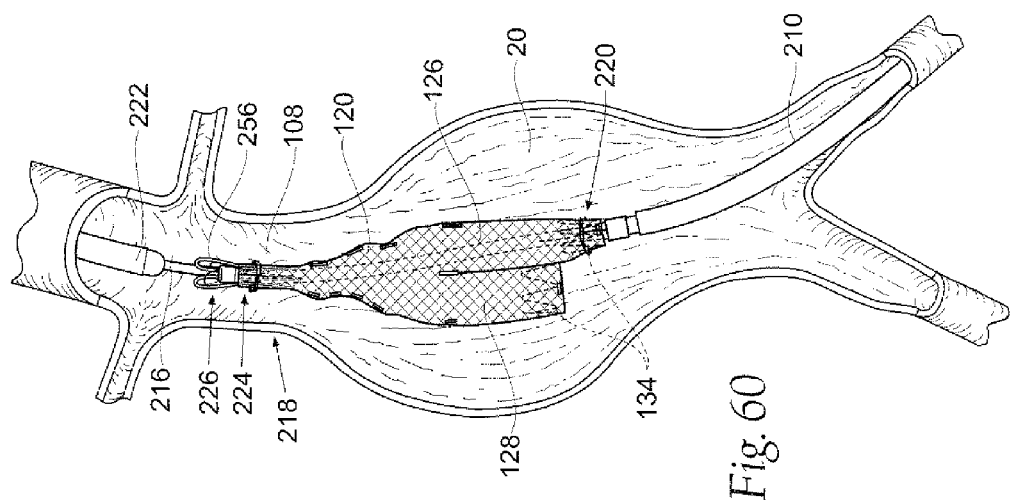
FIG. 60 is a perspective view of the deployment of the main body component of the multi-lumen prosthesis within the aneurysm of FIG. 58, with the jacket fully retracted but prior to the release of the proximal or distal retaining means.

Once the jacket slide 310 has traveled distally and the rack 308 has been disengaged, the jacket sliding knob 294 may then be used to continue the retraction of the jacket 210 from the main body prosthesis 120. The jacket slide 310 is moved distally until the outer jacket 210 is free of the main body prosthesis 120 (see FIG. 60, for example). The portion or portions of the main body prosthesis 120 that are not coupled to the proximal and distal retaining means 218, 220, are free to self-expand, as FIG. 60 shows. However, the portions of the main body prosthesis 120 that are coupled to the proximal and distal retaining means 218, 220, are still restrained from self-expansion, despite withdrawal of the outer jacket 210, as FIG. 60 also shows. The stent structure of the main body prosthesis 120 is thereby kept restrained in a close relationship against the central shaft 216 while the outer jacket 210 is retracted. The proximal and distal retaining means 218, 220 prevents the main body prosthesis 120 from moving relative to the central shaft 216 during retraction of the outer jacket 210, which potentially minimizes blood flow through the main body prosthesis 120 during the deployment process. Furthermore, as described, the main body prosthesis 120 is not "pushed out" of the catheter. The main body prosthesis 120 therefore need not have longitudinal stiffness or a stent structure with a "spine".

To employ the first proximal retaining means 224, the first proximal sliding knob 322 (see FIG. 34) is moved distally until the proximal end of the first proximal releasing means 228 is withdrawn from the first proximal retaining means 224, as previously described. In the illustrated embodiment, the first proximal release wire 250 is positioned within the loops of the suture loop 252, as seen in FIGS. 17 and 18A. As the first proximal release wire 250 is withdrawn from the suture loop 252, the suture loop 252 releases its retentive feature, yet may remain coupled to the prosthesis material 112. The proximal end 108 of the main body prosthesis 120 is thereby free to self-expand to its first stage deployment configuration, as FIG. 19 shows.

The same process is repeated for the second proximal retaining means 226 and the distal retaining means 220. To employ the second proximal retaining means 226, the second proximal sliding knob 324 (see FIG. 35) is moved distally until the proximal end of the second proximal releasing means 230 is withdrawn from the second proximal retaining means 226, as previously described. The proximal end 108 of the main body prosthesis 120 is thereby finally released from the catheter shaft 216, as FIG. 26 shows. To employ the distal retaining means 220, the distal sliding knob 326 (see FIG. 35) is moved distally until the proximal end of the distal releasing means 232 is withdrawn from the distal retaining means 220. The distal end 110 of the main body prosthesis 120 is thereby free to self-expand to its final deployment configuration, as FIG. 30 shows. Each of the se steps will be described in greater detail in section V. It is to be appreciated that the sliding buttons or knobs may all be positioned on the first side 304 of the handle, or all may be positioned on the second side 306 of the handle, or may be positioned with one or more on the first side 304 and one or more on the second side 306, as shown. It should also be appreciated that the knobs 322, 324, 326, can comprise separate components that are not part of the handle assembly 212, i.e., on the outer jacket 210.

The proximal and distal retaining means 218, 220, desirably cooperate with a release system 328 positioned within the handle housing 290 (see FIGS. 37 and 38). Each sliding knob 322, 324, 326, is coupled to a release slide 330, 332, 334, respectively, positioned within a track 336, 338, 340, respectively, in or on the release system 328 (see FIGS. 41 through 43). Each release slide is coupled to the distal end of the releasing means, such as a release wire. It is to be appreciated that the release system 328 may also include an interlock system, such as a mechanical linkage for controlling the order by which the slides may be moved. In addition, an interlock system could also include a mechanical linkage to the jacket retraction slide 310. This feature would prevent the activation of the release slides until the jacket had been retracted to a predetermined position. It is also to be appreciated that the sliding knobs may include a symbol to indicate to the clinician an appropriate order of deployment.

As described, the main body prosthesis 120 is not released immediately from proximal end to distal end as the jacket 210 is withdrawn. The proximal and distal stent or stents 130, 134, are released in a secondary operation, which follows the withdrawal of the outer jacket 210. Placement of the prosthesis extensions 140 can therefore comprise a next step in the deployment process.

2. Lumen Extension Deployment Catheter

Figure 44A:
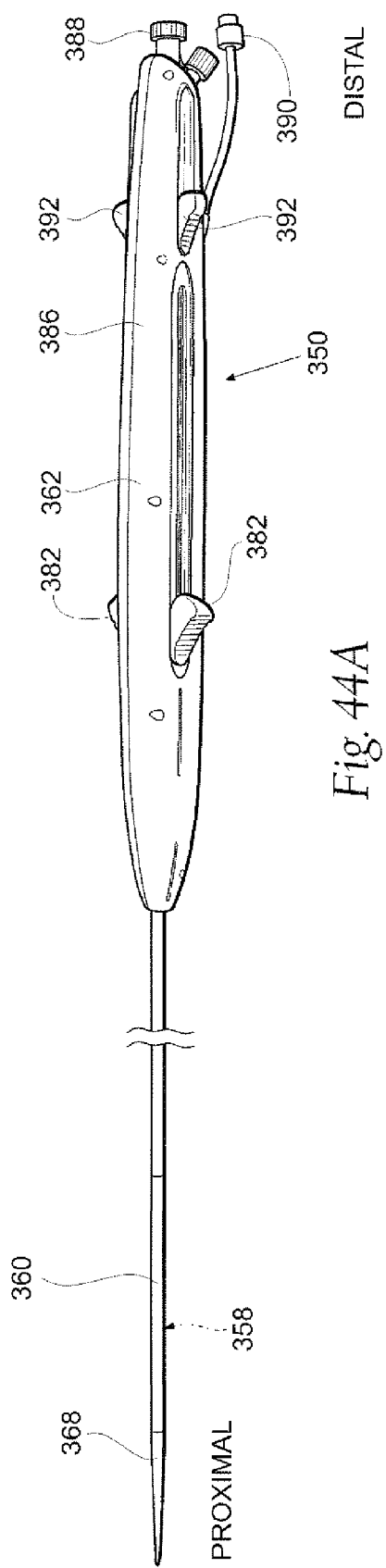
FIG. 44A is a perspective view of a lumen extension deployment catheter that embodies features of the invention.

After the main body of the prosthesis 120 has been partially or completely deployed, a lumen extension 140, or lumen extensions, are next to be implanted. An extension deployment catheter 350 is shown in FIG. 44. It is to be appreciated that the extension deployment catheter 350 may incorporate all the feature disclosed in the description of the deployment catheter 200. The extension catheter is used for delivery and deployment of the lumen extensions 140 to the targeted site.

In the illustrated embodiment, the extension catheter 350 carries the lumen extension 140 in a radially reduced configuration to the targeted site. At the targeted site, the extension catheter 350 releases the radially reduced lumen extension 140, which expands radially, and is coupled to a lumen of the main body prosthesis 120, as will be described further in section V.

Figure 44B:
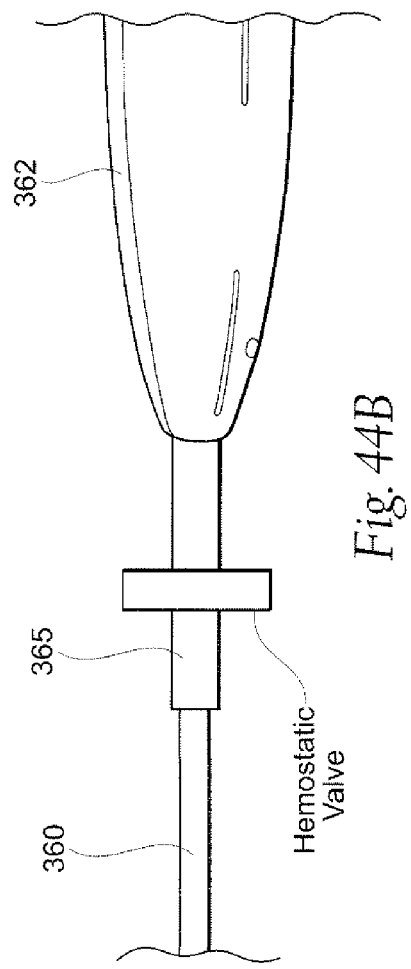
FIG. 44B is a perspective view of the lumen extension deployment catheter shown in FIG. 44A, and showing a stationary outer jacket and a hemostatic valve.
Figure 45A:
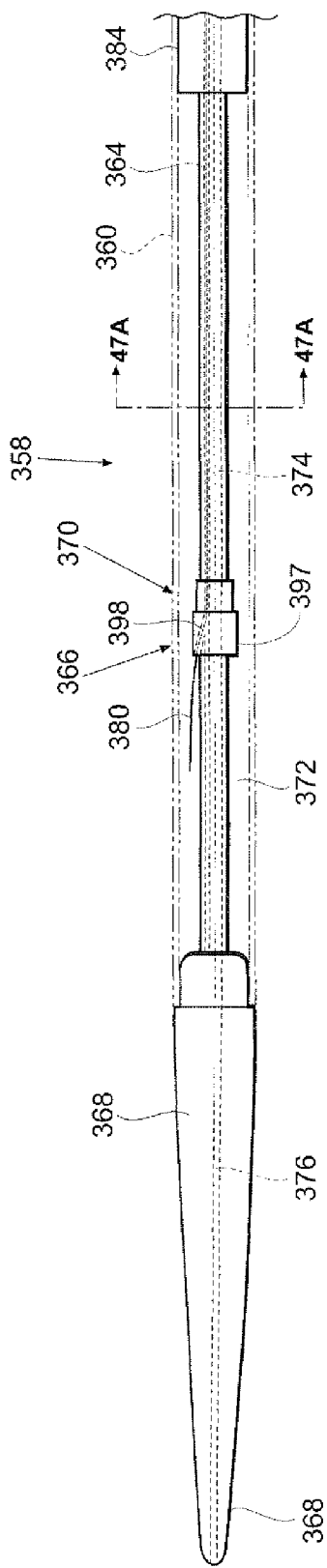
FIG. 45A is a side view of one embodiment of the proximal end of the lumen extension deployment catheter of FIG. 44.
Figure 45B:
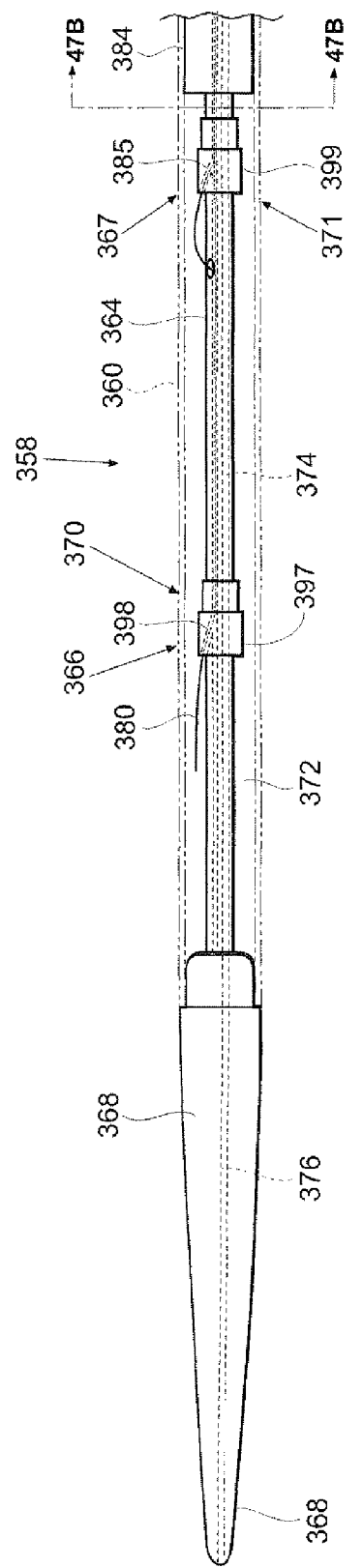
FIG. 45B is a side view of an alternative embodiment of the proximal end of the lumen extension deployment catheter of FIG. 45A, and shows an optional distal retaining and releasing means.

As shown in FIGS. 44 through 45B, the extension catheter 350 comprises an inner assembly 358, an outer jacket 360, and a handle assembly 362. These components will now be individually described in greater detail.

A. The Inner Assembly

In the illustrated embodiment (see FIG. 45A), the inner assembly 358 comprises a central shaft 364, which functions as a carrier for the lumen extension 140, proximal retaining means 366, and an extension catheter tip component 368. The proximal retaining means 366 desirably retains at least a portion of the lumen extension 140 in a radially compressed or partially radially expanded condition prior to deployment and prior to coupling to the main body prosthesis 120. The proximal retaining means 366 also desirably includes a co-acting releasing means or mechanism 370 for maintaining the proximal retaining means 366 in a desired relationship with the lumen extension 140 prior to activation.

In an alternative embodiment (see FIG. 45B), the inner assembly may also include distal retaining means 367. The distal retaining means 367 desirably retains at least the distal portion of the lumen extension 140 in a radially compressed or partially radially expanded condition prior to deployment and prior to coupling to the main body prosthesis 120. The distal retaining means 367 also desirably includes a co-acting releasing means or mechanism 371 for maintaining the distal retaining means 367 in a desired relationship with the lumen extension 140 prior to activation.

i. The Central Shaft

In the embodiments shown in FIGS. 45A and 45B, the central shaft 364 and the proximal and distal retaining means 366, 367 are located within the confines of the outer jacket 360. In this respect, the outer jacket 360 functions as an enclosure or jacket for the lumen extension 140 on the shaft 364 (see FIGS. 46A and B). In this arrangement, the catheter tip component 368 is attached to the proximal end of the central shaft 364, and the proximal end of the outer jacket 360 terminates adjacent the catheter tip component 368. Thus, the extension catheter tip component 368 extends outward beyond the outer jacket 360. The central shaft 364, the proximal releasing means 366, the distal releasing means 367 (shown in FIG. 45B), and the outer jacket 360 are coupled to the handle assembly 362 at the proximal end of the catheter handle assembly 362 (see FIG. 44). As can be seen in FIGS. 46A and 46B, the lumen extension 140 is contained in a cavity 372 defined between the central shaft 364 and the outer jacket 360 in the proximal section of the extension catheter 350.

The central shaft 364 extends from the handle assembly 362 to the catheter tip component 368. The central shaft 364 may be made, e.g., from stain less steel or other suitable medical materials including other metals or polymers. The central shaft 364 comprises at least one lumen, and may comprise more than one lumen.

Figure 47A:
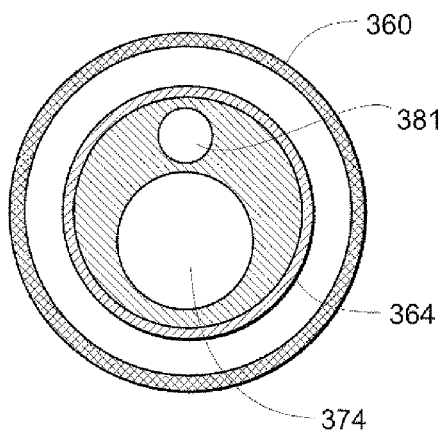
FIG. 47A is a section view of the lumen extension deployment catheter shaft of FIG. 45A taken generally along line 47A-47A of FIG. 45A.
Figure 47B:
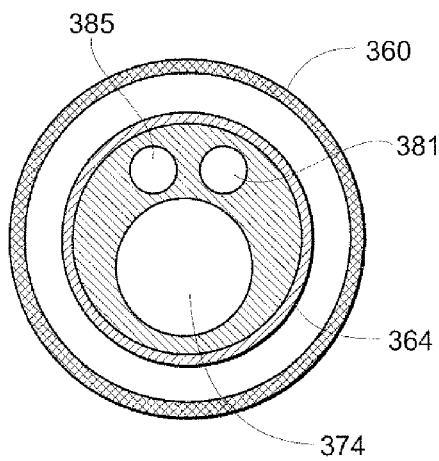
FIG. 47B is a section view of an alternative embodiment of the lumen extension deployment catheter shaft of FIG. 45B taken generally along line 47B-47B of FIG. 45B.

One lumen may be described as the central lumen 374 (see FIGS. 47A and 47B), with an inner diameter between 0.010 and 0.120 inches, desirably between 0.020 and 0.060 inches and most desirably between 0.030 and 0.050 inches. As described, the central lumen 374 allows for the insertion of a guide wire, i.e., the first guide wire 30 or the second guide wire 40, up to 0.038" diameter, for example. The catheter tip component 368, having the same features as described for the catheter tip 222 of the deployment catheter 200, also desirably has at least one lumen 376 (see FIG. 45A) configured to align with at least one lumen within the central shaft 364. This lumen 376 allows for the insertion of the guide wire through the central shaft 364 and through the extension catheter tip component 368. Typically this lumen 376 will have an inner diameter between 0.010 and 0.120 inches, desirably between 0.020 and 0.060 inches and most desirably between 0.030 and 0.050 inches.

ii. Proximal Retaining Means

Figure 48A:
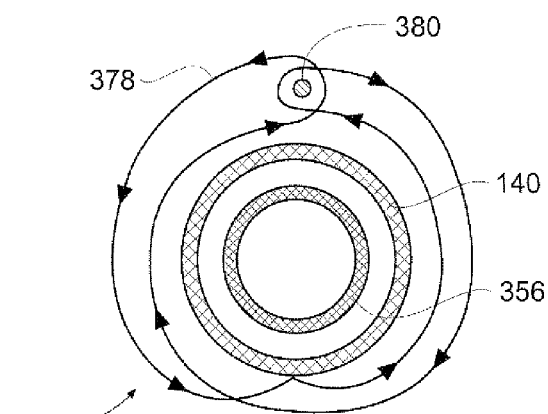
FIG. 48A is a side view of one embodiment of a suture loop path around the proximal end of the lumen extension.
Figure 48B:
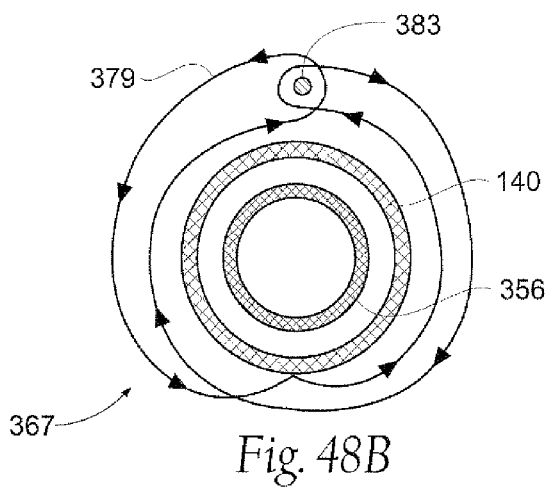
FIG. 48B is a side view of one embodiment of a suture loop path around the distal end of the lumen extension.
Figure 48C:
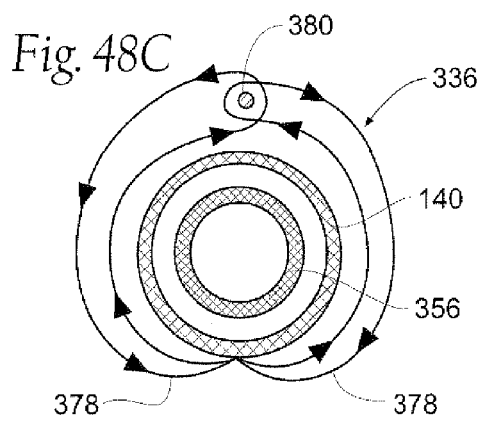
FIG. 48C is a side view of an alternative embodiment of a suture loop path around the proximal or distal end of the lumen extension shown in FIGS. 48A and 48B, and shows multiple suture loops.

The proximal retaining means 366 and the proximal releasing means 370 may function in the same or similar fashion as the retaining means 224, 226, and the releasing means 228, 230 embodied in the deployment catheter 200, as previously shown and described. As can be seen in FIGS. 46A and 48A, in the illustrated embodiment, the proximal retaining means 366 comprises at least one suture, or sutures, 378 and/or equivalent structures, which are coupled to the lumen extension prosthetic material 112, or to one or more stents 150 on the lumen extension 140. The suture 378 is, in turn, looped around the proximal releasing means 370, e.g., a release wire 380, when the release wire 380 is in its proximal-most position, as FIGS. 46A and 48A show. Distal retraction of the wire 380 positioned within a releasing wire lumen 381 (see FIGS. 45A and 47A) withdraws the wire 380 from the suture loop 378, and allows the proximal end 142 of the lumen extension 140 to radially expand, as can be seen in FIGS. 70 and 71. In an alternative embodiment, the suture 378 may comprise more than one suture, i.e., two or more suture loops. FIG. 48C shows the path of two suture loops 378 looped around the release wire 380.

As described for the main body prosthesis 120, belt loops or the like may be provided on the lumen extensions 140 as well to guide and support the suture loop(s) along the path of the suture loop. The belt loops can be spaced at desired circumferential intervals, such as every ninety degrees, for example.

As can be seen in FIG. 45A, the proximal releasing means 370 comprises a proximal release hub 397 positioned over the central shaft 364, and the release wire 380. The proximal release hub 397 may include a small hole or lumen 398 in the proximal end of the hub 397 that is in fluid communication with the proximal releasing wire lumen 381 within the central shaft 364. Each lumen 381, 398 desirably include a diameter sufficiently large to accommodate the release wire 380 extending from the handle assembly 362 to beyond the release hub 397. It is to be appreciated that the release wire 380 may extend external the shaft 364 as well.

iii. Distal Retaining Means

In an alternative embodiment, the distal retaining means 367 and the distal releasing means 371 may function in the same or similar fashion as the retaining means 220, and the releasing means 232 embodied in the deployment catheter 200, as previously shown and described. As can be seen in FIGS. 46B and 48B, the distal retaining means 367 comprises at least one suture, or sutures, 379 and/or equivalent structures, which are coupled to the lumen extension prosthetic material 112, or to one or more stents 150 on the lumen extension 140. The suture 379 is, in turn, looped a round the distal releasing means 371, e.g., a release wire 383, when the release wire 383 is in its proximal-most position, as FIGS. 46B and 48B show Distal retraction of the wire 383 positioned within a releasing wire lumen 385 (see FIGS. 45B 47B) with draws the wire 383 from the suture loop 379, and allows the distal end 144 of the lumen extension 140 to radially expand. As described for the proximal retaining means 366, the suture 379 may also comprise more than one suture, i.e., two or more suture loops. FIG. 48C shows the path of two suture loops 378 looped around the release wire 380. This path may also be used for suture loops 379 looped around the release wire 383.

As can be seen in FIG. 45B, the distal releasing means 371 comprises a distal release hub 399 positioned over the central shaft 364, and the release wire 383. The distal release hub 399 may include a small hole or lumen 395 in the proximal end of the hub 399 that is in fluid communication with the distal releasing wire lumen 385 within the central shaft 364. Each lumen 385, 395 desirably include a diameter sufficiently large to accommodate the release wire 383 extending from the handle assembly 362 to beyond the release hub 399. It is to be appreciated that the release wire 383 may extend external the shaft 364 as well.

B. The Outer Jacket

The outer jacket 360 may function in the same or similar fashion as described for the outer jacket 210 embodied in the deployment catheter 200. The outer jacket 360 also serves to restrain the stents 146 and 150 on the lumen extension 140 from expanding and allows for a controlled deployment of the lumen extension 140 within a lumen of the main body prosthesis 120. In the illustrated arrangement, the outer jacket 360 is coupled to an actuator or knob 382 on the handle assembly 362, as will be described in greater detail below.

As FIGS. 46A and 46B show, the outer jacket 360 extends proximally over a spacer 384 and lumen extension 140 and terminates adjacent the distal end of the catheter tip component 368. Typically, the outer jacket 360 can be made of a polymer tube or similar materials known in the art. In one embodiment, the jacket 360 may be free of structural reinforcement. In an alternative embodiment (shown in FIG. 46C), the jacket 360 may include structural reinforcement, such as but not limited to, a wire or rod 361 positioned longitudinally along a length of the jacket, and/or a wire or rod 363 positioned helically around a length of the jacket. The structural reinforcement may also be in the form of a coil(s) or braided wire, for example. The plasticity of the structural reinforcement may be altered to affect the flexibility of the jacket 360 depending on a selected application. In addition, the structural reinforcement may extend along the full length of the jacket 360, or may be positioned along only a port ion or portions of the length of the jacket. The structural reinforcement may be embedded within the jacket 360, or may be coupled to the interior or exterior surface of the jacket.

If desired, and as shown in FIG. 44B, a stationary outer jacket 365 may be provided that extends from the proximal end of the handle assembly 362. The jacket 360 slides within the stationary jacket 365. The stationary jacket 365 provides a seal interface with a hemostatic valve at the access site. The stationary jacket 365 can be made of a suitable medical grade plastic, such as Fluroinated Ethylene Propylene (FEP) as non-limiting example. The stationary outer jacket 365 provides column strength and lubricity to reduce friction during sliding actuation of the jacket 360. The stationary outer jacket 365 may also be provided for the prosthesis deployment catheter 200 for the same purposes.

C. Handle Assembly

The handle assembly 362 may function in the same or similar fashion as described for the handle assembly 212 embodied in the deployment catheter 200. The handle assembly 362 provides the operator with longitudinal or axial control and rotational control of the extension deployment catheter 350 within the body and provides access to the actuator(s) or control means for deploying the lumen extension 140.

Figure 49A:
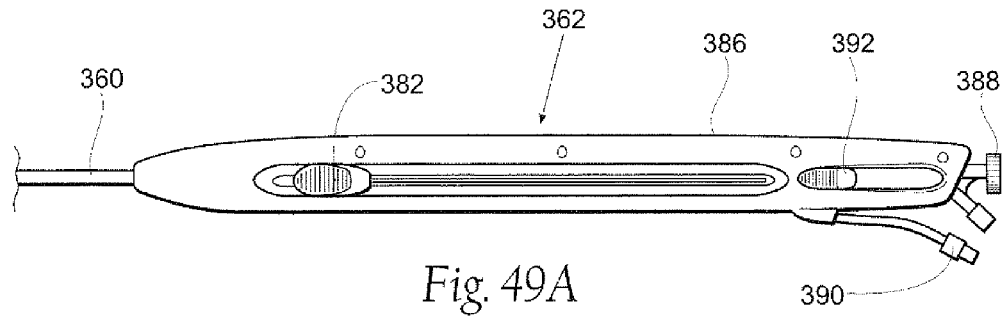
FIG. 49A is side view of the lumen extension deployment catheter handle assembly of FIG. 44.
Figure 49B:
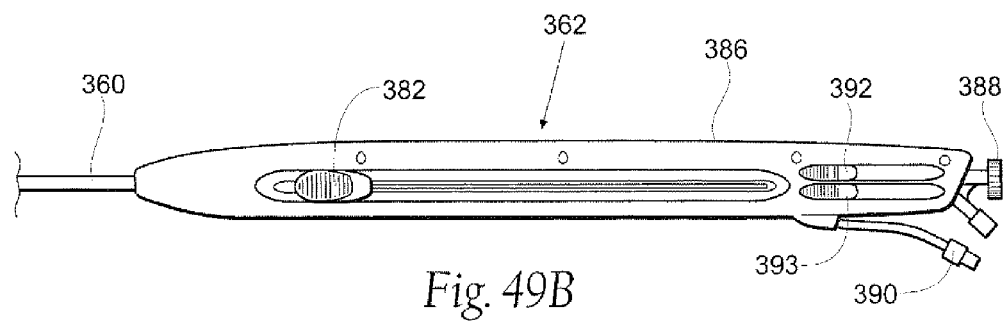
FIG. 49B is a side view of an alternative embodiment of the lumen extension deployment catheter handle assembly of FIG. 44, and showing and additional slide knob for an optional distal releasing means.
Figure 50:
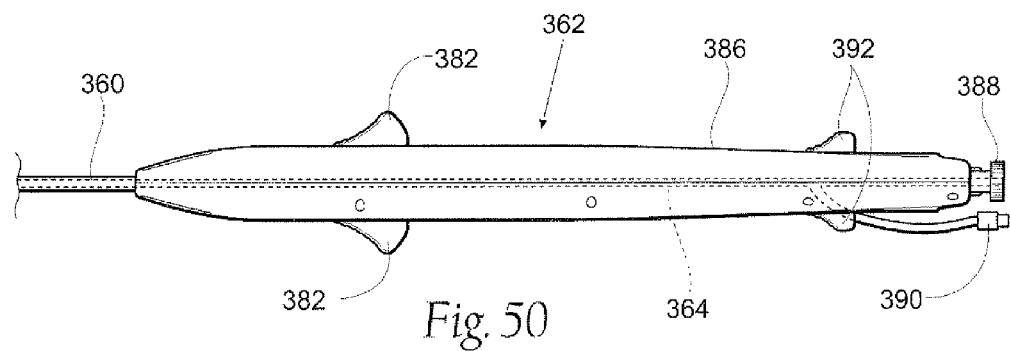
FIG. 50 is top view of the lumen extension deployment catheter handle assembly of FIG. 44.

Referring to FIGS. 49 and 50, the handle assembly 362 comprises a handle body 386, a jacket retraction means 382, which is connected to the distal end of the outer jacket 360, and at least one knob or button 392 which is attached to the distal end of the proximal releasing means 370. It is to be appreciated that the handle assembly 362 may also include at least one knob or button 393 (see FIG. 49B) attached to an optional distal releasing means 371 and the knob or button may function in the same or similar fashion as described below for the proximal releasing means 370.

Figure 51:
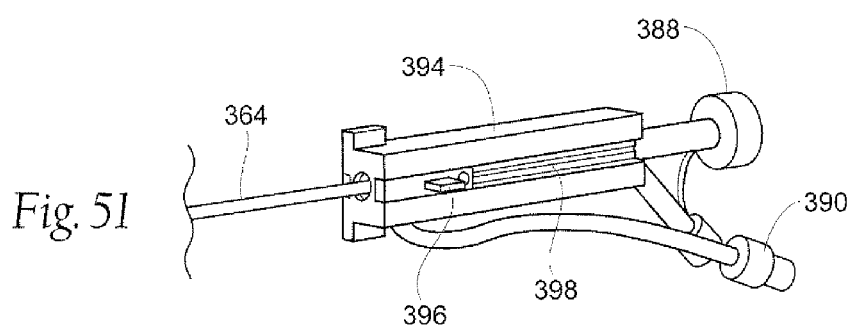
FIG. 51 is a perspective view of one embodiment of the release system positioned within the handle assembly of the lumen extension deployment catheter.

In the illustrated embodiment, the central shaft 364 is captured within the handle 362 and has a guide wire receiving luer 388 and an infusion valve 390 coupled to its distal end, which is located at the distal end of the handle assembly 362 (see FIGS. 50 and 51). This feature prevents the position of the lumen extension 140 from moving relative to the handle body 362 while the outer jacket 360 is retracted, and allows for irrigation or flushing of the catheter shaft 364, such as with a saline solution.

To withdraw the outer jacket 360 from the catheter tip 368 and expose the lumen extension 140, jacket retraction means, such as the jacket retraction knob 382 may be used. The jacket retraction means 382 may include a variety of different mechanisms to selectively control the retraction of the jacket 360 from the catheter tip 368. In the illustrated embodiment, the jacket retraction means comprises two co-acting retraction knobs 382 which are available for the clinician, one positioned on each side of the handle 362.

The jacket retraction knob 382 is used to retract the jacket 360 from the lumen extension 140. The jacket retraction knob 382 is moved distally until the outer jacket 360 is free of the lumen extension 140 (see FIG. 70). The portion or portions of the lumen extension 140 that are not coupled to the proximal retaining means 366 are free to self-expand, as FIG. 70 shows. However, the portions of the lumen extension 140 that are coupled to the proximal retaining means 366 are still restrained from self-expansion, despite withdrawal of the outer jacket 360. The stent structure of the lumen extension 140 is thereby kept restrained in a close relationship against the central shaft 364 while the outer jacket 360 is retracted. The proximal retaining means 366 prevents the lumen extension 140 from moving relative to the central shaft 364 during retraction of the outer jacket 360, which potentially minimizes blood flow through the lumen extension 140 during the deployment process. Furthermore, as described, the lumen extension 140 is not "pushed out" of the extension catheter 350. The lumen extension 140 therefore need not have longitudinal stiffness or a stent structure with a "spine".

To employ the proximal retaining means 366, the proximal release sliding knob 392 (see FIGS. 49A and 50) is moved distally until the proximal end of the proximal releasing means 370 is withdrawn from the proximal retaining means 366, as previously described. In the illustrated embodiment, the proximal release wire 380 is positioned within the loops of the suture loop 378, as seen in FIGS. 46A and 48A. As the proximal release wire 380 is withdrawn from the suture loop 378, the suture loop 378 releases its retentive feature, yet may remain coupled to the prosthesis material 112. The proximal end 142 of the lumen extension 140 is thereby free to self-expand to its deployment configuration and couple itself within the lumen of the main body prosthesis 120, as FIGS. 70 and 71 show. The natural flow of fluid through the new extension 140 provides sufficient force to cause the restraint mechanism of the lumen extension 140 to engage the co-acting restraint mechanism of the main body prosthesis 120. The lumen extension stent and/or the outwardly extending apices 147 of the lumen extension stent 150 engage the mating outwardly extending apices 136 of the main body prosthesis stent 134 (see FIG. 10B). Each of these steps will be described in greater detail in section V. It is to be appreciated that the sliding buttons or knobs may all be positioned on one side of the handle, or all may be positioned on the opposite side of the handle, or may be positioned on both sides, as shown. It should also be appreciated that the knobs 382 and 392 can comprise separate components that are not part of the handle assembly 362, i.e., on the outer jacket 360.

The proximal retaining means 366 desirably cooperate with a release system 394 positioned within the handle housing 386. Proximal release sliding knob 392 is coupled to a release slide 396 positioned within a track 398 in or on the release system 394 (see FIG. 51). The release slide 396 is coupled to the distal end of the releasing means 370, such as the release wire 380. It is to be appreciated that the release system 394 may also include an interlock system, such as a mechanical linkage for controlling the order by which the slides may be moved. In addition, an interlock system could also include a mechanical linkage to the jacket retraction slide 382. This feature would prevent the activation of the release slides until the jacket had been retracted to a predetermined position. It is also to be appreciated that the sliding knobs may include a symbol to indicate to the clinician an appropriate order of deployment.

As described, the lumen extension 140 is not released immediately from proximal end to distal end as the jacket 360 is withdrawn. The lumen extension stent or stents 146 and 150 may be released in a secondary operation, which follows the withdrawal of the outer jacket 360. Placement of the prosthesis extensions 140 can therefore comprise a final step in the deployment process.

3. Fastener Device and Fastener

As previously described, one or more fasteners 402 (see FIG. 52) may be introduced by a fastener device 400 to anchor the prosthesis 100 in place. Typically the fasteners 402 will be introduced at the proximal end of the main body prosthesis 120; however, it should be appreciated that the fasteners can be introduced in any part of the prosthesis 100, including the lumen extensions 140, to anchor it in place. In addition, the fasteners 402 may also serve to provide apposition of the prosthesis material 112 to the hollow body organ or vessel wall. Fasteners may also be used to seal and/or repair leaks or seepage of fluid (e.g., around the proximal stents and/or distal stents of the prosthesis 100). One or more fasteners 402 may be introduced into the prosthesis 100 at different times or at the same time during the procedure.

As can be seen in FIGS. 53 and 54, the fastener tool 400 desirably comprises a handle assembly 404 including a control assembly 406 and an indication assembly 408. A fastener delivery shaft 409, having a fastener driver 411 at its proximal end 410, is coupled to the proximal end of the handle assembly 404 for delivery of the fastener 402. Coupled to the distal end of the handle assembly may be an irrigation port or infusion valve 422.

The handle assembly 404 provides the fastening control feature for the clinician. Positioned within the handle assembly 404 is the control assembly 406. The control assembly provides motion control, such as a forward and reverse drive feature, for turning or otherwise moving the fastener 402 to or from a fastening position. The control assembly desirably includes a forward control button 412 and a reverse control button 414. The forward and reverse control buttons 412, 414 provide the clinician an ergonomic and single finger control of the fastener device 400.

The handle assembly desirably includes an indication assembly 408 to provide control information to the clinician. The indication assembly may include indication lights, i.e., LEDs, and/or the ability to produce audible signals (tones) to provide visual and/or audible indication of forward or reverse movement of the fastener 402, for example, by way of a variety of tones and/or a forward light 416 and a reverse light 418. Additionally, the indication assembly may include status tones and/or a status light 420 to provide a variety of information back to the clinician. The tones may use a variety of pitches or pulses, for example, and the status light 420 may use a variety a flash signals and illumination times, for example, to provide these different indications for the clinician, such as error indication, position indication, and timing indication, for example.

Further details of the fastener device 400 and fastener 402 can be found in U.S. patent application Ser. No. 10/307,226, filed Nov. 29, 2002, and entitled "Intraluminal Prosthesis Attachment Systems and Methods," and in U.S. patent application Ser. No. 10/786,465, filed Feb. 29, 2004 and entitled "Systems and Methods for Attaching a Prosthesis Within a Body Lumen or Hollow Organ," which are both incorporated herein by reference.

In this embodiment, the proximal coil 422 of the fastener 402 is formed to produce a diagonal member 424, which crosses the diameter of the helical fastener. The distal end of the fastener 402 comprises a sharpened tip 426, such as a conical tip or a chiseled tip, for example, to aid in the ease of tissue penetration. Similar helical fasteners are described in U.S. Pat. Nos. 5,964,772; 5,824,008; 5,582,616; and 6,296,656, the full disclosures of which are incorporated herein by reference.

In an alternative embodiment, the fastener device 400 and a fastener 430 may comprise features allowing the fastener 430 to be releasably secured to the fastener driver 432. As can be seen in FIGS. 79A and 79B, the proximal coil 434 of the helical fastener 430 desirably includes a diagonal member 436, which crosses the diameter of the fastener 430. The diagonal member 436 may bisect the diameter of the fastener 430, or may be off set, forming a "D" shaped proximal coil 434, as shown. The diagonal member 436 desirably comes completely across the diameter to prevent the fastener 430 from being an open coil and to control the depth of penetration into the tissue. In addition, the diagonal member 436 can be attached to a previous coil, as shown, to strengthen the entire structure and provide a retentive shape for a fastener driver 432. This attachment could be achieved via welding, adhesive or any other suitable means.

Located at the proximal end of the fastener delivery shaft 410 is the fastener driver 432. In the illustrated embodiment (see FIGS. 80 and 81), the fastener driver 432 includes a fastener carrier 438 positioned within a threaded fastener housing 439. The threaded fastener housing 439 may include tabs 437 or other coupling means so as to snap fit or couple to the fastener carrier 438 for convenient replacement. The coupling between the driver 432 and carrier 438 can take different forms—e.g., magnets, graspers, or other suitable mechanical connection. In the embodiment illustrated in FIGS. 80 and 81, the driver 432 and carrier 438 are integrally connected as a single unit.

The carrier 438 is sized and configured to engage a selected fastener 430. The diagonal member 436 serves to define a shape, such as a "D" shape, to engage the carrier 438, which rotates the fastener 430 positioned over the carrier 438 to achieve fastening the prosthesis to tissue. The diagonal member 436 also serves as a stop to prevent the helical fastener 430 from penetrating too far into the tissue.

Figure 82A:
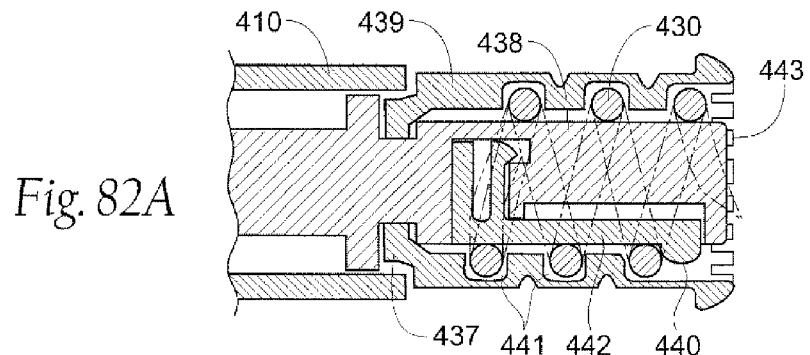
FIG. 82A is an enlarged side view of the fastener driver of FIG. 80, and showing a fastener positioned on the fastener carrier and within a threaded fastener housing, and also showing the fastener latch feature.
Figure 82B:
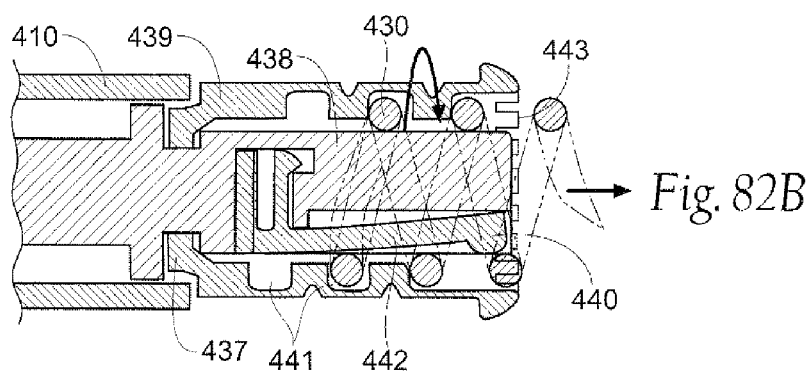
FIG. 82B is an enlarged side view of the fastener driver of FIG. 80, and showing a fastener on the carrier and rotating off the carrier and showing the pivoting of the fastener latch.

As can be seen in FIGS. 80 and 81, a fastener 430 is positioned within the fastener housing 439 and over the carrier 438. The carrier 438 includes a release latch 440. The release latch 440 may be spring loaded, magnetic, or lever action, for example. The latch 440 prevents the premature release of the fastener 430. The release latch 440 desirably requires a force to overcome the securing force of the latch. For example, the release latch 440 may be overcome by a pulling force, e.g., the fastener 430 is being fastened through the prosthesis and within tissue and the pulling force of the fastener turning or screwing into tissue may overcome the securing force of the release latch. Alternatively, the release latch 440 may be overcome by a magnetic force activated by the clinician by pressing a release button 444 on the handle assembly 404 (shown in FIG. 86). In one embodiment shown in FIGS. 82A and 82B, the release latch 440 includes a lever arm 442 to provide the latching force. As the carrier 438 is rotated to deploy the fastener 430, the force of the fastener 430 rotating into the tissue may be adequate to overcome the force of the release latch 440. As seen in FIG. 82A, the fastener 430 remains fastened to the carrier 438 by way of the fastener release latch 440. As seen in FIG. 82B, further rotation of the fastener 430 into tissue will cause each coil of the fastener to overcome the force of the release latch 440 and allow the fastener 430 to exit off of the carrier 438.

Figure 82C:
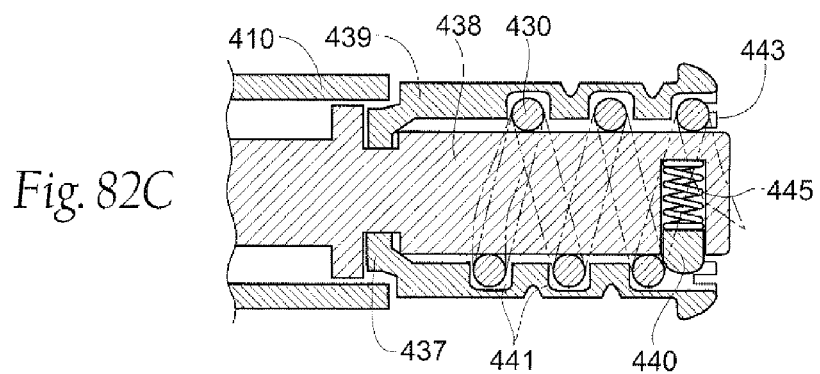
FIG. 82C is an enlarged side view of the fastener driver of FIG. 80, and showing a fastener positioned on the fastener carrier and within a threaded fastener housing, and also showing an alternative fastener latch feature.

In an alternative embodiment, the release latch 440 may include a release spring 445, as seen in FIG. 82C. The release spring 445 is sized and configured to provide a sufficient force to maintain the fastener 430 on the carrier 438, and yet allow the fastener 430 to overcome the force of the release spring 445 and release latch 440 as the fastener is being screwed into tissue.

The fastener housing 439 desirably includes a predetermined amount of internal threads 441 (e.g., two or three threads). In this configuration, the threaded portion of the housing 439 may not be continuous through out the length of the housing. The threads 441 engage the fastener 430 when the fastener is being loaded onto the fastener driver 432 (as described below) and also partially drive the helical fastener 430 out of the fastener driver 432 and into tissue. Desirably, the threaded portion of the threaded housing terminates a predetermined distance from the housing tip 443. This unthreaded portion of the threaded housing 439 provides an area in which the fastener 430 can be rotated but not be driven out of the fastener driver 432. This unthreaded feature of the housing 439 allows the fastener 430 to pull itself out of the fastener driver 432 when rotated by the driver only as long as the fastener 430 has been previously engaged with the prosthesis 120 and tissue. This feature ensures a more uniform depth of penetration for the fastener 430.

Figure 83:
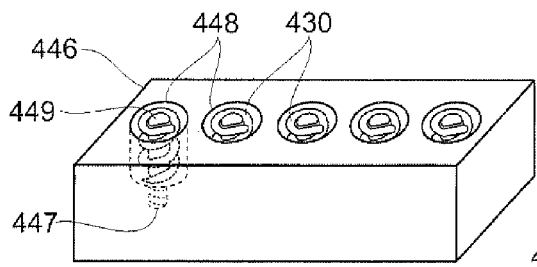
FIG. 83 is a perspective view of one embodiment of a fastener cassette with fasteners releasably positioned with a fastener receptacle.
Figure 84:
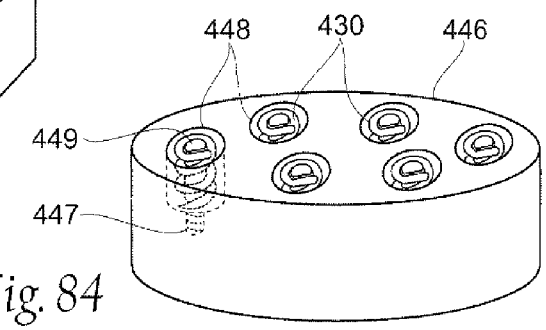
FIG. 84 is a perspective view of an alternative embodiment of a fastener cassette of FIG. 82.

A helical fastener, such as 402 and 430, for example, may be positioned in a fastener cassette 446, as seen in FIGS. 83 and 84. The fastener cassette 446 may take on any convenient shape, such as a rectangle or circle, as shown, and may include any convenient number of fastener receptacles 448, such as six, although any number may be used. The cassette 446 may be used to store and retain fasteners during shipment, and also to provide a convenient means to present the fastener 430, for example, to the fastener device 400 during a medical procedure.

As seen in FIGS. 83 and 84, the fastener receptacle 448 is sized and configured to allow the proximal end 410 and the fastener driver 432 of the fastener device 400 access to the seated fastener 430. The fastener 430 may be positioned on a receptacle post 449, to hold the fastener 430 within the receptacle 448. Or alternately, the fastener 430 may be held within the receptacle 448 through interference between the fastener 430 and the receptacle 448, or by penetrating the fastener tip 426 into a material at the base of the receptacle 448. The receptacle post 449 may include a receptacle post spring 447, allowing the receptacle post 449 to retreat into the receptacle 448 as the fastener driver 432 is inserted into the receptacle 448 to position the fastener 430 on to the carrier 438.

Figure 85:
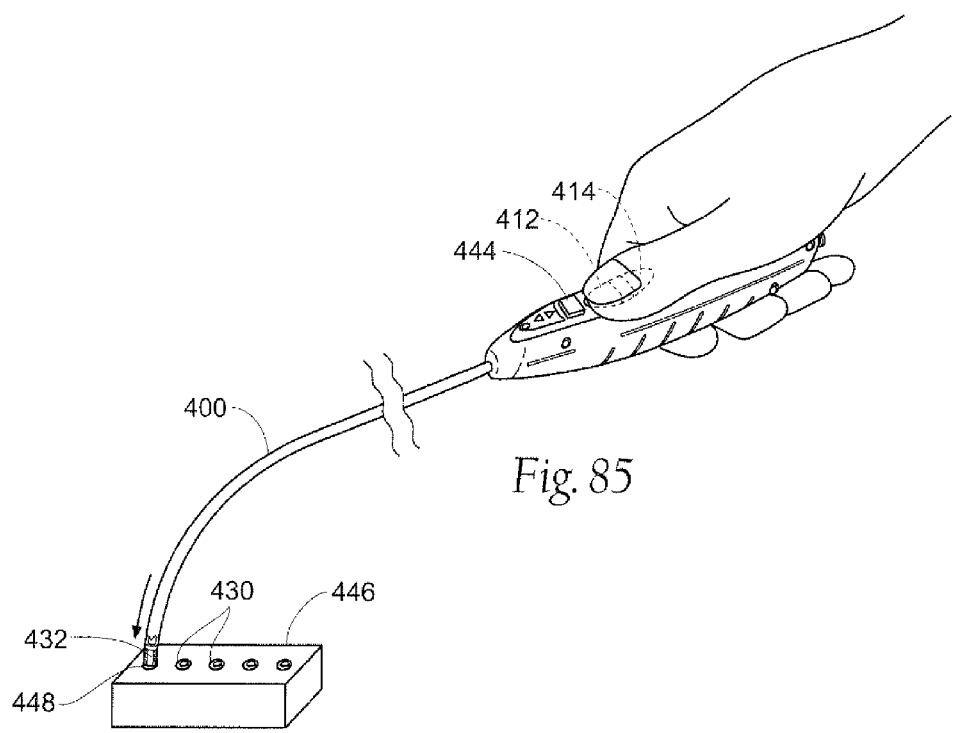
FIG. 85 is a perspective view showing the fastener tool positioned on a fastener cassette for removal of a fastener from the cassette and positioning the fastener within the fastener driver.
Figure 86:
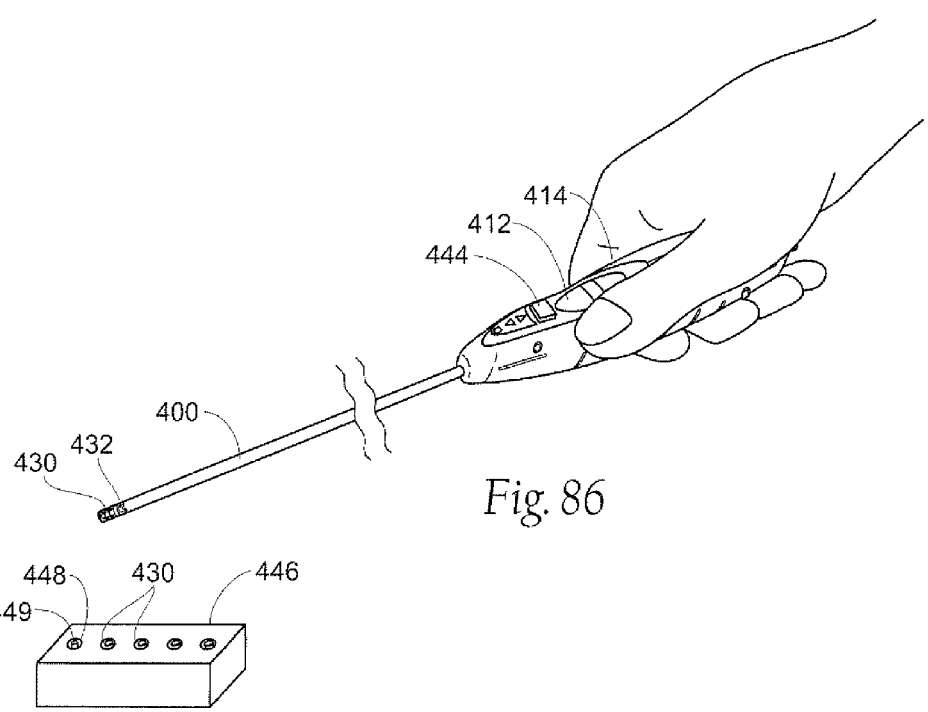
FIG. 86 is a perspective view showing the fastener tool with a fastener positioned in the fastener driver and ready for deployment.

FIGS. 85 and 86 show an embodiment of a fastener 430 being positioned within the fastener driver 432. As can be seen the fastener driver 432 is positioned on top of the receptacle 448 and gently inserted into the receptacle. The force of the insertion allows the fastener 430 to overcome the force of the release latch 440 on the carrier 438 and to be positioned over the carrier 438. The fastener driver is then reversed, using the control assembly 406 provided on the fastener driver handle 404. The internal threads 441 of the threaded housing 439 draw the fastener 430 into the fastener driver 432 and into position for deployment. FIG. 86 shows the fastener 430 removed from the cassette 446 and positioned on the fastener driver 432. It is to be appreciated that the cassette 446 can be used to hold a variety of fastener shapes and sizes, and is not limited to the fastener 430, as described.

4. Steerable Guide Device

A steerable guide device 450 may be used to establish an open path through which an operative tool, such as the fastener device 400, can be deployed for use. FIGS. 55 and 56 show an embodiment of the steerable guide device 450. The steerable guide device comprises a flexible guide tube 452 carried by a handle 454. The handle is sized and configured to be ergonomically held by the clinician to introduce the guide tube 452 to the targeted site.

In order to establish an open path for the fastener device 400, the steerable guide device 450 includes an interior guide passage 456 which extends through the interior portion of the handle 454 continuously and into and through the guide tube 452. The distal end of the handle 454 may also include a seal 457 to restrict the flow of fluids through the guide tube 452. During introduction of the guide tube through the vasculature to the targeted site, an obturator or dilator 458 having a tip component 459 (see FIG. 57) is positioned within the guide tube 452 in order to seal the guide tube and restrict the flow of fluids through the guide tube 452, to provide an atraumatic tip for guiding through the vasculature, and to provide a guide wire lumen 470.

The handle assembly desirably includes a rotatable steering assembly 460 and a flushing port 462. The steering assembly 460 is used to deflect the proximal end 464 of the guide tube 452 to a bent or deflected configuration, as will be described later. The steering assembly 460 is rotated in a desired direction, causing the proximal end 464 to bend or deflect in a predetermined configuration. A radiopaque marker 466 can be placed on the proximal end region 464 of the guide tube 452 to allow for fluoroscopic visualization of the orientation of the deflected end region. In the bent or deflected configuration, the proximal end 464 can be oriented in a desired relationship with the targeted site.

Further details of the steerable guide device 450 can be found in U.S. patent application Ser. No. 11/254,619, filed 20

Oct. 2005, and entitled "Devices, Systems, and Methods for Guiding an Operative Tool Into an Interior Body Region," which is incorporated herein by reference.

V. Detailed Implantation Methods

The generally described steps of implantation of the prosthesis 100 provided in Section II will now be described in greater detail. In the illustrated embodiment, deployment of the bifurcated prosthesis 100 may generally be achieved in a twelve step process, for example, and is shown generally in FIGS. 58 through 78. The exemplary embodiment will describe the systems, methods, and uses of the tools for implanting the prosthesis 100. It is to be understood that these same or similar systems, methods, and tools may be used to implant other prosthesis configurations in other areas of the body as well. Throughout the implantation process, image guidance may be used and in conjunction with radiopaque markers positioned on the prosthesis 100 and deployment tools.

Access to the vascular system is commonly provided through the use of introducers known in the art. A hemostasis introducer sheath (not shown), for example, may be first positioned in the left femoral artery, providing access for the implantation tools. A second introducer sheath (not shown) may also be positioned in the right femoral artery, providing access for the implantation tools. It is to be understood that alternative access points may also be used. Access at both the left femoral artery and the right femoral artery, for example, allows for multiple implantation tools to be positioned within the vasculature at the same time, allowing the implantation procedure to be efficiently performed.

A. Position Main Body Prosthesis

Figure 58:
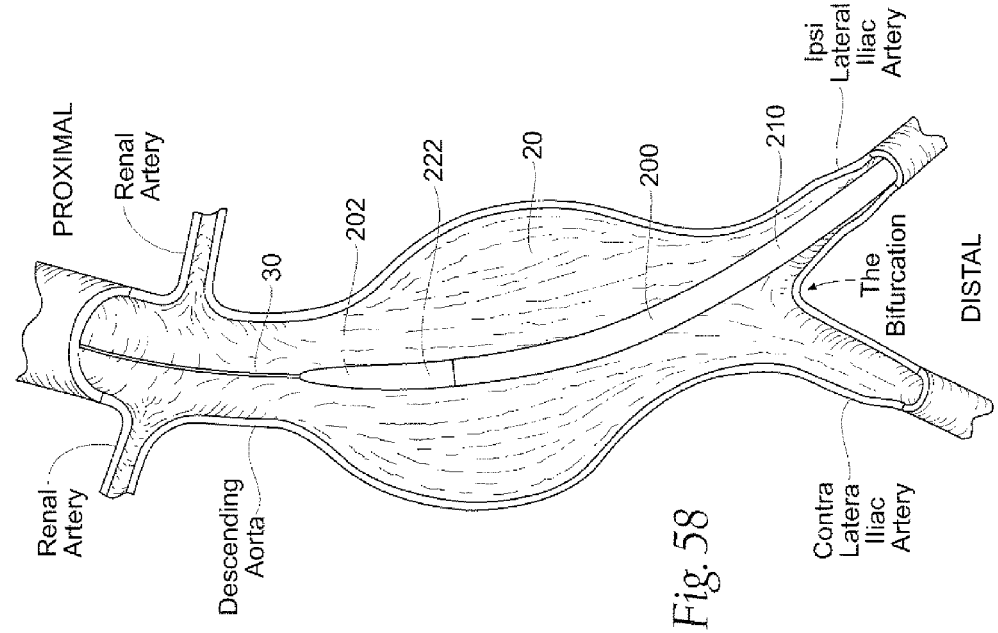
FIG. 58 is a perspective view of one embodiment of a prosthesis deployment catheter shown positioned with in an abdominal aortic aneurysm.

A first step includes positioning the main body prosthesis 120 at the desired location. From either the left or right femoral artery, under image guidance, the first guide wire 30 is advanced into the ipsilateral iliac artery and to the descending aorta. The deployment catheter 200 is then navigated over the first guide wire 30 to the desired location within the body, (e.g., aortic aneurysm), for deployment of the main body prosthesis 120 (as FIG. 58 shows). A conventional hemostatic valve arrangement may be used at the access site (shown for purposes of illustration in FIG. 44B).

B. Retract Outer Jacket

Figure 59:
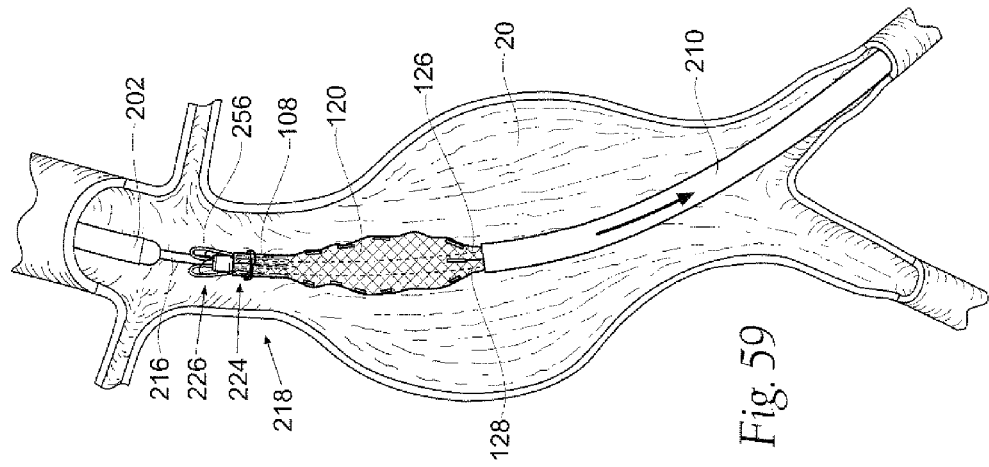
FIG. 59 is a perspective view of the deployment of the main body component of the multi-lumen prosthesis within the aneurysm of FIG. 58, with the jacket partially retracted.
Figure 61:
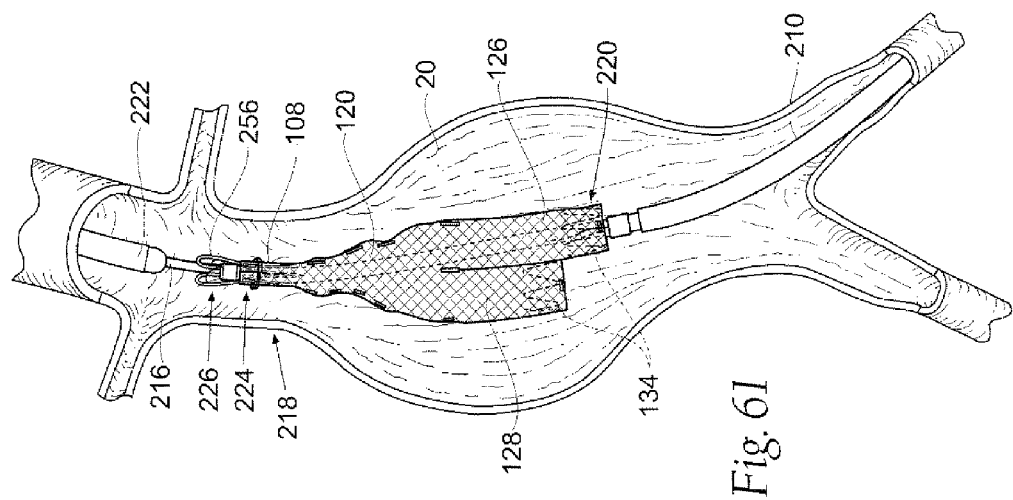
FIG. 61 is a perspective view of the deployment of the main body component of the multi-lumen prosthesis within the aneurysm of FIG. 58, with the jacket fully retracted but prior to the release of the proximal or distal retaining means and showing an alternative embodiment of the distal retaining means.

Next, the outer jacket 210 is retracted in a distal or caudal direction to expose the main body prosthesis 120. By first rotating the starting knob 302 on the handle assembly 212, the outer jacket 210 is initially retracted from its secure position on the catheter tip 222. After the mechanical advantage provided by the rotation of the starting knob 302 has retracted the outer jacket 210 away from the catheter tip 222, the jacket sliding knob 294 on the handle 212 may be used to further retract the jacket 210 and fully expose the main body prosthesis 120 (as FIGS. 59 and 60 show). The unrestrained portion or portions of the main body prosthesis 120 self-expand, as can be seen in FIG. 60. Optionally, the first lumen 126 may not be radially restrained, but still restrained in relation to the central shaft 216 (see FIG. 32), so as the outer jacket 210 is retracted, the first lumen 126 may self expand as well, as can be seen in FIG. 61. As FIGS. 59 through 61 show, both during and after retraction of the outer jacket 210, the main body prosthesis 120 maintains its position relative to the central shaft 216 due to the proximal and distal retaining means 218, 220, coupled to the main body prosthesis 120.

It should be appreciated that the withdrawal of the outer jacket 210 and the withdrawal of the proximal and distal releasing means 228, 230, 232, or any combination thereof, can be accomplished in a single step or process or in multiple steps. In this arrangement, a single activation mechanism can be jointly coupled to the outer jacket 210 and any or all of the releasing means 228, 230, 232, so that the outer jacket 210 and releasing means 228, 230, 232, are withdrawn in a single step, or multiple steps.

C. Release First Proximal Retaining Means

Figure 62:
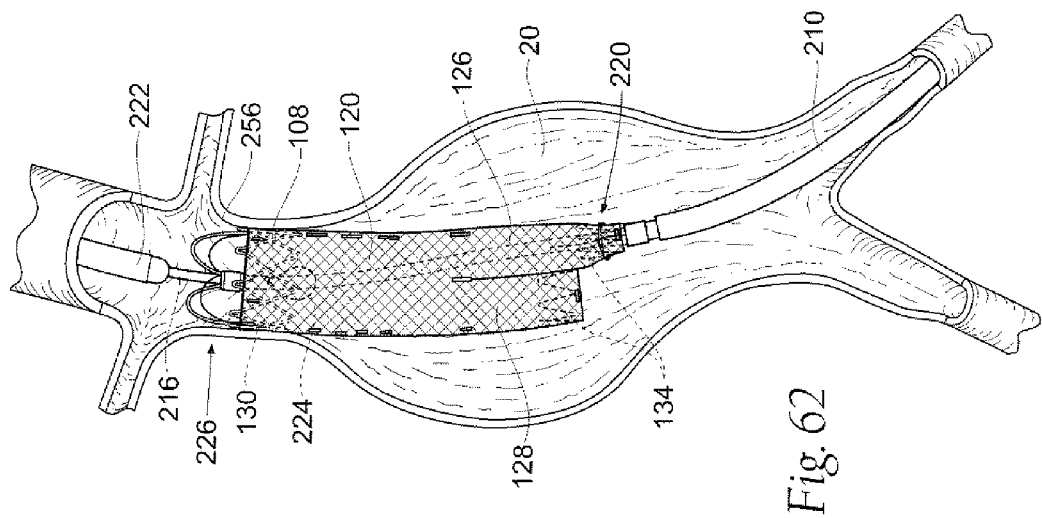
FIG. 62 is a perspective view of the deployment of the main body component of the multi-lumen prosthesis within the aneurysm of FIG. 58, and showing the first proximal retaining means released and the proximal end of the main body component expanded.
Figure 63:
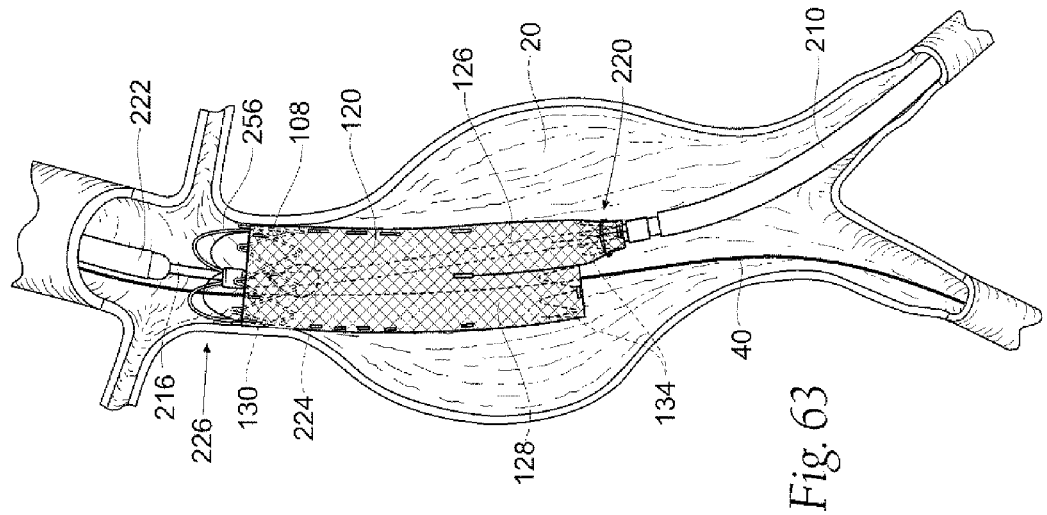
FIG. 63 is a perspective view of the deployment of the main body component of the multi-lumen prosthesis within the aneurysm of FIG. 58, and showing a second guide wire positioned through the main body prosthesis lumen.

In the third general step of the deployment process, following the withdrawal of the outer jacket 210, the first proximal sliding knob 322 on the handle assembly 212 is moved distally, which causes the proximal end of the first proximal releasing means 228, i.e., the first proximal release wire 250, to be withdrawn from the first proximal retaining means 224, i.e., the suture loop 252, and allows the restrained stent or stents 130, and the proximal end 108 of the main body prosthesis 120 as a whole, to self-expand radially to the first stage deployment configuration, as seen in FIG. 62. The proximal end 108 of the main body prosthesis 120 desirably radially expands to contact the internal walls of the vessel or hollow body organ.

D. Fasten Proximal End

The fourth general stage comprises fastening the proximal end 108 of the main body prosthesis 120 to the internal walls of the vessel or hollow body organ. From the right femoral artery, under image guidance, a second guide wire 40 is advanced using a conventional intravascular approach into the contralateral iliac artery and to the descending aorta. However, other access sites and methods can be utilized. The guide wire 40 desirably extends through the second expanded lumen 128 and through the proximal opening 122 of the main body prosthesis 120 (see FIG. 63). Next, the steerable guide device 450, with the obturator 458 positioned within the interior guide passage 456, is then navigated over the second guide wire 40 to the desired location with respect to the main body prosthesis 120 (see FIG. 64). Once the steerable guide device 450 is in position, the obturator 458 and the second guide wire 40 are both removed from the interior guide passage 456 and from the body.

Figure 65:
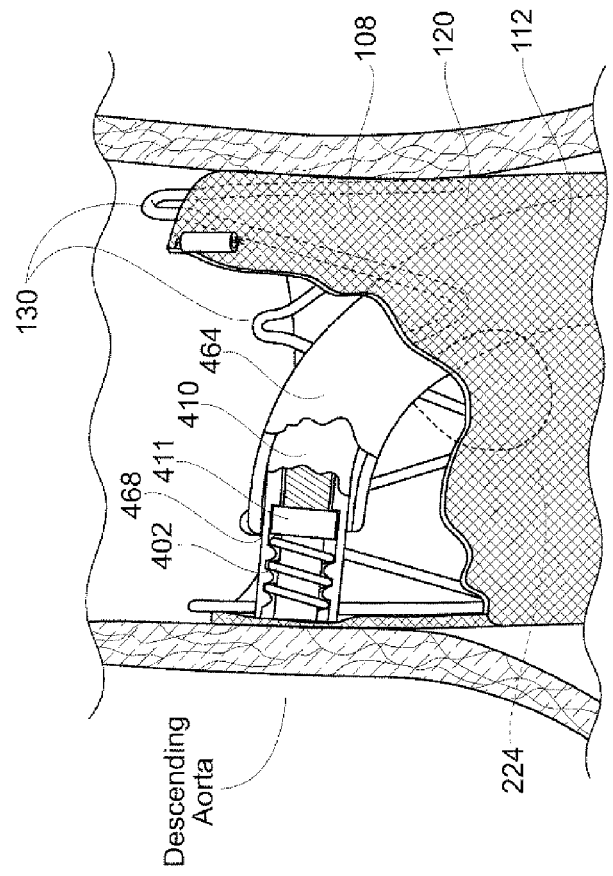
FIG. 65 is an enlarged perspective view of the deployment of the main body component of the multi-lumen prosthesis within the descending aorta, and showing the steerable guide device and the fastener tool just prior to fastening a helical fastener through the prosthesis material and into tissue.
Figure 64:
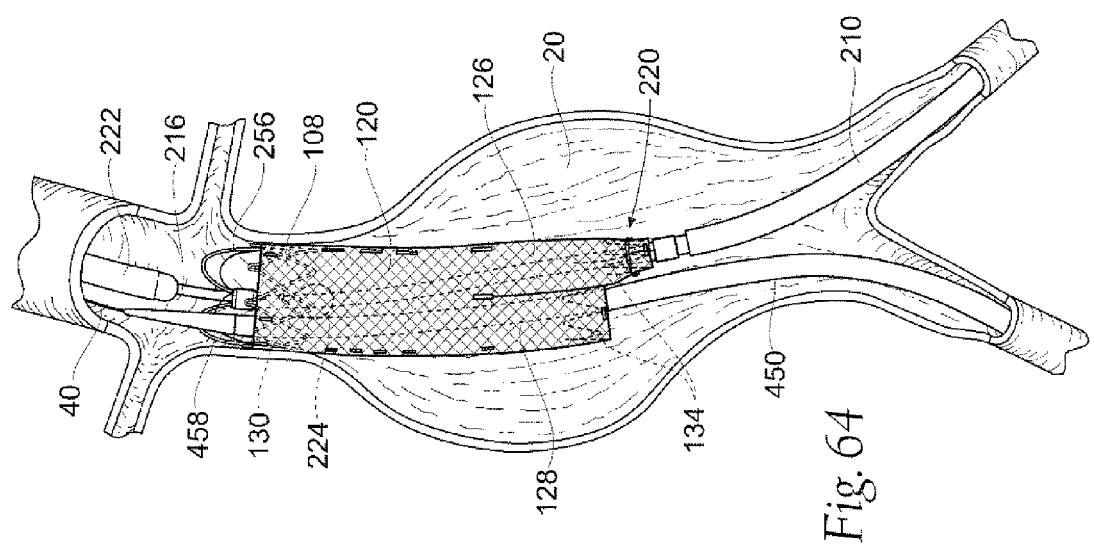
FIG. 64 is a perspective view of the deployment of the main body component of the multi-lumen prosthesis within the aneurysm of FIG. 58, and showing the steerable guide and obturator positioned on the second guide wire and through the main body prosthesis lumen.

By rotating the steering assembly 460 (see FIG. 55), and still employing fluoroscopy visualization, the clinician deflects the proximal end region 464—and rotates the handle 454 to rotate the flexible guide tube 452 if necessary—to orient the proximal opening 468 of the passage 456 in a desired facing relationship with the site where introduction of a fastener 402 is desired. An operative tool, such as the fastener device 400 is then inserted through the interior guide passage 456 of the steerable guide device 450, and advanced until a fastener, such as the fastener 402, is located for deployment in relation to the now—oriented proximal opening 468, as FIG. 65 shows. As the fastener device 400 is advanced out of the steerable guide device 450 and contacts the wall of the main body prosthesis 120, a resultant force is applied to the proximal end 464 of the steerable guide 450 which moves in the opposite direction of the fastener device proximal end 410. The resultant force causes the proximal end 464 of the steerable guide 450 to deflect until it contacts the opposite wall of the main body prosthesis within the lumen or hollow body organ. In this way, the force applied to the main body prosthesis 120 and vascular wall from the proximal end 410 of the fastener device 400 is partially resolved through the steerable guide 450 within the vessel or hollow body organ. A representative embodiment of an endovascular device that, in use, applies a helical fastener is described in U.S. patent application Ser. No. 10/786,465, filed Feb. 25, 2004, and entitled "Systems and Methods for Attaching a Prosthesis Within a Body Lumen or Hollow Organ," which is incorporated herein by reference.

Figure 68:
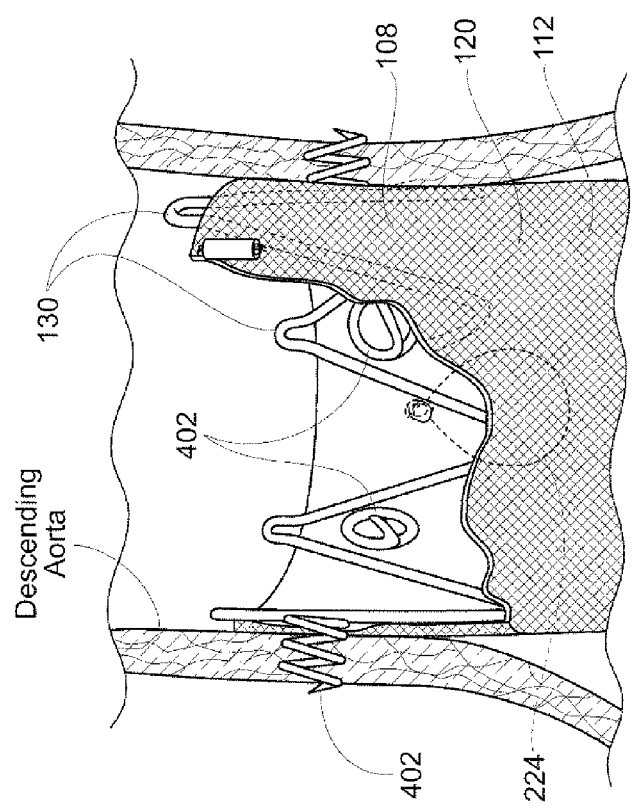
FIG. 68 is an enlarged perspective view of the deployment of the main body component of the multi-lumen prosthesis within the descending aorta, and showing one embodiment of a fastener deployment pattern.

The fastener device 400 can then be actuated to apply a fastener 402 to the proximal end 108 of the main body prosthesis 120 and into the surrounding tissue (see FIG. 66). If the fastener device 400 is a single fire device, i.e., it carries only one fastener 402, the fastener device 400 is withdrawn through the interior guide passage 456 and a new fastener 402 is mounted. See FIGS. 85 and 86 for one embodiment of the fastener 430 being mounted to the fastener device 400. The proximal end region 464 of the steerable device 450 is reoriented in facing relationship with a new fastening site. The fastener device 400 is inserted back through the interior guide passage 456 to apply a second fastener 402 to the new fastening site (see FIG. 67). This sequence is repeated until a desired number and array of fasteners 402 are applied to the main body prosthesis 120, as can be seen in FIG. 68.

At this point, the fastener device 400 is withdrawn, leaving the steerable guide device 450 in place. The obturator 458 is repositioned within the interior guide passage 456, and the second guide wire 40 is navigated through the obturator lumen 470 to the desired location with respect to the main body prosthesis 120. Once the second guide wire 40 is in position, the steerable guide device 450 and the obturator 458 are both removed from the interior guide passage 456 and from the body leaving the second guide wire 40 in position within the vasculature.

E. Position First Lumen Extension

In the fifth general stage of the deployment process, following the fastening of the proximal end 108 of the main body prosthesis 120, the extension deployment catheter 350 is used to position a lumen extension 140 for deployment within a lumen of the main body prosthesis 120. From the left or right femoral artery, under image guidance, the extension catheter 350 is navigated over the second guide wire 40 to the desired location, i.e., telescopically positioned partially within the second lumen 128 of the main body prosthesis 120, as FIG. 69 shows. A conventional hemostatic valve arrangement may be used at the access site (shown for purposes of illustration in FIG. 44B).

F. Retract Extension Catheter Outer Jacket

Next, the extension catheter's outer jacket 360 must be retracted in a distal or caudal direction to expose the lumen extension 140. The jacket sliding knob 382 on the extension catheter handle 362 is urged in a distal direction to retract the jacket 360 and fully expose the lumen extension 140. The unrestrained portion or portions of the lumen extension 140 self-expand (see FIG. 70). Both during and after retraction of the outer jacket 360, the lumen extension 140 maintains its position relative to the central shaft 356 due to the proximal retaining means 366, coupled to the lumen extension 140.

G. Release Lumen Extension Proximal Retaining Means

In the seventh general step of the deployment process, following the withdrawal of the extension catheter outer jacket 360, the proximal sliding knob 382 on the extension catheter handle assembly 362 is moved distally, which causes the proximal end of the proximal releasing means 370, i.e., the proximal release wire 380, to be withdrawn from the proximal retaining means 366, i.e., the suture loop 378, and allows the restrained stent or stents 150, and the proximal end 142 of the lumen extension 140, to self-expand radially to the deployment configuration, as seen in FIGS. 70 and 71. The proximal end 142 of the lumen extension 140 desirably enlarges to contact the internal walls of the second lumen 128 of the main body prosthesis 140. The natural flow of fluid through the lumen extension 140 provides sufficient force to cause the restraint mechanism of the lumen extension 140 to engage the co-acting restraint mechanism of the main body prosthesis 120. The lumen extension stent and/or outwardly extending apices 147 of the lumen extension stent 150 engage the mating outwardly extending apices 136 of the distal stent 134 positioned within the second lumen 128 of the main body prosthesis 120 (as best seen in FIG. 10B) in order to couple the lumen extension 140 to the main body prosthesis 120.

Prior to withdrawing the extension catheter 350, the outer jacket 360 is desirably repositioned in an abutting relationship with the catheter tip 368. The jacket sliding knob 382 on the extension catheter handle 362 is urged in a proximal direction to reposition the jacket 360 in a pre-deployment configuration. The extension catheter 350 may now be withdrawn and removed from the body. The second guide wire 40 may either be removed, or may remain until the deployment process is completed.

H. Release Second Proximal Retaining Means

Figure 72:
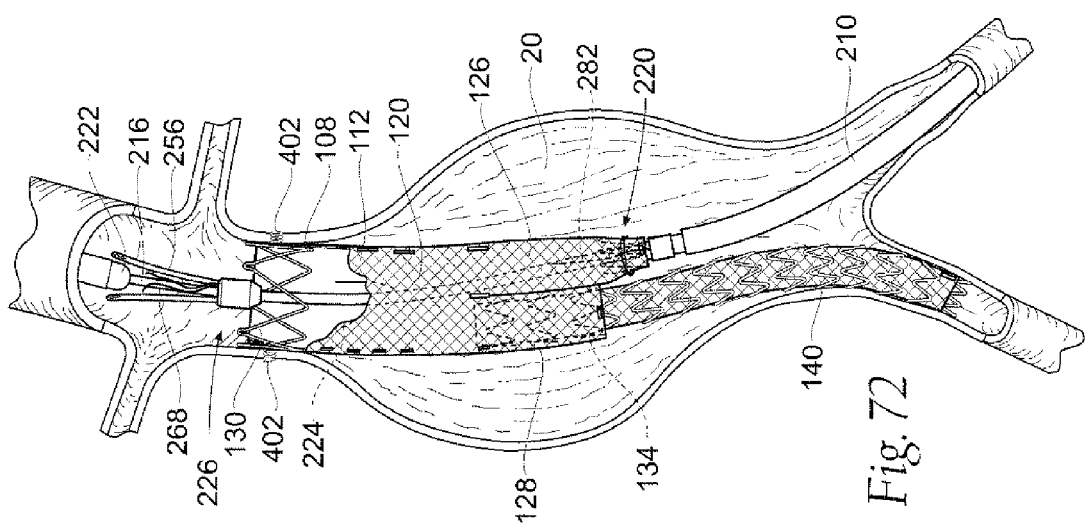
FIG. 72 is a perspective view of the deployment of the main body component of the multi-lumen prosthesis within the aneurysm of FIG. 58, and showing the lumen extension deployment catheter removed and the stabilizing arms of the main body deployment catheter released.

In the eighth general stage of the deployment process, following the deployment of a first lumen extension 140, the second proximal retaining means 226 is released. To release the proximal end 108 of the main body prosthesis 120, the second proximal release sliding knob 324 on the handle 212 is moved distally, which causes the proximal end of the second proximal releasing means 230, i.e., the second proximal release wire 268, to be withdrawn from the prosthesis material 112 and the stabilizing arm apertures 264, and allows the stabilizing arms 256 to release from the proximal end 108 of the main body prosthesis 120, and spring proximally, as shown in FIG. 72. The proximal end 108 of the main body prosthesis 120 is no longer in a restrained relationship with the central shaft 216.

I. Release Distal Retaining Means

Figure 73:
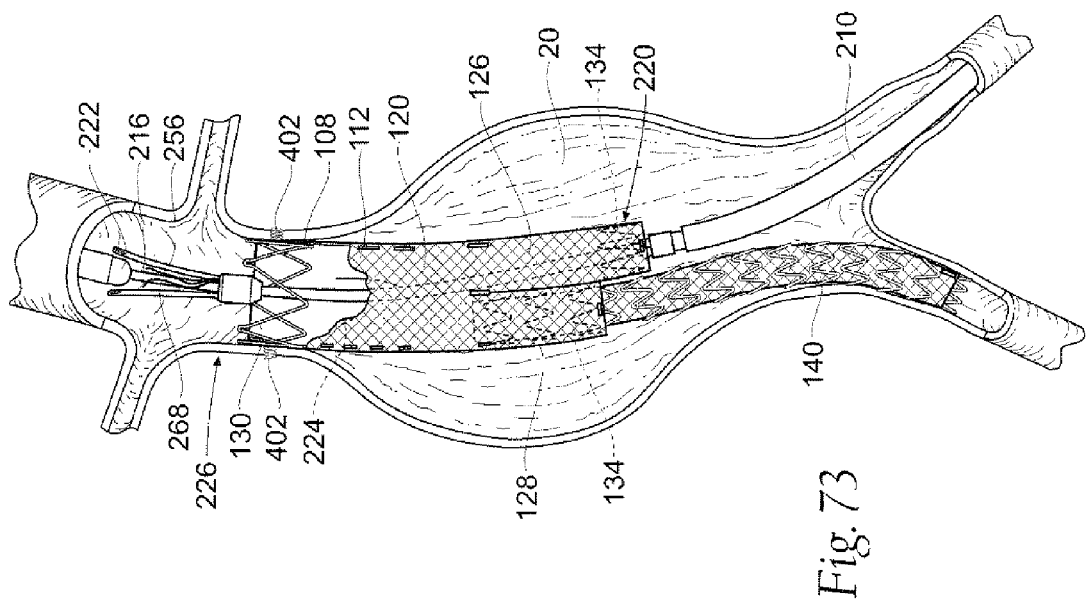
FIG. 73 is a perspective view of the deployment of the main body component of the multi-lumen prosthesis within the aneurysm of FIG. 58, and showing the distal retaining means released and the distal end of the main body prosthesis expanded.

In the ninth general stage of the deployment process, following the release of the second proximal retaining means 226, the distal retaining means 220 is released. To release the distal end 110 of the main body prosthesis 140, the distal release sliding knob 326 on the handle 212 is moved distally, which causes the proximal end of the distal releasing means 232, i.e., the distal release wire 282, to be withdrawn from the distal retaining means 220, i.e., the distal suture loop 274, and allows the restrained stent or stents 134 to self-expand radially to the second stage deployment configuration, as seen in FIG. 73. As previously mentioned, alternatively, the stent or stents 140 are not necessarily radially restrained by the distal retaining means 226. The main body prosthesis 120 is no longer in a restrained relationship with the central shaft 216.

Prior to withdrawing the deployment catheter 200, the outer jacket 210 is desirably repositioned in an abutting relationship with the catheter tip 222. The jacket sliding knob 294 on the catheter handle 212 is urged in a proximal direction to reposition the jacket 210 in a pre-deployment configuration. The deployment catheter 200 may now be withdrawn from the body, leaving the first guide wire 30 within the vasculature (see FIG. 74).

J. Position Second Lumen Extension

In the tenth general stage of the deployment process, following the release of the distal retaining means 220 and withdrawal of the deployment catheter 200, the second lumen extension 140 is positioned for deployment. The general steps as describe for the deployment of the first lumen extension 140 are the same or similar, but will be repeated here for clarity. The extension deployment catheter 350 is again used to position the second lumen extension 140 for deployment within a lumen of the main body prosthesis 120. From the left or right femoral artery, for example, under image guidance, the extension catheter 350 is navigated over the first guide wire 30 to the desired location, i.e., lescopically positioned partially within the first lumen 126 of the main body prosthesis 120, as FIG. 75 shows. Again, as previously described, a conventional hemostatic valve arrangement may be used at the access site (shown for purposes of illustration in FIG. 44B).

K. Retract Extension Catheter Outer Jacket

Figure 76:
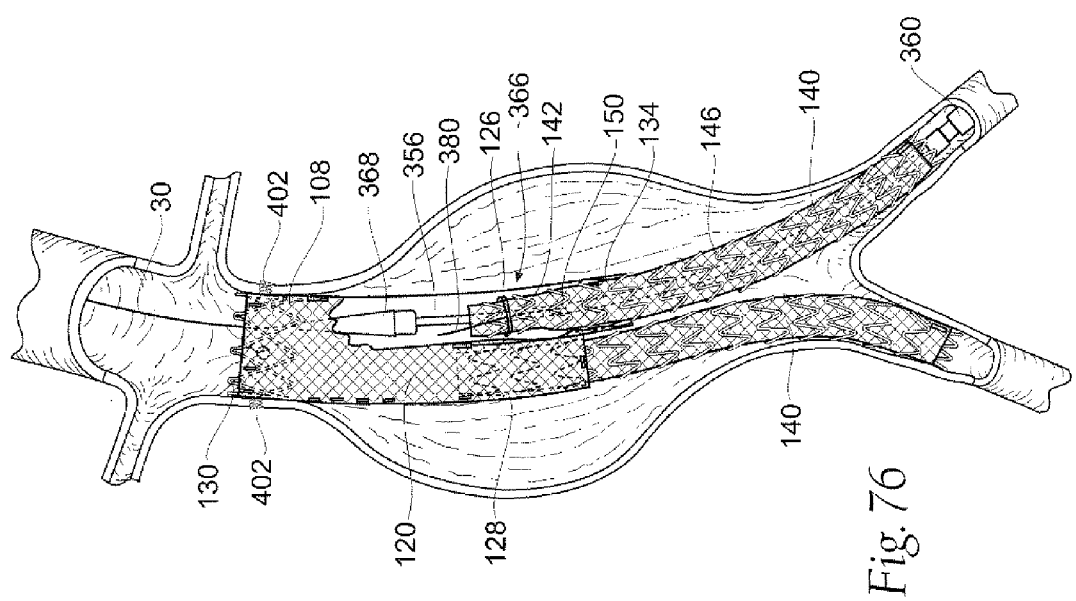
FIG. 76 is a perspective view of the deployment of the second lumen extension component of the multi-lumen prosthesis within the aneurysm of FIG. 58, and showing the jacket retracted from the lumen extension deployment catheter and prior to the release of a proximal retaining means.

Next, the extension catheter's outer jacket 360 must be retracted in a distal or caudal direction to expose the lumen extension 140. The jacket sliding knob 382 on the extension catheter handle 362 is urged in a distal direction to retract the jacket 360 and fully expose the lumen extension 140. The unrestrained portion or portions of the lumen extension 140 self-expand (see FIGS. 75 and 76). As FIG. 76 shows, both during and after retraction of the outer jacket 360, the lumen extension 140 maintains its position relative to the central shaft 356 due to the proximal retaining means 366, coupled to the lumen extension 140.

L. Release Lumen Extension Proximal Retaining Means

In the twelfth general step of the deployment process, following the withdrawal of the extension catheter outer jacket 360, the proximal sliding knob 382 on the extension catheter handle assembly 362 is moved distally, which causes the proximal end of the proximal releasing means 370, i.e., the proximal release wire 380, to be withdrawn from the proximal retaining means 366, i.e., the suture loop 378, and allows the restrained stent or stents 150, and the proximal end 142 of the lumen extension 140, to self-expand radially to the deployment configuration, as seen in FIG. 77. The proximal end 142 of the lumen extension 140 desirably enlarges to contact the internal walls of the first lumen 126 of the main body prosthesis 140. The natural flow of fluid through the lumen extension 140 provides sufficient force to cause the restraint mechanism of the lumen extension 140 to engage the co-acting restraint mechanism of the main body prosthesis 120. The lumen extension stent and/or the outwardly extending apices 147 of the lumen extension stent 150 engage the mating outwardly extending apices 136 of the distal stent 134 positioned within the first lumen 126 of the main body prosthesis 120 (as best seen in FIG. 10B) in order to couple the lumen extension 140 to the main body prosthesis 120.

Prior to withdrawing the extension catheter 350, the outer jacket 360 is desirably repositioned in an abutting relationship with the catheter tip 368. The jacket sliding knob 382 on the extension catheter handle 362 is urged in a proximal direction to reposition the jacket 360 in a pre-deployment configuration. The extension catheter 350 may now be withdrawn and removed from the body. Both the first guide wire 30 and the second guide wire 40 may now be removed to complete the deployment process of the bifurcated prosthesis 100, as can be seen in FIG. 78.

It is to be appreciated that the general steps just described do not necessarily need to follow the order in which they were described. For example, the second proximal retaining means may be released prior to the deployment of the first lumen extension 140, and the second guide wire may be removed prior to the completion of the deployment process. It is also to be appreciated that fasteners may be applied to the lumen extensions as well to connect the lumen extensions to the iliac arteries.

It will also be appreciated that the components and/or features of the preferred embodiments described herein may be used together or separately, while the depicted methods and devices may be combined or modified in whole or in part. It is contemplated that the components of the guiding device, fastener device, and helical fastener may be alternately oriented relative to each other, for example, offset, bi-axial, etc.

Further, it will be understood that the various embodiments may be used in additional procedures not described herein, such as vascular trauma, arterial dissections, artificial heart valve attachment and attachment of other prosthetic device within the vascular system and generally within the body.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

The desired embodiments of the invention are described above in detail for the purpose of setting forth a complete disclosure and for the sake of explanation and clarity. Those skilled in the art will envision other modifications within the scope and spirit of the present disclosure.

I claim:

1. A fastener applier for securing a prosthesis comprising
    a handle assembly positioned at the caudal end of the fastener applier,
    a fastener applier shaft coupled to the handle assembly, the fastener applier shaft comprising a cephalad end
    a fastener driver for advancing a fastener into the prosthesis and tissue,
    the fastener driver coupled to the fastener applier shaft at the cephalad end of the fastener applier shaft, the fastener driver including a housing and a release latch, wherein the release latch prevents premature release of the fastener from the fastener driver, and the fastener is a helical fastener.

2. A fastener applier according to claim 1 wherein the fastener driver housing includes an internally threaded portion and a non-threaded portion, the non-threaded portion providing an area where the fastener can be rotated but not advanced out of the driver, the advancement out of the driver only taking place if the fastener has been previously engaged in tissue or the prosthesis.

3. A fastener applier according to claim 1 wherein the handle assembly further includes a motion control assembly to be used by an operator, the motion control assembly providing motion control of the fastener within the fastener driver.

4. A fastener applier according to claim 3 wherein the motion control assembly includes a forward control function and a reverse control function.

5. A fastener applier according to claim 1 wherein the handle assembly further includes an indication assembly to provide information to an operator, the indication assembly providing at least one of an audible and visual indication.

6. A fastener applier according to claim 5 wherein the information includes at least one of a fastener position or timing or status or error, or any combination.

7. A fastener applier according to claim 1 wherein the helical fastener includes a fastener body having a distal end for penetrating tissue in response to a force and a proximal end for releasably coupling the fastener body to the fastener applier, and a stop structure associated with the proximal end to prevent over-penetration of the fastener body into tissue, the stop structure bisecting the diameter of the fastener body.

8. A fastener applier according to claim 7 wherein the stop structure is offset from the diameter of the fastener body.

* * * * *